United States Patent
Steinhauer et al.

(10) Patent No.: US 10,179,217 B2
(45) Date of Patent: *Jan. 15, 2019

(54) RESPIRATORY KNOWLEDGE PORTAL

(71) Applicant: CareFusion 303, Inc., San Diego, CA (US)

(72) Inventors: Tom Steinhauer, San Diego, CA (US); Willis Lam, San Diego, CA (US); Terry Blansfield, Orange, CA (US); Stephen J. Birch, Mission Viejo, CA (US); Leonard Mulkowsky, Del Mar, CA (US); Clifton Pait, San Diego, CA (US); Mark Rogers, Irvine, CA (US)

(73) Assignee: Vyaire Medical Capital LLC, Yorba Linda, CA (US)

( * ) Notice: Subject to any disclaimer, the term of this patent is extended or adjusted under 35 U.S.C. 154(b) by 247 days.

This patent is subject to a terminal disclaimer.

(21) Appl. No.: 15/082,909

(22) Filed: Mar. 28, 2016

(65) Prior Publication Data

US 2016/0206838 A1 Jul. 21, 2016

Related U.S. Application Data

(63) Continuation of application No. 13/756,421, filed on Jan. 31, 2013, now Pat. No. 9,327,090, which is a (Continued)

(51) Int. Cl.
*A61M 16/00* (2006.01)
*G06F 19/00* (2018.01)

(52) U.S. Cl.
CPC .... *A61M 16/0069* (2014.02); *A61M 16/0051* (2013.01); *A61M 16/0057* (2013.01); (Continued)

(58) Field of Classification Search
CPC .............. A61M 16/00; A61M 16/0009; A61M 16/0051; A61M 16/0057; A61M 16/0066; (Continued)

(56) References Cited

U.S. PATENT DOCUMENTS

| 4,988,336 A | 1/1991 | Kohn |
| 5,065,315 A | 11/1991 | Garcia |

(Continued)

FOREIGN PATENT DOCUMENTS

| WO | WO-0244993 A2 | 6/2002 |
| WO | WO-2011/087111 A1 | 7/2011 |
| WO | WO-2013/067223 A1 | 5/2013 |

OTHER PUBLICATIONS

Fairley, H. Barrie, and B.A. Britt. "The adequacy of the air-mix control in ventilators operated from an oxygen source." Canadian Medical Association Journal 90.25 (1964): 1394.

(Continued)

*Primary Examiner* — Annette Dixon
(74) *Attorney, Agent, or Firm* — Morgan, Lewis & Bockius LLP

(57) ABSTRACT

A monitoring system for multiple medical ventilators is provided. In one aspect, the monitoring system includes a memory that includes instructions, and a processor. The processor is configured to execute the instructions to receive data for a plurality of medical ventilators, and identify a configuration for each of the plurality of medical ventilators from the received data for the plurality of medical ventilators. The processor is also configured to execute the instructions to associate each patient with a respective one of the plurality of medical ventilators, determine an identification and status for each patient associated with one of the plurality of medical ventilators, and provide, for display, information indicative of the configuration of each of the plurality of medical ventilators and indicative of the iden- (Continued)

tification and status of each patient associated with one of the plurality of medical ventilators. Methods and machine-readable media are also provided.

35 Claims, 67 Drawing Sheets

Related U.S. Application Data continuation-in-part of application No. 13/538,834, filed on Jun. 29, 2012, now Pat. No. 9,352,110.

(52) U.S. Cl.
CPC ....... *A61M 16/026* (2017.08); *G06F 19/3418* (2013.01); *A61M 2205/52* (2013.01)

(58) Field of Classification Search
CPC ............ A61M 16/0069; A61M 16/021; A61M 16/026; A61M 16/107; A61M 2016/0021; A61M 2016/0033; A61M 2016/0036; A61M 2016/1025; A61M 2202/0014; A61M 2202/0208; A61M 2202/0275; A61M 2202/0466; A61M 2205/075; A61M 2205/3375; A61M 2205/3553; A61M 2205/3561; A61M 2205/3576; A61M 2205/3584; A61M 2205/3592; A61M 2205/502; A61M 2205/505; A61M 2205/52; A61M 2205/584; A61M 2205/60; A61M 2205/6018; A61M 2205/6054; A61M 2205/6072; A61M 2205/609; A61M 2205/8206; A61M 2205/84; A61M 2209/01; A61M 2209/086; A61M 2230/04; A61M 2230/10; A61M 2230/18; A61M 2230/202; A61M 2230/205; A61M 2230/60; A61M 2230/62; A61M 2230/63; F04D 25/166; F04D 29/052; G06F 19/30; G06F 19/325; G06F 19/327; G06F 19/3406; G06F 19/3412; G06F 19/3418; G06F 19/345; G06F 19/3456; G06F 19/3481; G06F 19/3487; G06Q 10/00; G06Q 10/087; G06Q 30/04; G06Q 50/22; G06Q 50/24; H04B 7/00; A61B 5/00; A61B 5/087
USPC ............ 128/200.24, 202.27, 204.18, 204.21, 128/204.22, 204.23, 204.24, 205.23; 600/301; 705/2
See application file for complete search history.

(56) References Cited

U.S. PATENT DOCUMENTS

| | | |
|---|---|---|
| 5,544,649 A | 8/1996 | David et al. |
| 5,626,151 A | 5/1997 | Linden |
| 5,881,723 A | 3/1999 | Wallace et al. |
| 5,931,160 A | 8/1999 | Gilmore et al. |
| 5,987,519 A | 11/1999 | Peifer et al. |
| 6,148,814 A | 11/2000 | Clemmer et al. |
| 6,158,430 A | 12/2000 | Pfeiffer et al. |
| 6,158,433 A | 12/2000 | Ong et al. |
| 6,349,724 B1 | 2/2002 | Burton et al. |
| 6,369,847 B1 | 4/2002 | James et al. |
| 6,406,426 B1 | 6/2002 | Reuss et al. |
| 6,459,933 B1 | 10/2002 | Lurie et al. |
| 6,551,243 B2 | 4/2003 | Bocionek et al. |
| 6,666,820 B1 | 12/2003 | Poole |
| 6,839,753 B2 | 1/2005 | Biondi et al. |
| 6,955,170 B1 | 10/2005 | Mullins et al. |
| 7,165,221 B2 | 1/2007 | Monteleone et al. |
| 7,225,809 B1 | 6/2007 | Bowen et al. |
| 7,237,205 B2 | 6/2007 | Sarel |
| 7,334,578 B2 | 2/2008 | Biondi et al. |
| 7,395,216 B2 | 7/2008 | Rosenfeld et al. |
| 7,610,099 B2 | 10/2009 | Almendinger et al. |
| 7,668,596 B2 | 2/2010 | Von Arx et al. |
| 7,677,246 B2 | 3/2010 | Kepler et al. |
| 7,698,156 B2 | 4/2010 | Martucci et al. |
| 7,933,780 B2 | 4/2011 | De La Huerga |
| 8,015,972 B2 | 9/2011 | Pirzada |
| 8,255,238 B2 | 8/2012 | Powell et al. |
| 8,321,284 B2 | 11/2012 | Clements et al. |
| 8,327,846 B2 | 12/2012 | Bowditch et al. |
| 8,447,629 B2 | 5/2013 | Rappaport et al. |
| 8,522,779 B2 | 9/2013 | Lee et al. |
| 8,695,593 B2 | 4/2014 | Tehrani |
| 9,327,090 B2 * | 5/2016 | Steinhauer ........ A61M 16/0069 |
| 2001/0016821 A1 | 8/2001 | DeBusk et al. |
| 2001/0027791 A1 | 10/2001 | Wallace et al. |
| 2002/0022973 A1 | 2/2002 | Sun et al. |
| 2002/0026941 A1 | 3/2002 | Biondi et al. |
| 2002/0077862 A1 | 6/2002 | Auer et al. |
| 2002/0091309 A1 | 7/2002 | Auer |
| 2002/0120676 A1 | 8/2002 | Biondi et al. |
| 2002/0133061 A1 | 9/2002 | Manetta |
| 2003/0050802 A1 | 3/2003 | Jay et al. |
| 2003/0101076 A1 | 5/2003 | Zaleski |
| 2004/0077934 A1 | 4/2004 | Massad |
| 2004/0249675 A1 | 12/2004 | Stark et al. |
| 2005/0108057 A1 | 5/2005 | Cohen et al. |
| 2005/0137653 A1 | 6/2005 | Friedman et al. |
| 2005/0151640 A1 | 7/2005 | Hastings |
| 2005/0188083 A1 | 8/2005 | Biondi et al. |
| 2005/0192845 A1 | 9/2005 | Brinsfield et al. |
| 2005/0267348 A1 | 12/2005 | Wollenweber et al. |
| 2005/0268916 A1 | 12/2005 | Mumford et al. |
| 2006/0031095 A1 | 2/2006 | Barth et al. |
| 2006/0162727 A1 | 7/2006 | Biondi et al. |
| 2006/0174883 A1 | 8/2006 | Aylsworth et al. |
| 2006/0180150 A1 | 8/2006 | Dittmann |
| 2006/0206011 A1 | 9/2006 | Higgins et al. |
| 2006/0289020 A1 | 12/2006 | Tabak et al. |
| 2007/0005621 A1 | 1/2007 | Lesh et al. |
| 2007/0015976 A1 | 1/2007 | Miesel et al. |
| 2007/0023045 A1 | 2/2007 | Kwok et al. |
| 2007/0033072 A1 | 2/2007 | Bildirici |
| 2007/0276696 A1 | 11/2007 | Gauvin et al. |
| 2007/0283958 A1 | 12/2007 | Miesel et al. |
| 2008/0053438 A1 | 3/2008 | DeVries et al. |
| 2008/0072902 A1 | 3/2008 | Setzer et al. |
| 2008/0077436 A1 | 3/2008 | Muradia |
| 2008/0086691 A1 | 4/2008 | Hopermann et al. |
| 2008/0091466 A1 | 4/2008 | Butler et al. |
| 2008/0097793 A1 | 4/2008 | Dicks et al. |
| 2008/0097913 A1 | 4/2008 | Dicks et al. |
| 2008/0140160 A1 | 6/2008 | Goetz et al. |
| 2008/0230064 A1 | 9/2008 | Tham |
| 2008/0271736 A1 | 11/2008 | Leonard et al. |
| 2008/0288023 A1 | 11/2008 | John |
| 2008/0308101 A1 | 12/2008 | Spandorfer |
| 2008/0312548 A1 | 12/2008 | Hartley et al. |
| 2009/0044803 A1 | 2/2009 | Garcia Fernandez |
| 2009/0112160 A1 | 4/2009 | Yang |
| 2009/0171696 A1 | 7/2009 | Allard et al. |
| 2009/0184823 A1 | 7/2009 | Tessier |
| 2009/0229610 A1 | 9/2009 | Oates et al. |
| 2009/0241956 A1 | 10/2009 | Baker, Jr. et al. |
| 2009/0293886 A1 | 12/2009 | Dedrick et al. |
| 2009/0326389 A1 | 12/2009 | Ralfs |
| 2010/0071697 A1 | 3/2010 | Jafari et al. |
| 2010/0078017 A1 | 4/2010 | Andrieux et al. |
| 2010/0083968 A1 | 4/2010 | Wondka et al. |
| 2010/0085156 A1 | 4/2010 | Tucker |
| 2010/0108064 A1 | 5/2010 | Blackwell et al. |
| 2010/0161345 A1 | 6/2010 | Cain et al. |
| 2010/0202354 A1 | 8/2010 | Ho |
| 2010/0287006 A1 | 11/2010 | Cannon et al. |
| 2010/0288279 A1 | 11/2010 | Seiver et al. |

(56) References Cited

U.S. PATENT DOCUMENTS

| | | |
|---|---|---|
| 2010/0298718 A1 | 11/2010 | Gilham et al. |
| 2010/0318155 A1 | 12/2010 | Mahajan et al. |
| 2011/0011400 A1 | 1/2011 | Gentner et al. |
| 2011/0034783 A1 | 2/2011 | Lisogurski et al. |
| 2011/0073107 A1 | 3/2011 | Rodman et al. |
| 2011/0077970 A1 | 3/2011 | Mellin et al. |
| 2011/0078253 A1 | 3/2011 | Chan et al. |
| 2011/0087756 A1 | 4/2011 | Biondi et al. |
| 2011/0107251 A1 | 5/2011 | Guaitoli et al. |
| 2011/0108034 A1 | 5/2011 | Viertio-Oja |
| 2011/0112442 A1 | 5/2011 | Meger et al. |
| 2011/0120470 A1 | 5/2011 | Bowerbank |
| 2011/0139155 A1 | 6/2011 | Farrell et al. |
| 2011/0178373 A1 | 7/2011 | Pacey et al. |
| 2011/0208539 A1 | 8/2011 | Lynn |
| 2011/0231505 A1 | 9/2011 | Chan et al. |
| 2011/0238441 A1 | 9/2011 | Callas |
| 2011/0319322 A1 | 12/2011 | Bashan et al. |
| 2012/0082036 A1 | 4/2012 | Abedi et al. |
| 2012/0108984 A1 | 5/2012 | Bennett et al. |
| 2012/0109240 A1 | 5/2012 | Zhou et al. |
| 2012/0118285 A1 | 5/2012 | Wondka et al. |
| 2012/0137250 A1 | 5/2012 | Milne et al. |
| 2012/0145153 A1 | 6/2012 | Bassin et al. |
| 2012/0216809 A1 | 8/2012 | Milne et al. |
| 2012/0272955 A1 | 11/2012 | Cool et al. |
| 2012/0330177 A1 | 12/2012 | Al-Rawas et al. |
| 2013/0032147 A1 | 2/2013 | Robinson et al. |
| 2013/0186405 A1 | 7/2013 | Krzyzanowski et al. |
| 2013/0199533 A1 | 8/2013 | Steinhauer et al. |
| 2014/0158124 A1 | 6/2014 | L'her et al. |

OTHER PUBLICATIONS

Krieger, Bruce P., et al. "Initial experience with a central respiratory monitoring unit as a cost-saving alternative to the intensive care unit for Medicare patients who require long-term ventilator support." Chest Journal 93.2 (1988): 395-397.

Simonds, A. K. "Streamlining wearning: protocols and weaning units." Thorax 60.3 (2005): 175-182.

Chipman, Daniel W., et al. "Performance comparison of 15 transport ventilators." Respiratory care 52.6 (2007): 740-751.

"AVEA Ventilator Systems Operator's Manual", Cardinal Health, Sep. 1, 2008, pp. 1-244, XP055077133, Retrieved from the Internet: URL:http://www.frankshospitalworkshop.com/equipment/documents/ventilators/user_manuals/Cardinal_Health_avea_-_User_manual.pdf.

Shimpi, A.L., "iphone 3GS Performance: A Significant Performance Bump," Anand Tech (2009), http://www.anandtech.com/show/2790.

Govoni, et al., "An Improved Telemedicine System for Remote Titration and Optimization of Home Mechanical Ventilation", Biomedical Engineering Conference (CIBEC), 2010 5th Cairo International, IEEE, Dec. 16, 2010, pp. 66-69, XP031979754.

"Medicare Quarterly Provider Compliance Newsletter", Oct. 2011, 21 pages, vol. 2, Issue 1, CMS.

"Carefusion Announces New Ventilation Solution to Help Hospitals Provide improved Patient Care and Reduce Costs", Feb. 21, 2012, pp. 1-2, XP055077131, Retrieved from the Internet: URL:http://media.carefusion.com/index.php?s=32344&item=106634.

Title: CPAP Equipment: CPAP Software Date Archived: May 12, 2012 Publisher: cpap.com.

"Solutions," retrieved on Sep. 16, 2013, 1 page, Theronyx, retrieved from <http://www.theronyx.com/solutions>.

"Vital Sync Virtual Patient monitoring Platform 2.0," retrieved on Sep. 16, 2013, 2 pages, Covidien, retrieved from <http://www.covidien.com/RMS/pages.aspx?page+Product/Vital-Sync-Vitrual-Patient-Monitoring-Platform>.

International Search Report and Written Opinion for International Application No. PCT/US2013/048734, dated Sep. 9, 2013, 12 pages.

International Preliminary Report of Patentability for International Application No. PCT/US2013/048734, dated Dec. 31, 2014, 8 pages.

Extended European Search Report for Application No. 12844716.6, dated Jan. 4, 2016, 12 pages.

European Office Action for Application No. 12844716.6, dated Nov. 6, 2017, 7 pages.

Extended European Search Report for Application No. 13878057.2, dated Oct. 4, 2016, 8 pages.

International Search Report for International Application No. PCT/US2013/057860, dated Nov. 7, 2013, 2 pages.

International Search Report for International Application No. PCT/US2013/057862, dated Dec. 12, 2013, 2 pages.

* cited by examiner

17230 →

Knowledge Portal  Welcome! John Doe | Change Password | Mobile | Help | Sign Out System | Supply Management | Products | Respiratory ▼

Home > Marker View  Data Current as of : 8/21/2012 7:10:02 PM

Site In Analysis
IDN0000001 ▶
Hospital01 ▶

Executive Summary | Patient View | Marker View

Marker View  ☐ Make this my default view

All Active Markers Displayed — 17231 — 17232  List is Unfiltered  [Edit Criteria ✎] — 17234

| MRN | Account ID | Patient Name | Marker Time | Status | Priority | Marker |
|---|---|---|---|---|---|---|
| MRN0050056 | Visit86791 | PatLn50056, PatFn50056 | 8/24/2012 5:14 PM | Active | High | Mand Vte has exceeded the configured Lung Protective Strategies guideline |
| MRN0050365 | Visit87416 | PatLn50365, PatFn50365 | 8/24/2012 5:14 PM | Active | High | Weaning Candidate - No SBT Attempt |
| MRN0027096 | Visit87110 | PatLn27096, PatFn27096 | 8/24/2012 5:14 PM | Active | High | Weaning Candidate - No SBT Attempt |
| MRN0049772 | Visit86135 | PatLn49772, PatFn49772 | 8/24/2012 5:14 PM | Active | Med | Set Ppeak low alarm limit is non-compliant with operational policy |
| MRN0050056 | Visit86791 | PatLn50056, PatFn50056 | 8/24/2012 5:14 PM | Active | Med | Set Ppeak low alarm limit is non-compliant with operational policy |
| MRN0027096 | Visit87110 | PatLn27096, PatFn27096 | 8/24/2012 5:14 PM | Active | Med | Set Ppeak low alarm limit is non-compliant with operational policy |
| MRN0036865 | Visit79283 | PatLn36865, PatFn36865 | 8/24/2012 5:14 PM | Active | Med | Set Ppeak high alarm limit is non-compliant with operational policy |
| MRN0050056 | Visit86791 | PatLn50056, PatFn50056 | 8/24/2012 5:14 PM | Active | Med | Set Ppeak high alarm limit is non-compliant with operational policy |
| MRN0050365 | Visit87416 | PatLn50365, PatFn50365 | 8/24/2012 5:14 PM | Active | Med | Set Ppeak high alarm limit is non-compliant with operational policy |
| MRN0048482 | Visit83334 | PatLn48482, PatFn48482 | 8/24/2012 5:14 PM | Active | Med | Set Ppeak high alarm limit is non-compliant with operational policy |
| MRN0034833 | Visit85830 | PatLn34833, PatFn34833 | 8/24/2012 5:14 PM | Active | Med | Set Ppeak high alarm limit is non-compliant with operational policy |
| MRN0050445 | Visit87574 | PatLn50445, PatFn50445 | 8/24/2012 5:14 PM | Active | Med | Set Ve high alarm limit is non-compliant with operational policy |
| MRN0050445 | Visit87574 | PatLn50445, PatFn50445 | 8/24/2012 5:14 PM | Active | Med | Set Ppeak low alarm limit is non-compliant with operational policy |

Knowledge Portal

Welcome! John Doe | Change Password | Mobile | Help | Sign Out

System  Supply Management  Products  | Respiratory ▼ |

Home > Executive Summary — 17241

Data Current as of: August 21, 2012

Site In Analysis
- IDN0000001 ▼
- Hospital01 ▼

| Executive Summary | Patient View | Marker View |

Executive Summary

Performance Scorecard for CareTaken Ventilators  
Site: IDN0000001 - Hospital01 — 17242, 17243

☐ Make this my default view

Summary By: Month  
Comparison Period: July 2012  
Current Period: August 2012

[Edit Criteria ✎]

| Key Performance Indicators (KPIs) | Current Period (17244) | Comparison Period (17245) | Difference (17246) | Trend (17249) |
|---|---|---|---|---|
| ▽ Category: Weaning Analytics | | | | |
| Number of All Vent Patients | 31 | 41 | -10 | Trend ? |
| Average Vent Days for All Patients | 3.42 | 3.04 | 0.38 | Trend ? |
| Total Estimated Vent Cost ($) for All Patients | ⊘ $310,878 | $358,592 | -$47,714 | Trend ? |
| Reintubation Rate (%) for All Patients | ⊘ 3 | 5 | -2 | Trend ? |
| Number of Weaning Candidates | 27 | 38 | -11 | Trend ? |
| Average Vent Days for Weaning Candidates | 3.86 | 3.25 | 0.61 | Trend ? |
| Total Estimated Vent Cost ($) for Weaning Candidates | ⊘ $307,095 | $356,576 | -$49,481 | Trend ? |
| ▽ Category: Long Protection Analytics | | | | |

Knowledge Portal  Welcome! John Doe | Change Password | Mobile | Help | Sign Out System  Supply Management  Products  | Respiratory ▼ |

Home > Patient View > Patient Details                                    Data Current as of : 8/21/2012 7:10:02 PM

Patient Details

PatLn50056, PatFn50056
MRN: MRN0050056
Care Area: SICU Bed: B000000423
Status: Active

| Ventilator Information |
|---|
| Ventilator Type: Avea |
| Ventilator Started 8/17/2012 8:36 PM |

Settings — 17271

| Setting | Latest Value | Trend (Last 24 Hrs) |
|---|---|---|
| AAC On | 0 | |
| Apnea Interval (sec) | 20 | |
| Bias Flow (L/min) | 2.5 | |
| Circ Comp (mL/cmH2O) | 3.2 | |
| CO2 | Disabled | |
| Demand Flow | 1 | |
| Diameter (mm) | 7.5 | |
| EtCO2 Avg (Breath) | 8 | |

Measured Values — 17272

| Metric | Latest Value | Trend (Last 24 Hrs) |
|---|---|---|
| Cdyn (mL/cmH2O) | 20.39 | |
| Cstat (mL/cmH2O) | 20.47 | |
| FiO2 (%) | 100 | |
| I:E | -1.9 | |
| Mand Rate (bpm) | 29 | |
| Mand Vte (mL) | 472.262 | |
| Minute Ventilation (L) | 15.49 | |
| PEEP (cmH2O) | 10 | |

Reports

Select Report: [      ▼] [View]

Markers

| Marker Time | Marker |
|---|---|
| 8/24/2012 5:14 PM | Set Ppeak low alarm limit is non-compliant with operational policy |
| 8/24/2012 5:14 PM | Mand Vte has exceeded the configured Lung Protective Strategies guideline |
| 8/24/2012 5:14 PM | Set Ppeak high alarm limit is non-compliant with operational policy |

Care Notes                                         [Add Care Note]

| Entered On | Care Note |
|---|---|

FIG. 17H

Knowledge Portal — Welcome! John Doe | Change Password | Mobile | Help | Sign Out System  Supply Management  Products  | Respiratory ▼ |

Home > Executive Summary > Care Area > Physician                                                     Data Current as of : August 21, 2012

| Site In Analysis |
| IDN0000001 ▶ |
| Hospital01 ▶ |

KPI Detail                                                                                                  [Export] [Print]

Site: IDN0000001 - Hospital01                             Start Date: August 1, 2012
Kpi: Lung Protection Analytics                            End Date: August 31, 2012                 [Edit Criteria ✎]
View: Care Area (SICU) then Physician ⊙ Table View  ○ Chart View       Analysis Path | Care Area then Physician then Patient Summary then Patient Details ▶ |

17291 — | 17292 — | 17243 — | 17294 — | 17295 — |

| Care Area | Physician | # of Patients with LP Markers | Avg Vent Days | Avg # of Times Outside Threshold | Avg # of Hours Outside Threshold | |
|---|---|---|---|---|---|---|
| SICU | DocLn00120, DocFn00120 | 1 | 0.18 | 3 | 3.7 | Trend |
| SICU | DocLn00067, DocFn00067 | 1 | 0.36 | 7 | 5.1 | Trend |
| SICU | DocLn00155, DocFn00155 | 1 | 3.94 | 15 | 8.8 | Trend |

◀ ◁ ① ▷ ▶                                                                                                      1 - 3 of 3 items 17208
17296

| Knowledge Portal | Welcome! John Doe | Change Password | Mobile | Help | Sign Out |

System  Supply Management  Products  | Respiratory ▼ |

Home > Lung Protective Strategies Summary Report

Lung Protective Strategies Summary Report : Select parameters

Select Admissions (Patient Name - AccountID - Ventilator Start Time)

PatLn50445, PatFn50445 - Visit87574 - 8/21/2012 6:27PM
PatLn50397, PatFn50397 - Visit87472 - 8/21/2012 12:38PM
PatLn50365, PatFn50365 - Visit87416 - 8/21/2012 1:52AM
PatLn06788, PatFn06788 - Visit84741 - 8/20/2012 9:17PM
PatLn50242, PatFn50242 - Visit87146 - 8/20/2012 6:49AM
PatLn27096, PatFn27096 - Visit87110 - 8/19/2012 9:34PM
PatLn42805, PatFn42805 - Visit86966 - 8/18/2012 11:38PM
PatLn50056, PatFn50056 - Visit86791 - 8/17/2012 8:36PM
PatLn49958, PatFn49958 - Visit86586 - 8/17/2012 12:56AM
PatLn49772, PatFn49772 - Visit86135 - 8/15/2012 5:10PM
PatLn34833, PatFn34833 - Visit85830 - 8/15/2012 1:07AM
PatLn49515, PatFn49515 - Visit85517 - 8/14/2012 9:57PM
PatLn15738, PatFn15738 - Visit85098 - 8/14/2012 9:24AM Start Date :              End Date :

Patient Discharge Status : | Discharged ▼ |

[ Run ]

FIG. 17L

Knowledge Portal

System | Supply Management | Products | Respiratory ▼

Welcome! John Doe | Change Password | Mobile | Help | Sign Out

Home > Executive Summary > Care Area

Data Current as of: August 21, 2012

KPI Detail

Site: IDN0000001 - Hospital01
Kpi: Lung Protection Analytics
View: Care Area

Start Date: August 1, 2012
End Date: August 31, 2012

[Export] [Print]
[Edit Criteria]

⊙ Table View ○ Chart View

Analysis Path: Care Area then Physician then Patient Summary then Patient Details ▶

| Care Area | # of Patients with LP Markers (17292) | Avg Vent Days (17293) | Avg # of Times Outside Threshold (17294) | Avg # of Hours Outside Threshold (17295) | |
|---|---|---|---|---|---|
| SICU | 3 | 1.49 | 8 | 5.9 | Trend |
| MICU | 3 | 10.05 | 5 | 11.6 | Trend |

1 - 2 of 2 items

Site In Analysis:
IDN0000001
Hospital01

Knowledge Portal

System | Supply Management | Products | Respiratory ▼

Welcome! John Doe | Change Password | Mobile | Help | Sign Out

Home > Executive Summary > Care Area

Data Current as of: August 21, 2012

Site In Analysis
- IDN0000001
- Hospital01

KPI Detail [Export] [Print]

Site: IDN0000001 - Hospital01
Kpi: Alarm Setting Analytics
View: Care Area

Start Date: August 1, 2012
End Date: August 31, 2012

[Edit Criteria]

⊙ Table View  ○ Chart View

Analysis Path: Care Area then Physician then Patient Summary then Patient Details ▶

| Care Area | # of Patients with Alarm Setting Markers (17341) | Avg Vent Days (17293) | Avg # of Times Outside Threshold (17294) | Avg # of Hours Outside Threshold (17295) | % of Time Outside Threshold (17342) | |
|---|---|---|---|---|---|---|
| SICU | 4 | 3.89 | 15 | 84.9 | 91.0 | Trend |
| MICU | 8 | 5.34 | 25 | 122.4 | 95.5 | Trend |

1 - 2 of 2 items

Knowledge Portal

Hospital01
Weaning Summary Report
Generation Date : 11/16/2012

| Patient Name | Account ID | Attending Physician | Admission Date Time | Discharge Date Time | Discharge Status | Care Area | Time on Ventilator* (dd:hh:mm) | Time To First Weaning Criteria (dd:hh:mm) | Time From Weaning to First SBT (dd:hh:mm) | Time From Weaning to Final Extubation (dd:hh:mm) | Reintubated |
|---|---|---|---|---|---|---|---|---|---|---|---|
| PatLn06788, PatFn06788 | Visit84741 | DocLn00180, DocFn00180 | 8/20/2012 6:53 AM | NA | No | SICU | 0:12:47 | 0:11:59 | 0:0:-46 | | No |
| PatLn08313, PatFn08313 | Visit84493 | DocLn00057, DocFn00057 | 8/9/2012 1:39 PM | NA | No | ICU | 5:23:12 | 0:1:53 | 0:21:14 | | No |
| PatLn15738, PatFn15738 | Visit85098 | DocLn00074, DocFn00074 | 8/12/2012 5:51 AM | NA | No | ICU | 0:14:44 | 0:1:0 | 0:-1:0 | | Yes |
| PatLn27096, PatFn27096 | Visit87110 | DocLn00066, DocFn00066 | 8/19/2012 8:16 PM | NA | No | MICU | 1:21:32 | 1:15:10 | | | No |
| PatLn34833, PatFn34833 | Visit85830 | DocLn00005, DocFn00005 | 8/14/2012 8:05 PM | NA | No | MICU | 6:15:53 | 0:1:0 | 0:6:30 | | No |
| PatLn36865, PatFn36865 | Visit79283 | DocLn00032, DocFn00032 | 7/23/2012 11:07 AM | NA | No | SICU | 13:15:50 | 0:18:7 | | | No |
| PatLn37199, PatFn37199 | Visit83262 | DocLn00067, DocFn00067 | 8/5/2012 2:45 PM | 8/13/2012 8:21 PM | Yes | ICU | 0:8:39 | 0:1:0 | 0:4:59 | 0:7:39 | No |
| PatLn40088, PatFn40088 | Visit71506 | DocLn00180, DocFn00180 | 6/25/2012 5:29 AM | 8/18/2012 10:55AM | Yes | MICU | 0:0:33 | 0:8:5 | 0:4:38 | 53:2:33 | No |
| PatLn40273, PatFn40273 | Visit83353 | DocLn00135, DocFn00135 | 8/6/2012 8:39 AM | 8/15/2012 2:30 PM | Yes | ICU | 0:19:37 | 0:1:0 | 0:18:52 | 0:19:0 | No |
| PatLn42589, PatFn42589 | Visit84988 | DocLn00005, DocFn00005 | 8/11/2012 5:54 AM | 8/14/2012 10:49 AM | Yes | SICU | 3:2:0 | 0:1:0 | 1:23:10 | 3:1:1 | No |
| PatLn42805, PatFn42805 | Visit86966 | DocLn00121, DocFn00121 | 8/18/2012 2:10 PM | NA | No | ICU | 0:14:12 | 0:1:26 | 0:11:26 | | No |
| PatLn43051, PatFn43051 | Visit71305 | DocLn00120, DocFn00120 | 6/22/2012 2:22 AM | NA | No | ICU | 4:3:49 | 0:2:38 | 0:21:49 | | No |

| Care Area | # of Weaning Candidates | Avg Vent Days | Avg Hours to First Weaning Marker | Avg Hours from First Weaning Marker to First SBT | Avg Hours from First Weaning Marker to final Extubation | Reintubation Rate (%) | Total Est. Vent Cost for Patients with Weaning Markers | Avg Est. Vent Cost Patients with Weaning Markers |
|---|---|---|---|---|---|---|---|---|
| SICU | 13 | 2.52 | 2.5 | 23.5 | 50.8 | 7.7 | $89,332.75 | $6,871.75 |
| MICU | 16 | 4.32 | 7.9 | 35.0 | 59.3 | 0.0 | $212,285.81 | $13,267.86 |

Knowledge Portal

System  Supply Management  Products  | Respiratory ▼ |

Welcome! John Doe | Change Password | Mobile | Help | Sign Out

Home > Executive Summary > Care Area > Physician

Data Current as of : August 21, 2012

Site In Analysis
IDN0000001 ▼
Hospital01 ▼

KPI Detail  [Export] [Print]
Site: IDN0000001 - Hospital01
Kpi: Weaning Analytics
View: Care Area (SICU) then Physician                              [Edit Criteria ✎]

Start Date: August 1, 2012
End Date: August 31, 2012

◉ Table View ○ Chart View      Analysis Path [Care Area then Physician then Patient Summary then Patient Details ▼]

17208 →

| Care Area | Physician 17291 | # of Weaning Candidates 17254 | Avg Vent Days 17255 | Avg Hours to First Weaning Marker 17371 | Avg Hours from First Weaning Marker to First SBT 17372 | Avg Hours from First Weaning Marker to final Extubation 17373 | Reintubation Rate (%) 17374 | Total Est. Vent Cost for Patients with Weaning Markers 17375 |
|---|---|---|---|---|---|---|---|---|
| SICU | DocLn00120, DocFn00120 | 3 | 1.59 | 1.4 | 5.7 | 5.2 | 0.0 | $11,081.05 |
| SICU | DocLn00067, DocFn00067 | 1 | 0.36 | 1.0 | 5.0 | 7.7 | 0.0 | $806.12 |
| SICU | DocLn00057, DocFn00057 | 1 | 5.97 | 1.9 | 21.2 | 141.3 | 0.0 | $16,648.70 |
| SICU | DocLn00066, DocFn00066 | 1 | 10.82 | 1.3 | 41.5 | | 0.0 | $35,645.19 |
| SICU | DocLn00005, DocFn00005 | 1 | 3.08 | 1.0 | 47.2 | 73.0 | 0.0 | $6,894.85 |
| SICU | DocLn00074, DocFn00074 | 1 | 1.87 | 1.0 | | 72.4 | 100.0 | $4,181.34 |

Knowledge Portal

Hospital01
Weaning Details Report
Generation Date : 11/8/2012

Patient Name : PatLn36865, PatFn36865 MRN : MRNOO36865 Age : 56y 6m 21d Gender : Female
Admission Date Time : 7/23/2012 11:07 AM Last Care Area : SICU Discharge Date Time : NA

| Event Category ⇕ (17401) | Event Type ⇕ (17402) | Event Date ⇕ Time (17403) | Value ⇕ (17404) | Min ⇕ Value (17405) | Max ⇕ Value (17406) | Unit of ⇕ Measure (17407) |
|---|---|---|---|---|---|---|
| Hourly Summary | FiO2 | 8/21/2012 7:00 PM | 55 | 55 | 56 | % |
| Hourly Summary | Minute Ventilation | 8/21/2012 7:00 PM | 14.1462 | 12.31 | 15.8 | L |
| Hourly Summary | PEEP | 8/21/2012 7:00 PM | 4 | 4 | 5 | cmH2O |
| Hourly Summary | Spontaneous Tidal Volume | 8/21/2012 7:00 PM | 0 | 0 | 0 | mL |
| Hourly Summary | Total Rate | 8/21/2012 7:00 PM | 25 | 22 | 29 | bpm |
| Hourly Summary | Work of Breathing Measured | 8/21/2012 7:00 PM | 2.00125 | 1.93 | 2.05 | joules/L |
| Weaning Analytics | Weaning Candidate - No SBT Attempt | 8/21/2012 6:03 PM | | | | |
| Hourly Summary | FiO2 | 8/21/2012 6:00 PM | 55 | 55 | 56 | % |
| Hourly Summary | Minute Ventilation | 8/21/2012 6:00 PM | 13.4827 | 11.62 | 16.25 | L |
| Hourly Summary | PEEP | 8/21/2012 6:00 PM | 4 | 4 | 5 | cmH2O |
| Hourly Summary | Spontaneous Tide Volume | 8/21/2012 6:00 PM | 0 | 0 | 0 | mL |
| Hourly Summary | Total Rate | 8/21/2012 6:00 PM | 25 | 23 | 29 | bpm |
| Hourly Summary | Work of Breathing Measured | 8/21/2012 6:00 PM | 2.0239 | 1.89 | 2.18 | joules/L |
| Hourly Summary | FiO2 | 8/21/2012 5:00 PM | 55 | 55 | 56 | % |
| Hourly Summary | Minute Ventilation | 8/21/2012 5:00 PM | 12.8812 | 11.09 | 15 | L |
| Hourly Summary | PEEP | 8/21/2012 5:00 PM | 4 | 4 | 5 | cmH2O |
| Hourly Summary | Spontaneous Tidal Volume | 8/21/2012 7:00 PM | 0 | 0 | 0 | mL |
| Hourly Summary | Total Rate | 8/21/2012 5:00 PM | 25 | 23 | 29 | bpm |
| Hourly Summary | Work of Breathing Measured | 8/21/2012 5:00 PM | 2.05633 | 1.92 | 2.16 | joules/L |
| Hourly Summary | FiO2 | 8/21/2012 4:00 PM | 59 | 55 | 61 | % |

Knowledge Portal  Welcome! John Doe | Change Password | Mobile | Help | Sign Out System  Supply Management  Products  | Respiratory ▼ |

Home >Ventilator Settings Report

Ventilator Settings Report : Select parameters

Select Admissions (Patient Name - AccountID - Ventilator Start Time)

```
PatLn50445, PatFn50445 - Visit87574 - 8/21/2012 6:27PM
PatLn50397, PatFn50397 - Visit87472 - 8/21/2012 12:38PM
PatLn50365, PatFn50365 - Visit87416 - 8/21/2012 1:52AM
PatLn06788, PatFn06788 - Visit84741 - 8/20/2012 9:17PM
PatLn50242, PatFn50242 - Visit87146 - 8/20/2012 6:49AM
PatLn27096, PatFn27096 - Visit87110 - 8/19/2012 9:34PM
PatLn42805, PatFn42805 - Visit86966 - 8/18/2012 11:38PM
PatLn50056, PatFn50056 - Visit86791 - 8/17/2012 8:36PM
PatLn49958, PatFn49958 - Visit86586 - 8/17/2012 12:56AM
PatLn49772, PatFn49772 - Visit86135 - 8/15/2012 5:10PM
PatLn34833, PatFn34833 - Visit85830 - 8/15/2012 1:07AM
PatLn49515, PatFn49515 - Visit85517 - 8/14/2012 9:57PM
PatLn15738, PatFn15738 - Visit85098 - 8/14/2012 9:24AM
```
⟨ 17421

17422
Start Date : [    ]    End Date : [    ]

[Run]  ✽

FIG. 17W

3500 monitor patient orientation of a patient, wherein the patient is associated with a ventilator
3510 capture images of the patient.
3512 monitor patient orientation based on accelerometers attached to the patient
3514 monitor patient orientation based on accelerometers attached to a mask
3516 periodically monitor patient orientation
3518 modifying ventilator operation of the ventilator based on the patient orientation
3520 increase an amount of fresh gas to the patient
3522 modify a protocol of the ventilator
3524

```
access use of ventilator consumables
4010 access use of ventilator consumables by a health care facility ventilation
    management system
    4012
```

↓

```
manage ventilation inventory based on the use of ventilator consumables
4020 reorder the ventilator consumables
    4022
```

```
store the use of ventilator consumables
4030
```

FIG. 40

RESPIRATORY KNOWLEDGE PORTAL

CROSS-REFERENCE TO RELATED U.S. APPLICATIONS

The present application claims the benefit of priority under 35 U.S.C. § 120 as a continuation from U.S. patent application Ser. No. 13/756,421 entitled "Respiratory Knowledge Portal," filed on Jan. 31, 2013, which is a continuation-in-part from U.S. patent application Ser. No. 13/538,834 entitled "Ventilator Suction Management," filed on Jun. 29, 2012, which is related to each of U.S. patent application Ser. No. 13/287,419 entitled "Bi-Directional Ventilator Communication," filed on Nov. 2, 2011,U.S. patent application Ser. No. 13/287,490 entitled "Contextualizing Ventilator Data," filed on Nov. 2, 2011, U.S. patent application Ser. No. 13/287,876 entitled "Ventilator Component Module," filed on Nov. 2, 2011, U.S. patent application Ser. No. 13/287,935 entitled "Automatic Implementation of a Ventilator Protocol," filed on Nov. 2, 2011, U.S. patent application Ser. No. 13/287,972 entitled "Implementing Ventilator Rules on a Ventilator," filed on Nov. 2, 2011, U.S. patent application Ser. No. 13/287,572 entitled "Healthcare Facility Ventilation Management," filed on Nov. 2, 2011, U.S. patent application Ser. No. 13/287,752 entitled "Wide Area Ventilation Management," filed on Nov. 2, 2011, U.S. patent application Ser. No. 13/287,993, entitled "Analyzing Medical Device Data," filed on Nov. 2, 2011, U.S. patent application Ser. No. 13/287,995 entitled "Ventilator Report Generation," filed on Nov. 2, 2011, U.S. patent application Ser. No. 13/288,000 entitled "Suggesting Ventilator Protocols," filed on Nov. 2, 2011, U.S. patent application Ser. No. 13/288,013 entitled "Ventilation Harm Index," filed on Nov. 2, 2011, U.S. patent application Ser. No. 13/287,981 entitled "Ventilator Avoidance Report," filed on Nov. 2, 2011, U.S. patent application Ser. No. 13/288,006 entitled "Assisting Ventilator Documentation at a Point of Care," filed on Nov. 2, 2011, U.S. patent application Ser. No. 13/538,905 entitled "Remotely Accessing a Ventilator," filed on Jun. 29, 2012, U.S. patent application Ser. No. 13/538,950 entitled "Modifying Ventilator Operation Based on Patient Orientation," filed on Jun. 29, 2012, U.S. patent application Ser. No. 13/538,980 entitled "Logging Ventilator Data," filed on Jun. 29, 2012, U.S. patent application Ser. No. 13/539,024 entitled "Ventilator Billing and Inventory Management," filed on Jun. 29, 2012, and U.S. patent application Ser. No. 13/539,114 entitled "Virtual Ventilation Screen," filed on Jun. 29, 2012, the disclosures of which are hereby incorporated by reference in their entirety for all purposes.

BACKGROUND

Field

The present disclosure generally relates to transmission of data over a network, and more particularly to the use of a computing device to communicate with medical devices over a network.

Description of the Related Art

Medical ventilators (colloquially called "respirators") are machines that are typically used to mechanically move breathable air into and out of lungs in order to assist a patient in breathing. Ventilators are chiefly used in intensive care medicine, home care, emergency medicine, and anesthesia. Common ventilators are limited to a single direction of communication, and as such are configured to provide information related to the ventilator for display, but not receive information from a remote source to control the ventilator. For example, common ventilators send outbound data to another entity, such as a display device, in order to display ventilator settings.

Health care professionals in a health care facility typically need to be in physical proximity to a ventilator (e.g., next to the ventilator) in order to view ventilator information for a patient. It is difficult, however, for health care professionals such as respiratory therapists to be physically near each of many patients the therapist is responsible for in order to monitor the ventilation of each of the patients. Thus, a therapist monitoring a ventilator of one patient is unable to concurrently monitor the ventilator of another patient. As a result, vital health information for a patient on a ventilator may not be seen by the therapist until it is too late, or, in certain circumstances, may never be seen by the therapist. In such circumstances, the health care facility in which the therapist and patients are present may suffer economic loss from inefficient use of ventilators for their patients, or, more importantly, may incur negative health consequences for patients due to an inability to monitor the ventilators of multiple patients with a limited number of therapists.

SUMMARY

According to certain aspects of the present disclosure, a monitoring system for multiple medical ventilators is provided. The monitoring system includes a memory that includes instructions, and a processor. The processor is configured to execute the instructions to receive data for a plurality of medical ventilators, and identify a configuration for each of the plurality of medical ventilators from the received data for the plurality of medical ventilators. The processor is also configured to execute the instructions to associate each patient with a respective one of the plurality of medical ventilators, determine an identification and status for each patient associated with one of the plurality of medical ventilators, and provide, for display, information indicative of the configuration of each of the plurality of medical ventilators and indicative of the identification and status of each patient associated with one of the plurality of medical ventilators.

In certain aspects of the monitoring system, the information indicative of the configuration of each of the plurality of medical ventilators includes at least one of an apnea interval, a bias flow, a compression volume, a $CO_2$ value, a demand flow, a diameter, an average end tidal $CO_2$, a fraction of inspired oxygen ($FiO_2$), a flow cycle, or a flow trigger. The information indicative of the identification and status of each patient can include at least one measured physiological statistic for dynamic compliance (Cdyn), inverse ratio ventilation (I/E), mandatory ventilation rate, mandatory exhaled tidal volume (VTE), total lung ventilation per minute, positive end respiratory pressure (PEEP), peak expiratory flow rate (PEFR), peak inspiratory flow rate (PIFR), mean airway pressure, peak airway pressure, and total ventilation rate. The received data for the plurality of medical ventilators can include a medical ventilator start time, a medical ventilator mode, tidal volume (VT), ventilation frequency, $FiO_2$, and PEEP. The information provided for display can include a notification for at least one patient that indicates at least one of an alert for the medical ventilator associated with the patient, or an alert indicating a non-compliance of the medical ventilator with a compliance policy. Information provided for display can include a total estimated ventilation cost for patients in a first period, a total estimated ventilation cost for patients in a second, baseline period, a total estimated weaning cost for patients in the first period, a total estimated weaning cost for patients in the second period, and a difference in cost between the first period and the second period.

The information provided for display can include a report, for at least one of the patients, of at least one of weaning, medical ventilator settings, medical ventilator history, lung protection, and patient details. The data is received at the monitoring system, and parameters for generating the report are configurable at the monitoring system. The report can include at least one of analytics data or summary data. The report for weaning can include current, minimum, and maximum values for a patient information for at least one of FiO2, minute ventilation, PEEP, VT, total ventilation rate, and work of breathing measured.

The identification for each patient can include at least one of an account identification, a patient name, patient care area, or patient location. The processor can be further configured to transmit a request to at least one of the plurality of medical ventilators, the request can include at least one a request to remotely access the medical ventilator, to remotely control the medical ventilator, to annotate data stored on the medical ventilator, to change information for a patient associated with the medical ventilator, or obtain diagnostic information for the medical ventilator. The data for the plurality of medical ventilators can be received over a network. The received data can include a physiological statistic obtained from the medical ventilator for a patient, and wherein the processor is further configured to receive a threshold value for generating a notification when the physiological statistic for the patient exceeds the threshold value.

The information indicative of the identification and status of each patient can include providing information for patients in a care area indicative of at least one of a number of weaning candidates, average number days on a medical ventilator, average number of hours from a first weaning marker to a first spontaneous breathing trial (SBT), average number of hours from the first weaning marker to a final extubation, a reintubation rate, a total estimated ventilation cost for patients with weaning markers, an average estimated ventilation cost for patients with weaning markers, patient weaning information grouped by physician, a number of patients with alarm notifications, an average number of times patients in the care area have had physiological statistics exceeding acceptable thresholds, or a percentage of time patients in the care area have had physiological statistics exceeding acceptable thresholds. The information for patients in the care area can be provided in at least one of a text format or chart format. The information can be provided for display using an interface configured for a mobile device.

According to certain aspects of the present disclosure, a method for monitoring multiple medical ventilators using a single device is provided. The method includes receiving data for a plurality of medical ventilators, and identifying a configuration for each of the plurality of medical ventilators from the received data for the plurality of medical ventilators. The method also includes associating each patient with a respective one of the plurality of medical ventilators, determining an identification and status for each patient associated with one of the plurality of medical ventilators, and providing, for display, information indicative of the configuration of each of the plurality of medical ventilators and indicative of the identification and status of each patient associated with one of the plurality of medical ventilators.

In certain aspects of the method, the information indicative of the configuration of each of the plurality of medical ventilators includes at least one of an apnea interval, a bias flow, a compression volume, a $CO_2$ value, a demand flow, a diameter, an average end tidal $CO_2$, $FiO_2$, a flow cycle, or a flow trigger. The information indicative of the identification and status of each patient can include at least one measured physiological statistic for dynamic compliance, inverse ratio ventilation, mandatory ventilation rate, VTE, total lung ventilation per minute, PEEP, PEFR, PIFR, mean airway pressure, peak airway pressure, and total ventilation rate. The received data for the plurality of medical ventilators can include a medical ventilator start time, a medical ventilator mode, VT, ventilation frequency, FiO2, and PEEP. The information provided for display can include a notification for at least one patient that indicates at least one of an alert for the medical ventilator associated with the patient, or an alert indicating a non-compliance of the medical ventilator with a compliance policy. Information provided for display can include a total estimated ventilation cost for patients in a first period, a total estimated ventilation cost for patients in a second, baseline period, a total estimated weaning cost for patients in the first period, a total estimated weaning cost for patients in the second period, and a difference in cost between the first period and the second period.

The information provided for display can include a report, for at least one of the patients, of at least one of weaning, medical ventilator settings, medical ventilator history, lung protection, and patient details. The data is received at a device, and wherein parameters for generating the report are configurable at the device. The report can include at least one of analytics data or summary data. The report for weaning can include current, minimum, and maximum values for a patient information for at least one of FiO2, minute ventilation, PEEP, VT, total ventilation rate, and work of breathing measured.

The identification for each patient can include at least one of an account identification, a patient name, patient care area, or patient location. The method can further include transmitting a request to at least one of the plurality of medical ventilators, the request can include at least one a request to remotely access the medical ventilator, to remotely control the medical ventilator, to annotate data stored on the medical ventilator, to change information for a patient associated with the medical ventilator, or obtain diagnostic information for the medical ventilator. The data for the plurality of medical ventilators can be received over a network. The information can be provided for display using an interface configured for a mobile device. The received data can include a physiological statistic obtained from the medical ventilator for a patient, and wherein the method further can include receiving a threshold value for generating a notification when the physiological statistic for the patient exceeds the threshold value.

The information indicative of the identification and status of each patient can include providing information for patients in a care area indicative of at least one of a number of weaning candidates, average number days on a medical ventilator, average number of hours from a first weaning marker to a first SBT, average number of hours from the first weaning marker to a final extubation, a reintubation rate, a total estimated ventilation cost for patients with weaning markers, an average estimated ventilation cost for patients with weaning markers, patient weaning information grouped by physician, a number of patients with alarm notifications, an average number of times patients in the care area have had physiological statistics exceeding acceptable thresholds, or a percentage of time patients in the care area have had physiological statistics exceeding acceptable thresholds. The information for patients in the care area can be provided in at least one of a text format or chart format.

According to a further embodiment of the present disclosure, a machine-readable storage medium includes machine-readable instructions for causing a processor to execute a method for monitoring multiple medical ventilators using a single device is provided. The method includes receiving data for a plurality of medical ventilators, and identifying a configuration for each of the plurality of medical ventilators from the received data for the plurality of medical ventilators. The method also includes associating each patient with a respective one of the plurality of medical ventilators, determining an identification and status for each patient associated with one of the plurality of medical ventilators, and providing, for display, information indicative of the configuration of each of the plurality of medical ventilators and indicative of the identification and status of each patient associated with one of the plurality of medical ventilators.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 35 illustrates an example method for modifying ventilator operation based on patient orientation.

FIG. 40 illustrates an example method for ventilation inventory management.

Figure 1A:
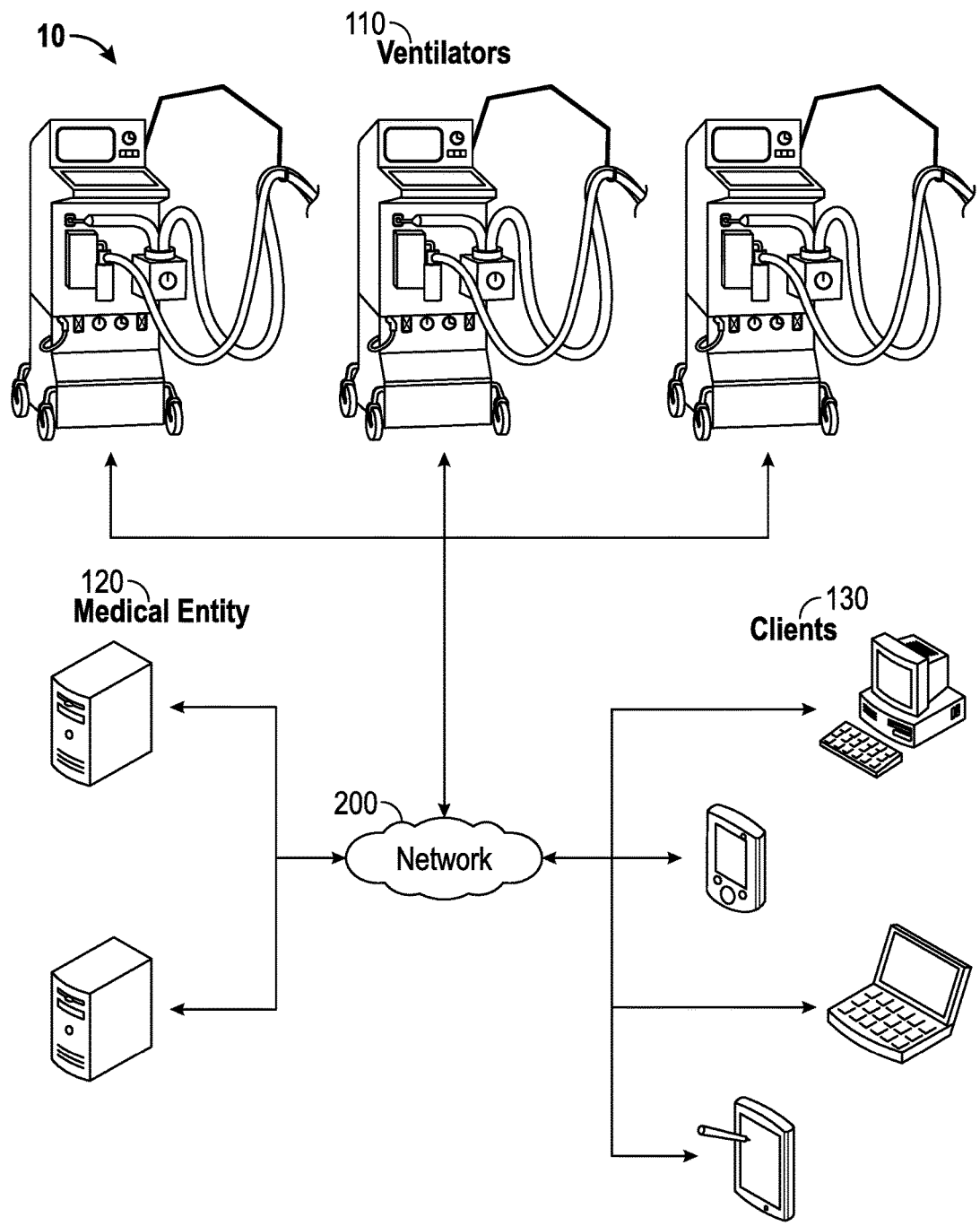
FIG. 1A illustrates an example architecture for transmitting data for multiple medical ventilators over a network.

The drawings referred to in this description should be understood as not being drawn to scale except if specifically noted.

DETAILED DESCRIPTION

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Certain aspects of the disclosed system include a user interface ("ventilator monitoring user interface" or "knowledge portal") for viewing and transmitting information from/to one or many medical ventilators. The ventilator monitoring user interface provides, for example, a view of current patients on a ventilator, ventilator settings, and patient status, and may be beneficial to users such as respiratory therapists, respiratory therapy directors, and healthcare facility quality management. The ventilator monitoring user interface also provides weaning (e.g., the process of taking a patient off of a ventilator) analytics, and detailed data reports for weaning and ventilator settings. In certain aspects, the ventilator monitoring user interface is hosted on a server and accessed over a network, such as by using a web browser. Additionally, in certain aspects, information for the medical ventilators is obtained from a coordination engine or other server hosting data for the medical ventilators. Information provided for display in the ventilator monitoring user interface can be provided by another server that collects information from a ventilator, or directly from a ventilator.

The ventilator monitoring user interface may be configured for viewing on a mobile device, whether through a dedicated application for obtaining information from the ventilator monitoring user interface (e.g., using an application programming interface or "API") or using a general application such as a web browser for accessing the ventilator monitoring user interface. The ventilator monitoring user interface includes security measures, such as ensuring stored data from the ventilators is not modified or corrupted by providing limited read-only access to the stored data and recording a log of access to the stored data. The ventilator monitoring user interface further includes an ability to configure threshold values for physiological statistics (e.g., dynamic compliance, inverse ratio ventilation, mandatory ventilation rate, mandatory exhaled tidal volume, etc.) and for institutional compliance policies, and generating a notification when a threshold value is exceeded. Reports such as patient summary and detail reports, weaning reports, lung protection reports, and other types of ventilator-related reporting can be generated by the ventilator monitoring user interface.

Architecture for Transmitting Data for Medical Ventilators

FIG. 1A illustrates an example architecture 10 for transmitting data for multiple medical ventilators over a network. The architecture 10 includes ventilators 110, medical entities 120, and clients 130 connected over a network 200.

In addition to mechanically moving breathable air into and out of lungs in order to assist a patient in breathing, each of the medical ventilators 110 is configured to monitor physiological statistics for the patient, such as dynamic compliance, inverse ratio ventilation, mandatory ventilation rate, mandatory VTE, total lung ventilation per minute, PEEP, PEFR, PIFR, mean airway pressure, peak airway pressure, and total ventilation rate data. As discussed in further detail below, each ventilator 110 is configured to provide ventilator data indicative of the monitored physiological statistics over the network 200 to one or many of the medical entities 120, which may include servers that store and host the ventilator data. For purposes of load balancing, multiple servers can store and host the ventilator data, either in part or in whole (e.g., replication). The medical entities 120 can be any device having an appropriate processor, memory, and communications capability for storing and hosting the ventilator data. In certain aspects, a medical entity 120 can include a coordination engine for providing the ventilator data in a format usable by other applications, such as third party applications. In certain aspects, a medical entity 120 can be a server with a ventilator monitoring user interface application for accessing stored ventilator data on another medical entity 120.

The ventilator monitoring user interface 125 is configured to receive the stored ventilator data for multiple medical ventilators from a medical entity 120, analyze the ventilator data, and provide the ventilator data for display in a format that is useful to users. For example, the ventilator monitoring user interface 125 can provide summary reports, trend reports, and cost savings analysis for display. Users with appropriate authorization can request additional detail from the ventilators using the ventilator monitoring user interface 125, including providing commands to the ventilators to manage and analyze patients' respiratory care and manage ventilator usage.

The ventilator monitoring user interface 125 can be accessed by clients 130 over the network 200. For example, a user with appropriate authorization can access the ventilator monitoring user interface 125 using, for example, a web browser or a dedicated application on a client 130. The clients 130 can be, for example, desktop computers, mobile computers, tablet computers (e.g., including e-book readers), mobile devices (e.g., a smartphone or PDA), or any other devices having appropriate processor, memory, and communications capabilities for accessing the ventilator monitoring user interface 125 over the network 200. The network 200 can include, for example, any one or more of a personal area network (PAN), a local area network (LAN), a campus area network (CAN), a metropolitan area network (MAN), a wide area network (WAN), a broadband network (BBN), the Internet, and the like. Further, the network 200 can include, but is not limited to, any one or more of the following network topologies, including a bus network, a star network, a ring network, a mesh network, a star-bus network, tree or hierarchical network, and the like.

Bi-Directional Ventilator Communication

Figure 1B:
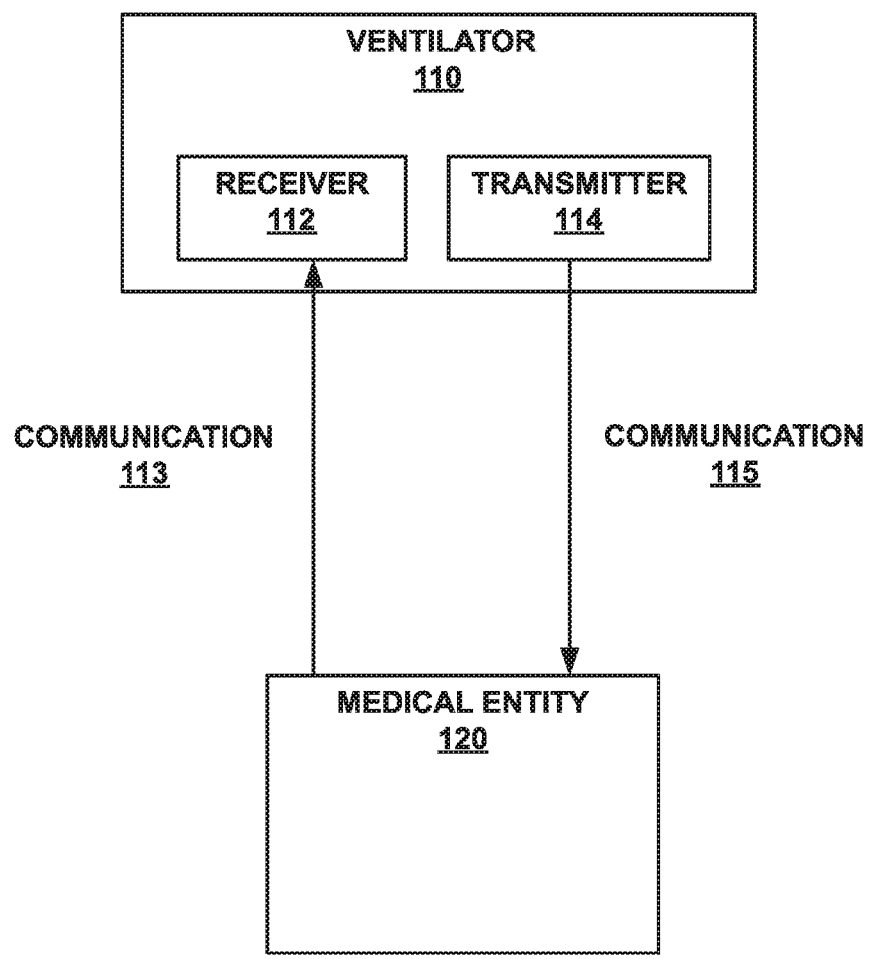
FIG. 1B illustrates an example bi-directional communication system from the architecture of FIG. 1A.

FIG. 1B depicts an example bi-directional communication system 100 between a ventilator 110 and a medical entity 120. In various embodiments, the bi-directional communication is wired or wireless. System 100 includes ventilator 110 and medical entity 120. As depicted, ventilator 110 is able to bi-directionally communicate with medical entity 120. For example, ventilator 110 and medical entity 120 are able to communicate by receiving and transmitting information to one another. In various embodiments, system 100 can include one or more ventilators that are able to bi-directionally communicate with one or more medical entities or other ventilators.

Although system 100 depicts ventilator 110 that is able to bi-directionally communicate with medical entity 120, it should be appreciated other medical devices may be able to bi-directionally communicate with medical entity 120. However, for clarity and brevity, the description below will primarily focus primarily on the structure and functionality of a ventilator.

In general, ventilator 110 can be any medical ventilator configured to provide the mechanism to move breathable air into and out of the lungs of a patient. For example, ventilator 110 can include a compressible air reservoir or turbine, air and oxygen supplies, a set of valves and tubes, and a patient circuit (not shown).

In particular, ventilator 110 also includes receiver 112 and transmitter 114. Receiver 112 is configured for receiving communication 113 from medical entity 120. Receiver 112 can be a wireless receiver configured for receiving a wireless communication. Transmitter 114 is configured for transmitting communication 115 to medical entity 120 or to a plurality of different medical entities. Transmitter 114 can be a wireless transmitter for wirelessly transmitting a communication.

Communication 113, received by ventilator 110, can occur in a variety of forms. For example, communication 113 can include instructions to stream ventilator information, instructions to provide a snapshot of ventilator information, remotely control ventilator 110, instructions to annotate ventilator information, or other instructions. In certain aspects, communication 113 is associated with ventilator manipulation. For example, communication 113 is associated with the manipulation of ventilator functionality (e.g., changing ventilator settings, etc.). In some embodiments, communication 113 affects the functionality of ventilator 110. For example, communication 113 facilitates in the changing of configurations and/or ventilator settings of ventilator 110. Accordingly, communication 113 is not simply a request for ventilator information. As such, communication 113 is not required to be a request for ventilator information.

In certain aspects, communication 115 is transmitted to and stored in medical entity 120. Also, communication may be transmitted from the ventilator 110 and stored separately from medical entity 120, for example, in a database or server. In certain aspects, communication 115 is transmitted directly to medical entity 120. For example, communication 115 is streaming data transmitted directly to a handheld device, which is discussed in further detail below. As such, communication 115 is not stored (or not required to be stored) in a database or server. In certain aspects, the handheld device includes server communication.

Medical entity 120 is able to bi-directionally communicate with ventilator 110 (or other medical devices). In certain aspects, medical entity 120 is a server for a healthcare facility network. In general, a healthcare facility network is a network (or plurality of networks) that facilitates in the management and communication of information regarding medical devices and/or patient care. Bi-directional communication with ventilator 110 can be wireless in the healthcare facility. For example, the wireless bi-directional communication can include 802.11/WiFi for communication using a LAN in the healthcare facility.

In certain aspects, medical entity 120 is a server accessed over a WAN. The bi-directional communication can be wireless over the WAN. For example, medical entity 120 may include a cellular modem to communicate with the WAN, for example, in a home healthcare environment. The WAN can also communicate with a healthcare facility network or a ventilator monitoring user interface 125. It should be appreciated that the WAN can be set up by a third party vendor of ventilators.

In certain aspects, the medical entity 120 can include a server that hosts the ventilator monitoring user interface 125. As described in detail below, the ventilator monitoring user interface 125 is a system that collects and aggregates ventilator information and also provides collective knowledge, predictions, trending, reports, etc. In certain aspects, the ventilator monitoring user interface 125 includes software that is configured to execute on an appropriate device. The software can, for example, include a graphical user interface. In certain aspects, the ventilator monitoring user interface 125 is configured to execute as hardware, for example, instructions hard coded into a processor.

Bi-directional communication (wired or wireless) between ventilator 110 and the ventilator monitoring user interface 125 can be accomplished via a WAN or LAN. For example, the wireless bi-directional communication can include 802.11/WiFi for communication with a LAN or a cellular modem for communication with a WAN, In various embodiments, communication 115 transmitted by ventilator 110 can include, for example, streaming ventilator data or a snapshot of ventilator data. Additionally, communication 113, received by ventilator 110, can include remotely accessing/controlling ventilator 110, annotating ventilator data/information during rounds, etc.

Figure 2:
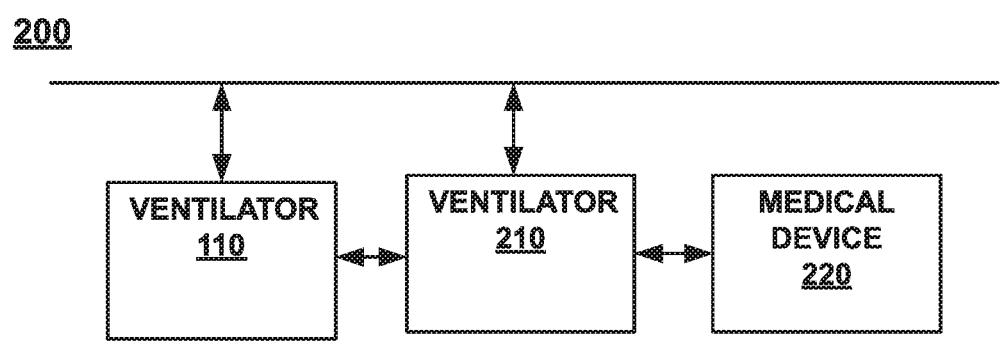
FIG. 2 illustrates an example network of medical devices.

FIG. 2 depicts an example network 200 of medical devices (e.g., ventilators, infusers, $O_2$ sensors, patient orientation sensors, etc.). In particular, network 200 includes ventilators 110 and 210 and medical device 220. It should be understood that network 200 can include any number of a variety of medical devices.

In certain aspects, network 200 is an ad hoc wireless network of medical devices. For example, ventilator 110, 210 and medical device 220 are able to make daisy chain extensions within the range of a LAN or WAN when one wireless personal area network (WPAN) enabled medical device or ventilator is within range of an access point (wired or wireless). In such an example, ventilator 210 utilizes ZigBee or similar 802.15 wireless protocols to connect to network 200 via an access point (not shown). Medical device 220 may not directly connect to the network when medical device 220 is not within range of the access point, but may wirelessly connect with ventilator 210 when medical device 220 is within range of ventilator 210. As such, ventilator 110 and 210 and medical device 220 are able to make a daisy chain extensions within the range of a LAN or WAN. Also, network 200 and associated devices are enabled for automated discovery of other enabled devices and auto setup of the WPAN.

Figure 3:
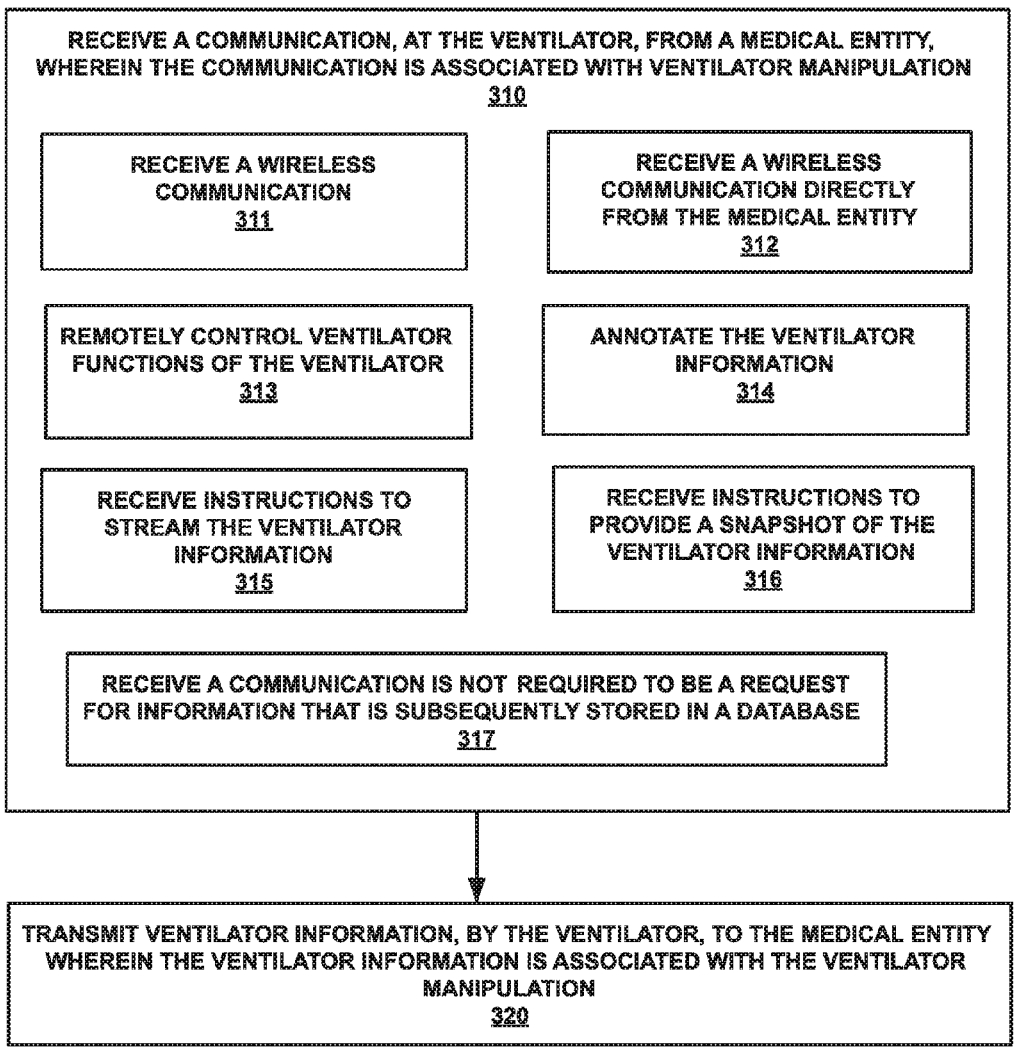
FIG. 3 illustrates an example method for method for bi-directional ventilator communication.

FIG. 3 depicts an example method 300 for method for bi-directional ventilator communication. In various embodiments, method 300 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 300 is performed at least by system 100, as depicted in FIG. 1B.

At step 310 of method 300, a communication is received at the ventilator 110 from a medical entity 210, wherein the communication is associated with ventilator manipulation. For example, ventilator 110 receives communication 113 from medical entity 120. At step 311, a wireless communication is received. For example, ventilator 110 receives a wireless communication from medical entity 120. At step 312, a wireless communication is received directly from the medical entity 120. For example, ventilator 110 receives a wireless communication directly (e.g., without requiring any intermediary communication devices) from a server. At step 313, the ventilator functions are remotely controlled. For example, ventilator functions (e.g., $O_2$ levels, gas supply parameters, ventilator mode, etc.) of ventilator 110 are remotely controlled via medical entity 120. At step 314, ventilator information is annotated. For example, a clinician annotates ventilator information of ventilator 110 in a rounding report via a tablet computer interacting with a server.

At step 315, instructions to stream ventilator information are received. For example, ventilator 110 receives instructions from medical entity 120 to stream ventilator information (e.g., communication 115) such that a clinician is able to view the ventilator information in real-time via a handheld device. At step 316, instructions to provide a snapshot of the ventilator information are received. For example, ventilator 110 receives instructions from medical entity 120 to provide a snapshot of ventilator information such that a clinician is able to view the snapshot of the ventilator information at a handheld device. At step 317, a communication is received that is not required to be a request for information that is subsequently stored in a database. For example, communication 113 is not required to be a request for information that is subsequently stored in database. In such an example, communication 113 can be a request for information that is directly communicated from medical entity 120.

At step 320, ventilator information is transmitted by the ventilator 110 to the medical entity 120. The ventilator information is associated with the ventilator manipulation. For example, transmitter 114 transmits communication 115 that is associated with information regarding the manipulation of ventilator functionality (e.g., confirmation of changed ventilator settings).

Contextualizing Ventilator Data

Figure 4:
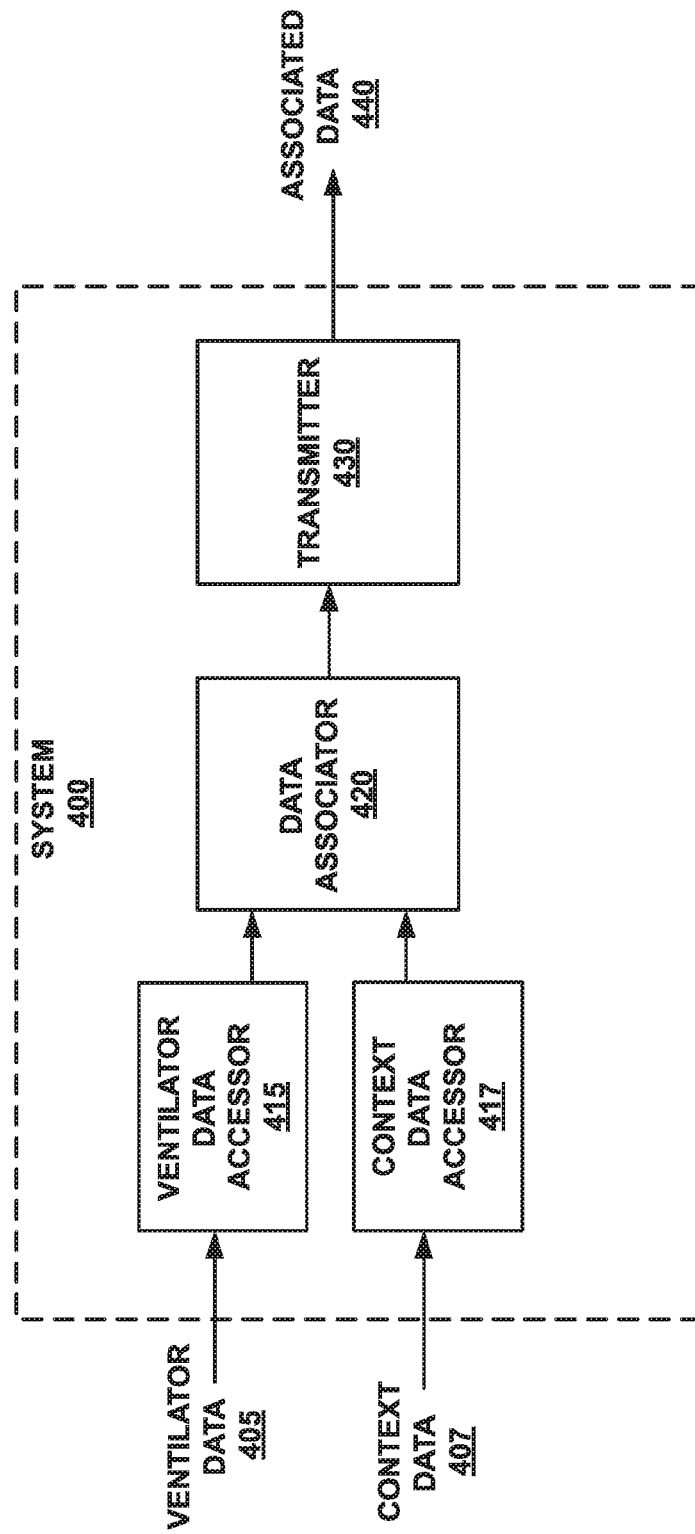
FIG. 4 illustrates an example system for contextualizing ventilator data.

FIG. 4 depicts an embodiment of system 400 for contextualizing ventilator data. System 400 includes ventilator data accessor 415, context data accessor 417, data associator 420 and transmitter 430. Ventilator data accessor 415 is configured for accessing ventilator data 405. Ventilator data 405 can be any information generated by the ventilator 110 or information associated with ventilator functionality regarding patient care. For example, ventilator data 405 can include, but is not limited to, ventilator mode, oxygen level, flow rates, and timing.

Context data accessor 417 is configured for accessing context data 407. Context data 407 can be any information that is able to provide context to ventilator data to enhance patient care via a ventilator. For example, context data 407 can be, but is not limited to, patient identification (ID), ventilator ID, caregiver ID, bed ID, or location. In certain aspects, patient ID is associated with or issued from an Admit, Discharge, Transfer (ADT) system (not shown). As such, the patient ID allows system 400 to acquire additional patient-specific information to be associated with ventilator data 405. The patient-specific information can be, but not limited to, age, sex, height, weight, and treatment information associated with the patient. It should be appreciated that treatment information can be, but is not limited to, surgery, acute care, burn recover, or other treatments. Patient ID can be accessed through patient logon with the ventilator. For example, a patient ID, which may be worn on a wrist of a patient, is scanned and the patient is subsequently logged on to the ventilator 110, and the patient ID is accessed.

Data associator 420 is configured for associating context data 407 and ventilator data 405 such that ventilator data 405 is contextualized. For example, ventilator data 405 includes gas supply parameters and ventilator modes. Context data 407 can include the caregiver ID of the caregiver (e.g., responsible physician or nurse) for the patient associated with the ventilator 110. Accordingly, data associator 420 associates the gas supply parameters and ventilator modes with the caregiver ID. Thus, the gas supply parameters and ventilator modes are contextualized by being associated with the caregiver ID.

In certain aspects, data associator 420 is further configured for associating a subset or a portion of ventilator data 405 with context data 407. For example, ventilator data 405 is associated with a caregiver ID and/or certain operations performed on the ventilator 110. In such an example, the caregiver ID may be accessed locally by scanning the caregiver ID (via a scanner coupled to the ventilator) or remotely such as through remote login (e.g., username/password from the caregiver) with a handheld interface utilized by the caregiver. As a result, ventilator data 405 is associated with the caregiver (e.g., to a caregiver ID), which in turn allows for forwarding of information to a handheld device or other device location. In various embodiments, the caregiver ID is ascertained and/or verified for certain actions such as remote login, accessing certain stored/streaming data, changing certain ventilator settings, implementing an automated protocol, etc.

Transmitter 430 is configured to transmit associated data 440 that is generated by data associator 420. In certain aspects, transmitter 430 is configured to transmit associated data 440 to a handheld device of a caregiver. In various embodiments, associated data 440 (or contextualized data) can be maintained on a ventilator 110 or a server (e.g., a server application).

Figure 5:
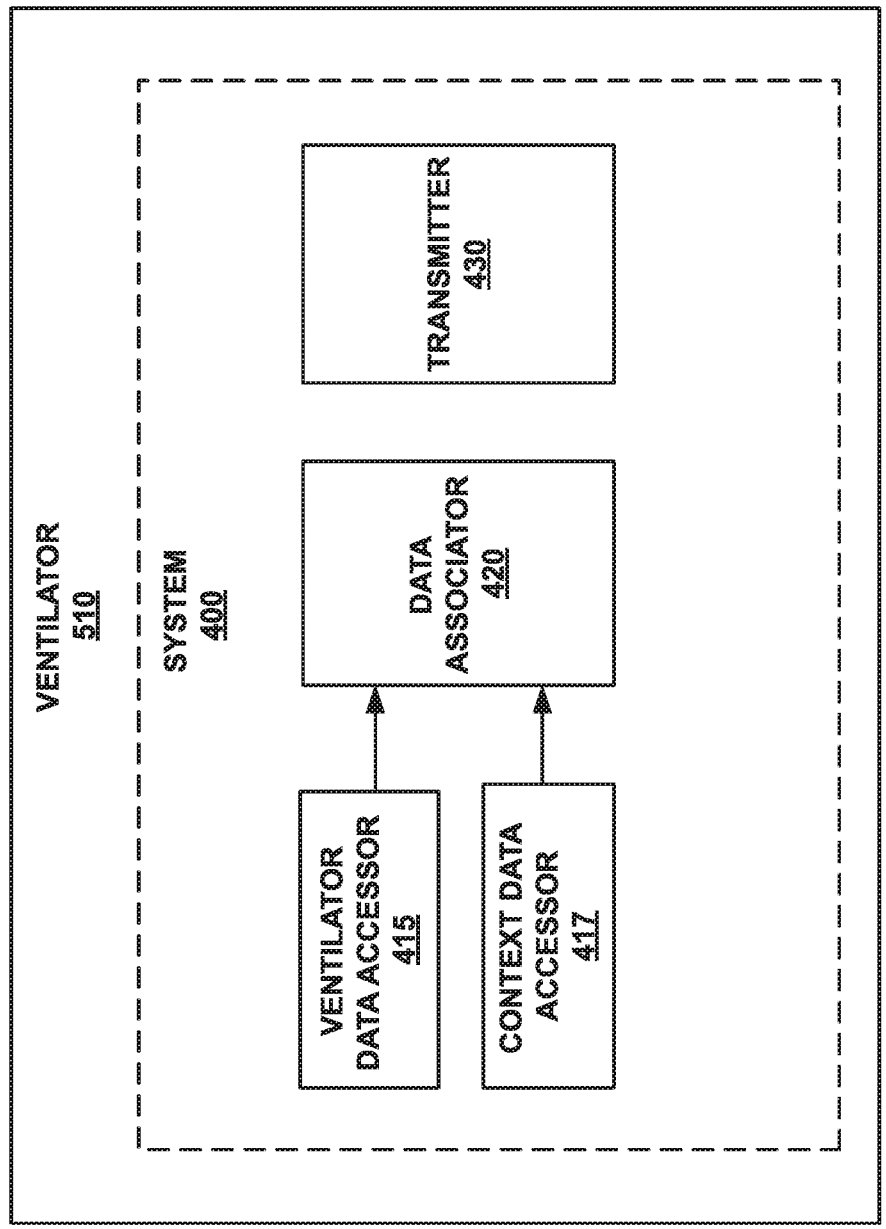
FIG. 5 illustrates an example system for contextualizing ventilator data and a ventilator.

FIG. 5 depicts an embodiment of system 400 disposed in ventilator 510. In certain aspects, ventilator 510 is similar to ventilator 110. It should be understood that system 400 (or some of the components of system 400) may be disposed in another location separate from the ventilator 510. For example, system 400 is disposed in a healthcare facility network or another medical device.

Figure 6:
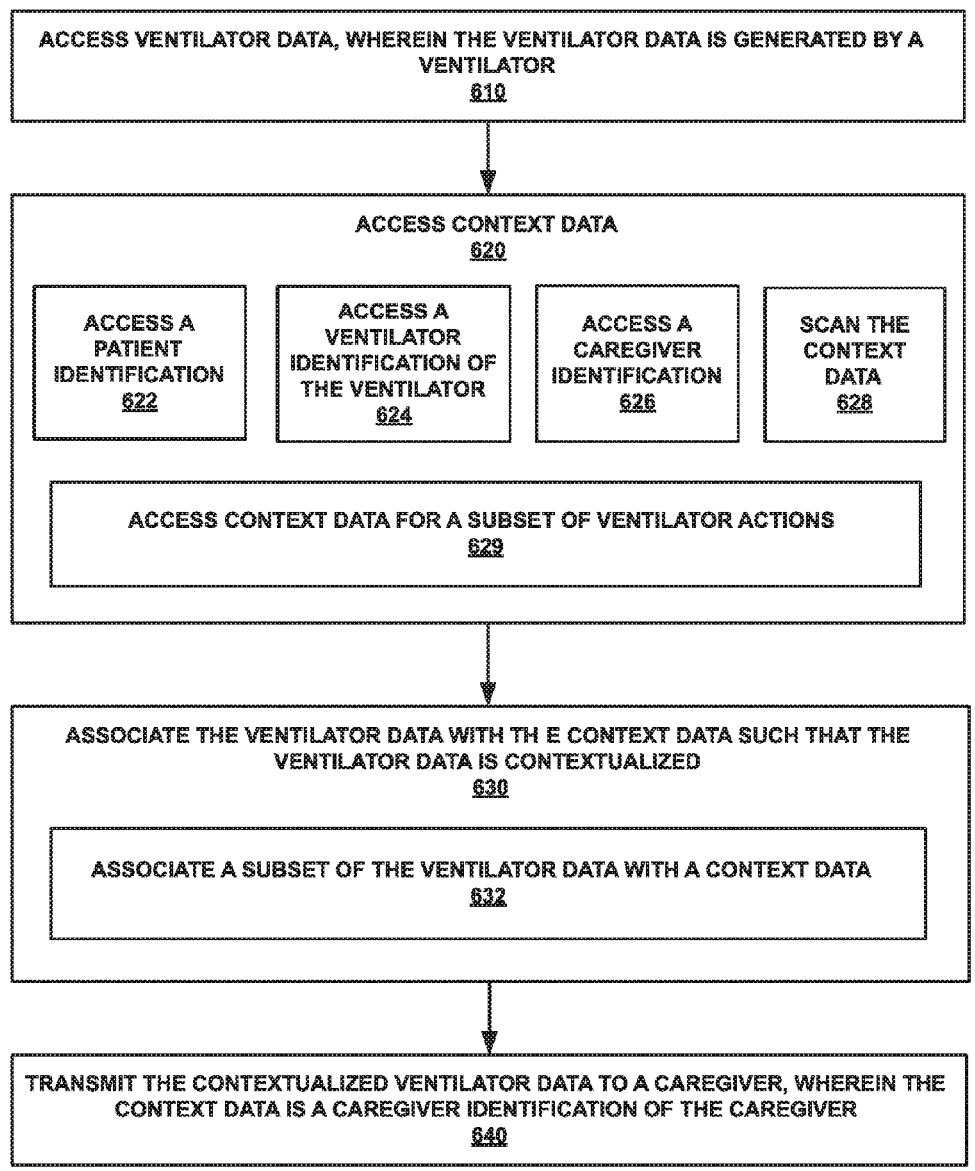
FIG. 6 illustrates an example method for contextualizing ventilator data.

FIG. 6 depicts an example method 600 for contextualizing ventilator data. In various embodiments, method 600 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 600 is performed at least by system 400, as depicted in FIG. 4.

At step 610 of method 600, ventilator data is accessed. The ventilator data is generated by a ventilator 510. For example, ventilator data 405 is accessed by ventilator data accessor 415, and ventilator data 405 is generated by ventilator 510. At step 620, context data is accessed. For example, context data 407 is accessed by context data accessor 417. At step 622, a patient ID is accessed. For example, a patient wristband is scanned to access a patient ID or any other unique patient information (e.g., age, sex, height, weight, etc.). At step 624, a ventilator ID is accessed. For example, a ventilator ID of ventilator 510 is accessed for contextualizing ventilator data 405. At step 626, a caregiver ID is accessed. For instance, a caregiver ID (or any other unique caregiver information) is accessed to facilitate in contextualizing ventilator data 405. As a result, associated data 440 is transmitted to a handheld device utilized by the caregiver. At step 628, context data is scanned. For example, a caregiver ID is scanned in order to access the caregiver ID. In another example, context data is scanned via auto ID technology (e.g., bar codes, radio frequency identification, fingerprint, etc.). At step 629, context data is accessed for a subset of ventilator actions. For example, a caregiver ID is accessed/verified for certain ventilator actions, such as remote login, storing/streaming data, change certain ventilator settings, etc. At step 630, associate the ventilator data with the context data such that the ventilator data is contextualized. For instance, data associator 420 associates ventilator data 405 and context data 407 to generate associated data 440, such that ventilator data 405$s$ contextualized.

At step 632, a subset of the ventilator data is associated with the context data. For example, ventilator data 405 includes gas supply parameters and ventilator modes for an entire duration that a patient is associated with the ventilator 510. Context data 407 includes a first caregiver ID of a plurality of caregivers for the patient associated with the ventilator 510. Accordingly, data associator 420 associates the gas supply parameters and ventilator modes with the first caregiver ID rather than a second and third caregiver ID for a second and third caregiver for the patient. Thus, a portion or subset of ventilator data 405 is associated with the first caregiver ID. At step 640, the contextualized ventilator data is transmitted to a caregiver, wherein the context data includes a caregiver identification of the caregiver. For example, associated data 440 is transmitted to a tablet computer of the caregiver who is responsible for the care of the patient.

Ventilator Component Module

Figure 7:
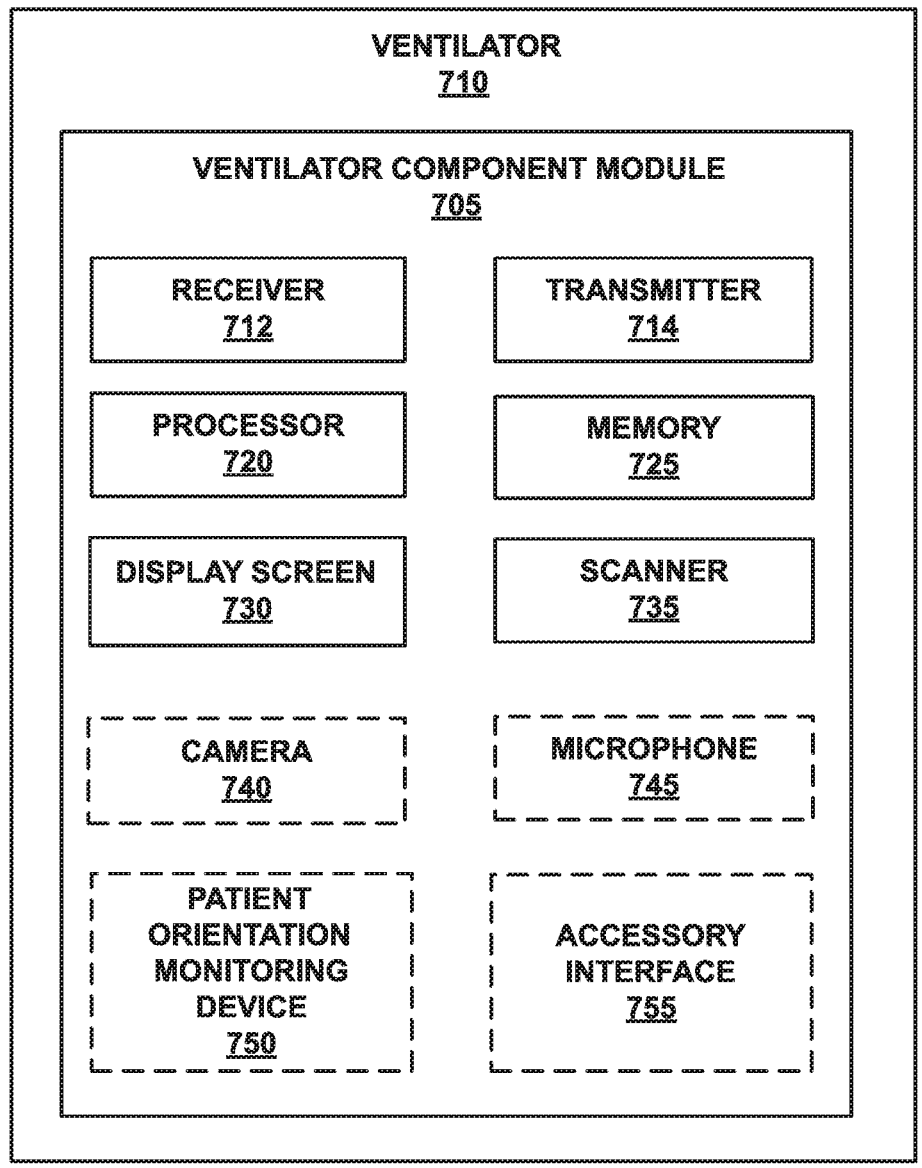
FIGS. 7 and 8 illustrate examples of a ventilator and ventilator component module.

FIG. 7 depicts ventilator 710. In certain aspects, ventilator 710 is similar to ventilator 110, however, ventilator 710 includes ventilator component module 705. Ventilator component module 705 is configured for housing a plurality of ventilator components that are utilized by ventilator 710 to enhance the functionality of ventilator 710. Ventilator component module 705 includes receiver 712, transmitter 714, processor 720, memory 725, display screen 730, scanner 735, and optionally camera 740, microphone 745, patient orientation monitoring device 750, and an accessory interface 755. It should be understood that ventilator component module 705 can include other devices/components that are utilized by ventilator 710 to enhance the functionality of ventilator 710.

Receiver 712 and transmitter 714 are similar to receiver 112 and transmitter 114, respectively, as described above. Processor 720 can be any processor that is configured for processing data, applications, and the like for ventilator 710. Memory 725 is configured for storing ventilator information. For example, memory 725 stores ventilator data 405, context data 407 and/or associated data 440. Display screen 730 is configured for displaying ventilator information. For example, display screen 730 displays a ventilator mode, patient ID, clinician ID, etc. In certain aspects, display screen 730 is a touch screen display that allows access to data on other networked ventilators and/or medical devices. Scanner 735 is any information reader {e.g., bar code reader, RF reader, etc.) that is able to read medical information that is utilized by ventilator 710. For example, scanner 735 is able to scan patient IDs, caregiver IDs, ventilator IDs, and other IDs.

Camera 740 is configured for providing image capture functionality for ventilator 710. For example, camera 740 may capture images of a patient, caregiver, other medical devices to facilitate in the care or security of a patient associated with ventilator 710. Microphone 745 is configured for providing audio capture functionality for ventilator 710. For example, microphone 745 may capture audio data of a patient to facilitate in the care of a patient associated with ventilator 710. Patient orientation monitoring device 750 is configured for monitoring the orientation of a patient associated with ventilator 710. For example, patient orientation monitoring device 750 monitors whether the patient is on his/her side, back stomach, or other position. Accessory interface 755, which may be wired or wireless, is configured to interface other components/devices with ventilator 710. For example, accessory interface 755 includes a Universal Serial Bus (USB) interface for third party accessories (e.g., a video camera).

Figure 8:
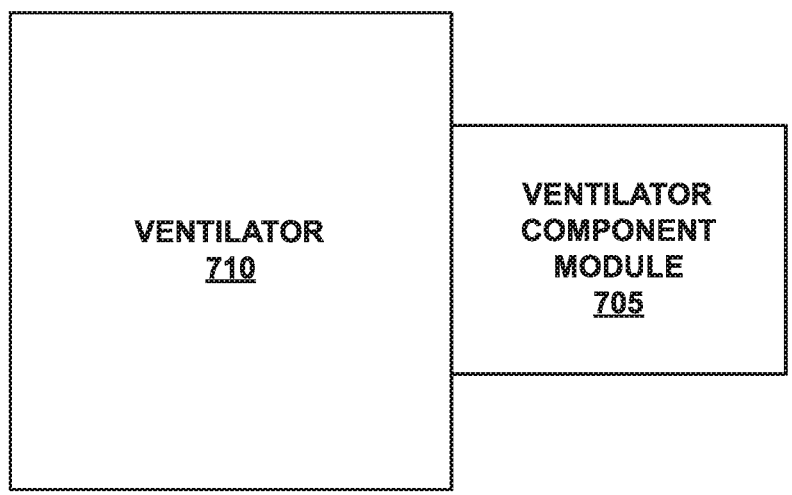

It should be understood that ventilator 710 is operable and provides basic ventilator functionality to provide care for a patient without ventilator component module 705. However, ventilator component module 705 and its respective components enhance the functionality of ventilator 710, as described above. Ventilator component module 705 is disposed within the housing of ventilator 710 or is integral with the housing of ventilator 710. However, ventilator component module 705 may also be releasably attached to ventilator 710, as depicted in FIG. 8. This allows for upgrades to ventilator 710. For example, a version of ventilator component module 705 may easily be swapped out with a new version of ventilator component module 705. Additionally, the releasably attached ventilator component module 705 also facilitates in managing regulatory compliance in the event that some components/functions of the ventilator component module 705 are not immediately approved for patient use.

Automatic Implementation of a Ventilator Protocol

Figure 9:
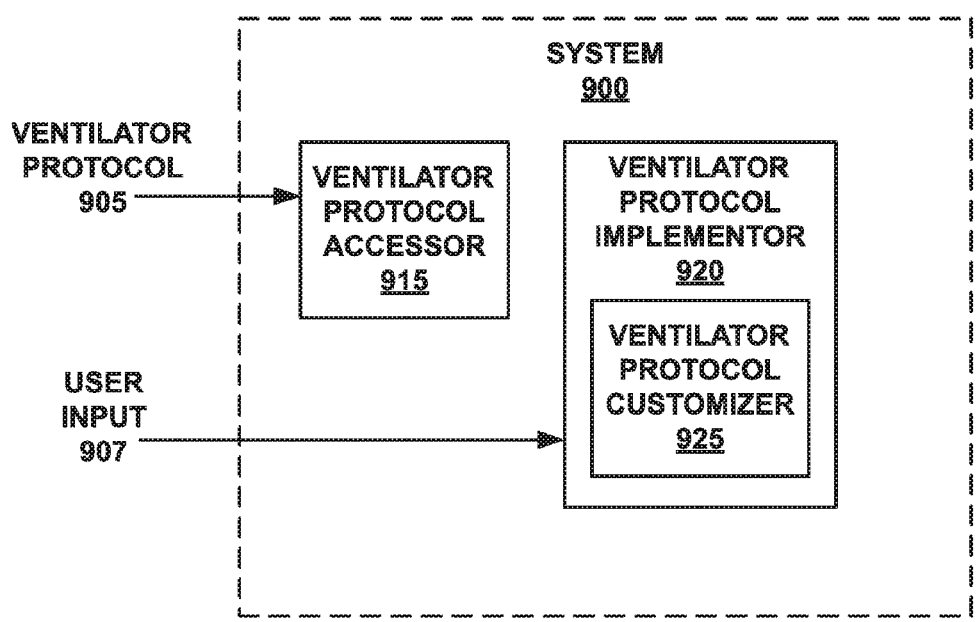
FIG. 9 illustrates an example system for automatically implementing a ventilator protocol.

FIG. 9 depicts an embodiment of system 900 for automatically implementing a ventilator protocol. System 900 includes ventilator protocol accessor 915, ventilator protocol implementor 920, and ventilator protocol customizer 925. System 900 can be disposed in a ventilator, for example, ventilator 710, as described in detail above. System 900 can be implemented in a location separate from the ventilator, for example, in a healthcare facility network.

Ventilator protocol accessor 915 is configured for accessing ventilator protocol 905. Ventilator protocol 905 can be any protocol facilitating in the control of ventilator functionality. For example, ventilator protocol 905 can pertain to oxygen level, flow rate, or timing. In various embodiments, ventilator protocol 905 can be, but is not limited to, a weaning protocol, an acute care protocol, a neonatal $O_2$ protocol, and a lung protection protocol. In certain aspects, a protocol can be described as a decision tree with respect to ventilator control and functionality. In certain aspects, ventilator protocol 905 provides instructions to clinicians on what to do with respect to the ventilator. Ventilator protocol 905 may be native to a ventilator and thus, provided by a ventilator (e.g., ventilator 710). In other embodiments, ventilator protocol 905 may be pushed/accessed from other systems, such as, but not limited to, a hosted (or deployed) user interface or a hospital healthcare system.

Ventilator protocol implementor 920 is configured for implementing ventilator protocol 905 via a touch screen display of a ventilator (e.g., display screen 730). In other words, ventilator protocol implementor 920 is configured to implement ventilator protocol 905 on a ventilator by way of user input 907 at the ventilator. For example, one or more ventilator protocols (e.g., weaning protocol, lung protection protocol, etc.) may be displayed on a touch display screen of a ventilator 710. A caregiver then selects (via the touch display screen) which ventilator protocol is to be implemented on the ventilator 710 for patient care. Accordingly, based on user input 907, ventilator protocol implementor 920 automatically implements the selected ventilator protocol on the ventilator 710. In various embodiments, ventilator protocol 905 is implemented in combination with a medical device, such as an infusion pump. Ventilator protocol 905 can also be controlled or implemented based on patient input. For example, a conscious patient may be able to increase/reduce ventilatory support by self-selection within a protocol-defined range.

Ventilator protocol customizer 925 is configured for customizing ventilator protocol 905. Ventilator protocol customizer 925 can customize ventilator protocol 905 based on unique patient information, for example, a patient ID, patient lab results, patient test results, etc. It should be appreciated that the patient information can be accessed from an ADT system.

Figure 10:
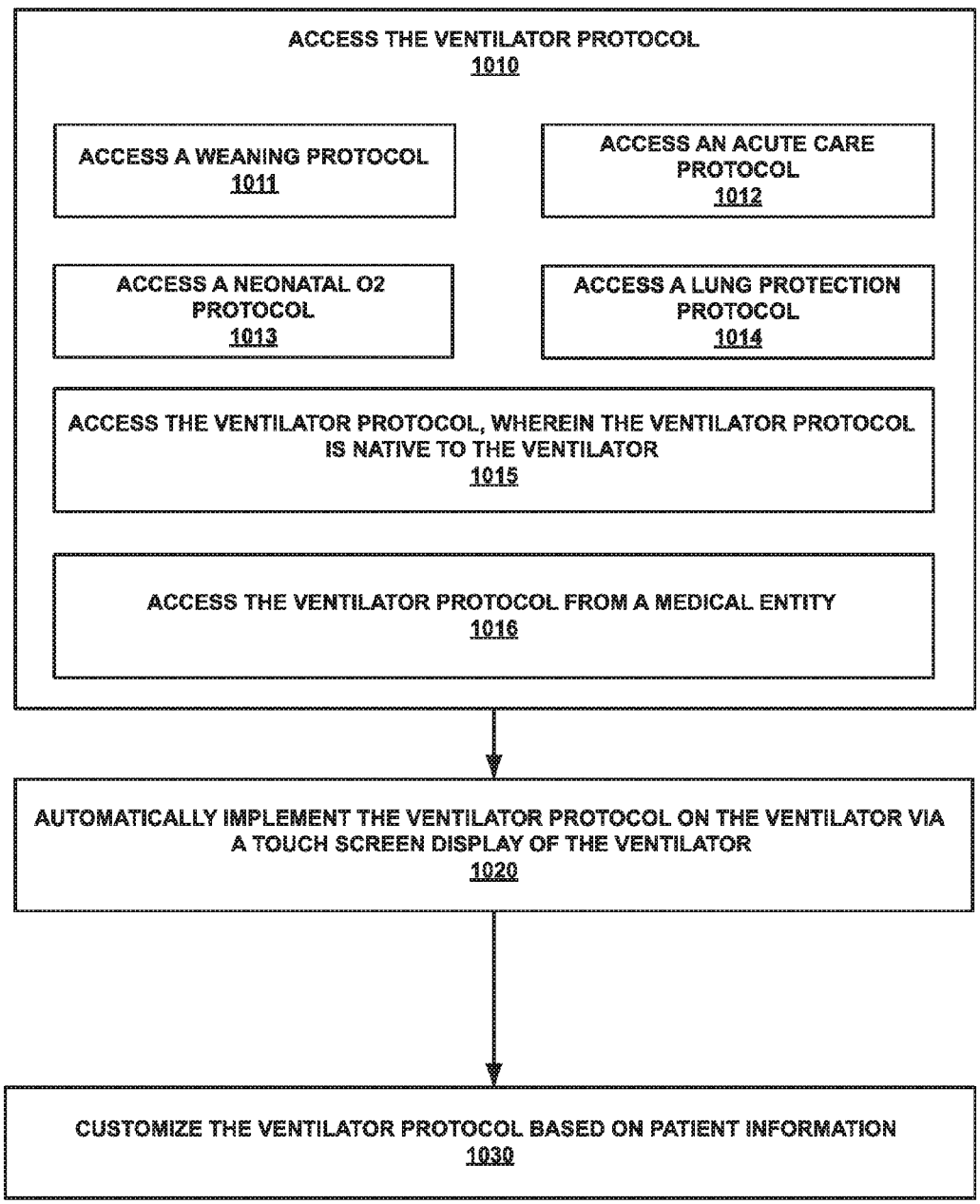
FIG. 10 illustrates an example method for automatically implementing a ventilator protocol.

FIG. 10 depicts an example method 1000 for implementing a ventilator protocol. In various embodiments, method 1000 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1000 is performed at least by system 900, as depicted in FIG. 9.

At step 1010 of method 1000, a ventilator protocol is accessed. For instance, ventilator protocol 905 is accessed by ventilator protocol accessor 915. At step 1011 a weaning protocol is accessed, at step 1012 an acute care protocol is accessed, and at step 1013 a neonatal O2 protocol is accessed. In certain aspects, a lung protection protocol is also accessed. At step 1015, the ventilator protocol is accessed, wherein the ventilator protocol is native to the ventilator. For example, ventilator protocol 905 native to ventilator 710 is accessed. At step 1016, the ventilator protocol is accessed from a medical entity. For example, ventilator protocol 905 is accessed from medical entity 120. At step 1020, the ventilator protocol 905 on the ventilator 710 is automatically implemented via a touch screen display of the ventilator. For example, a caregiver selects a protocol displayed on a display screen. Accordingly, ventilator protocol implementor 920 automatically implements the selected protocol on the ventilator 710. At step 1030, the ventilator protocol 905 is customized based on patient information. For example, ventilator protocol customizer 925 customizes ventilator protocol 905 based on patient lab results.

Implementing Ventilator Rules on a Ventilator

Figure 11:
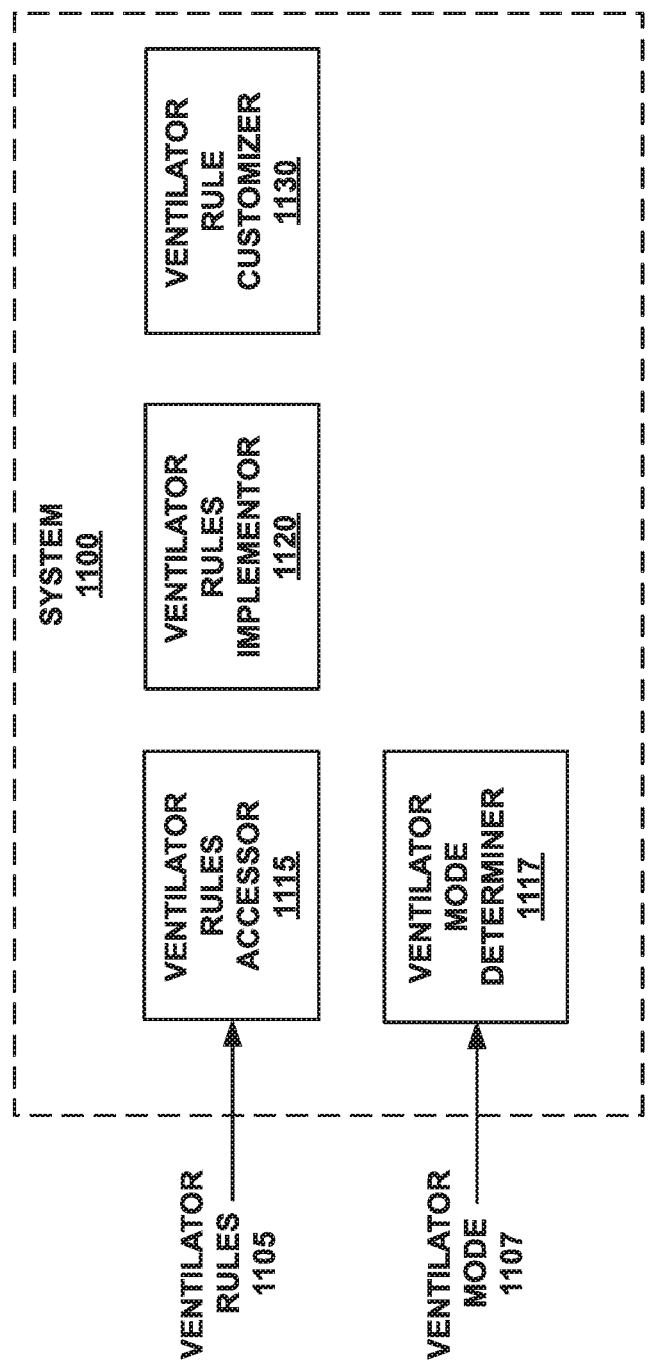
FIG. 11 illustrates an example system for implementing a ventilator rule on a ventilator.

FIG. 11 depicts an embodiment of system 1100 for implementing a ventilator rule on a ventilator 710. System 1100 includes ventilator rule accessor 1115, ventilator mode determiner 1117, ventilator rules implementor 1120, and ventilator rules customizer 1130. System 1100 can be disposed in a ventilator, for example, ventilator 710. System 1100 can be implemented in a location separate from the ventilator 710, for example, in a healthcare facility network.

Ventilator rules accessor 1115 is configured for accessing ventilator rules 1105 for a ventilator 710. Ventilator rules 1105 can be any rule that affects the functionality of a ventilator 710. For example, ventilator rules 1105 can be, but are not limited to, ventilator function control and gas supply parameters, such as, gas flow rates, etc. In certain aspects, ventilator rules 1105 can be a subset of a protocol. For example, if a certain protocol is implemented, then particular rules associated with that specific protocol can be utilized. In certain aspects, ventilator rules 1105 are not associated or part of a protocol. For example, the rule that a warning appears when a battery is dead is not associated with a protocol.

In certain aspects, ventilator rules 1105 are native to a ventilator (e.g., ventilator 710), thus, ventilator rules 1105 are provided by the ventilator 710. In certain aspects, ventilator rules 1105 are accessed from a location, other than the ventilator, for example, from a healthcare facility network (e.g., for local rules) or from a user interface (e.g., for best practice rules). Ventilator mode determiner 1117 is configured to determine which mode(s) the ventilator 710 is operating in. For example, a ventilator mode can be, but is not limited to, a pediatric ventilation mode. Depending on the determined ventilator mode of operation, a variety of rules can be displayed on a display screen of the ventilator 710 and/or certain features can be disabled to prevent patient harm, which will be described in further detail below.

Ventilator rules implementor 1120 is configured for implementing at least one of the ventilator rules 1105 in response to a determined mode of operation. For example, if the ventilator 710 is in a pediatric ventilation mode, certain rules pertaining to gas supply may be implemented. In certain aspects, if a certain rule is implemented, then certain ventilator functions may be locked out, such as certain gas supply parameters to prevent patient harm. If a certain rule is desired to be implemented, then a specific override may be required to in order to implement the desired rule. This would prevent unintentionally interrupting the implementation of the rule. For example, if a ventilator 710 is running in accordance to a first rule, and a second rule is intended to be implemented which conflicts with the first rule, then an override of the second rule may be required.

Ventilator rule customizer 1130 is configured to customize ventilator rules 1105. In certain aspects, ventilator rules 1105 are customized based on patient contextualized data (e.g., age, sex, weight). For example, maximum and minimum fresh gas flow may be customized based on age, sex or weight of a patient. Customization can take place within the ventilator or may be pushed to the ventilator from an outside device/location.

Figure 12:
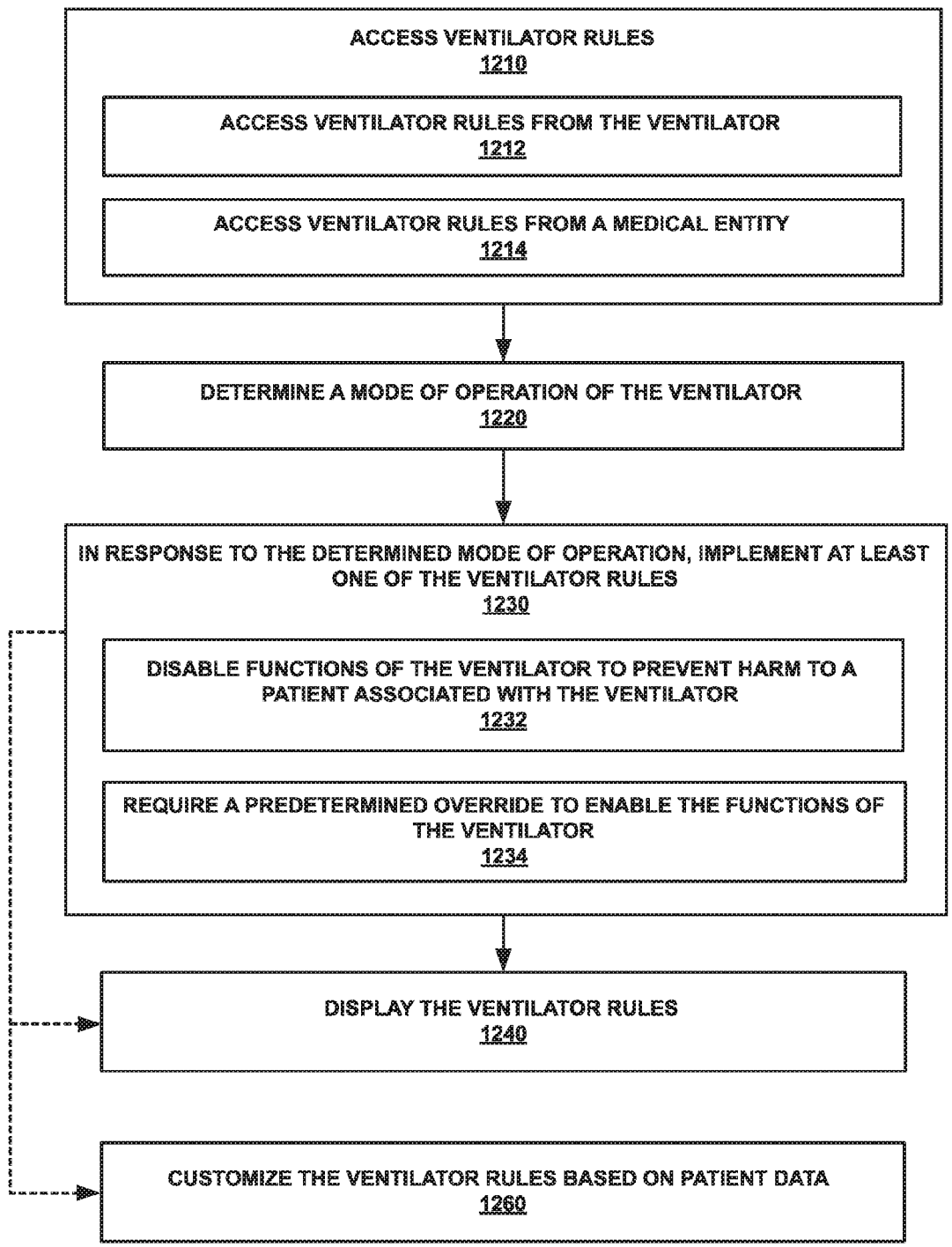
FIG. 12 illustrates an example method for implementing a ventilator rule on a ventilator.

FIG. 12 depicts an example method 1200 for implementing a ventilator protocol. In various embodiments, method 1200 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1200 is performed at least by system 1100, as depicted in FIG. 11.

At step 1210 of method 1200, ventilator rules are accessed. For example, ventilator rules accessor 1115 accesses a plurality of rules that affect gas flow rates and ventilator function control. At step 1212, ventilator rules are accessed from a ventilator. For example, ventilator rules 1105 are accessed from the ventilator 710. In certain aspects, at 1214, ventilator rules are accessed from a medical entity 120, such as a server that includes a ventilator monitoring user interface 125. At step 1220, a mode of operation of the ventilator 710 is determined. For example, ventilator mode determiner 1117 determines that ventilator mode 1107 is a neonatal ventilator mode. At step 1230, in response to the determined mode of operation, at least one of the ventilator rules implemented. For example, ventilator rules implementor 1120 implements a particular max/min flow rate in response to a neonatal ventilation mode.

At step 1232, ventilator functions are disabled to prevent harm to a patient associated with the ventilator 710. For example, certain gas supply functions are disabled to prevent patient harm in response to a determined mode of operation. At step 1234, a predetermined override is required to enable the functions of the ventilator 710. For example, if a ventilator function is disabled, then a predetermined override is required to enable the disabled functions of the ventilator 710. At step 1240, the ventilator rules are displayed. For example, ventilator rules 1105 are displayed on a display screen. At step 1250, ventilator rules are customized based on patient data. For example, ventilator rule customizer 1130 customizes ventilator rules 1105 based on patient age, sex, height, etc.

Healthcare Facility Ventilation Management

Figure 13:
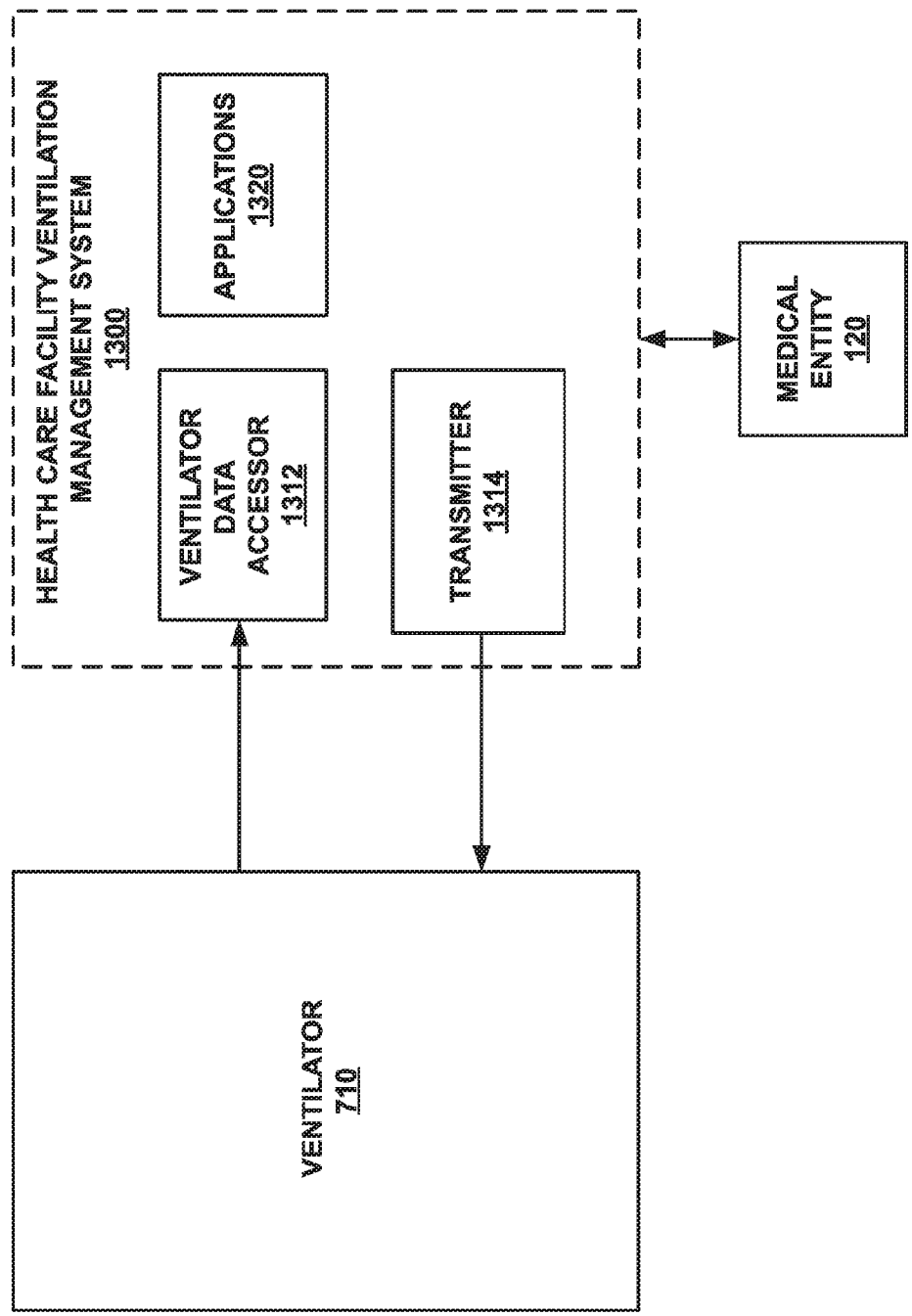
FIG. 13 illustrates an example healthcare facility ventilation management system.

FIG. 13 depicts an embodiment of healthcare facility ventilation management system 1300. System 1300 is associated with a healthcare facility network and is configured to bi-directionally communicate with one or more ventilators (e.g., 710) and/or one or more medical entities (e.g., medical entity 120). The bi-directional communication of system 1300 is similar to the bi-directional communication as described above. In various embodiments, the bi-directional communication is wired or wireless (e.g., 802.11 WiFi) bi-directional communication. In certain aspects, system 1300 is implemented (or runs on) ventilator 710.

In particular, system 1300 includes ventilator data accessor 1312, transmitter 1314 and applications 1320. Ventilator data accessor 1312 is configured for accessing ventilator data from the ventilator 710 (or any other ventilators and/or medical devices). For example, data (e.g., logged in ventilator 710 or streamed from the ventilator 710) is remotely accessed. Transmitter 1314 is configured for transmitting a communication/data to a ventilator and/or a medical entity, which will be described in further detail below. In certain aspects, transmitter 1314 transmits ADT information to a ventilator.

Applications 1320 are any application that is utilized by system 1300 for ventilation management. For example, applications 1320 (or other systems described herein), can be, but are not limited to, a billing application, an inventory control application, cost avoidance application, remote access application, harm avoidance application, protocol application and a rules customization application. It is understood that applications 1320 are related to the variety of systems described herein. As such, system 1300 includes and/or utilizes a plurality of systems and functions described herein. In certain aspects, system 1300 includes and utilizes batch data management. For example, batches of data are able to be sent from a ventilator without real-time communication.

In certain aspects, system 1300 utilizes system 400 for contextualizing ventilator data, which is described in detail above. In such an example, data associator 420 associates context data 407 and ventilator data 405 such that ventilator data 405 is contextualized. Additionally, transmitter 1314 transmits the contextualized data to medical entity 120 (e.g., a server including a ventilator monitoring user interface 125). In certain aspects, system 1300 utilizes system 900 for automatically implementing a ventilator protocol, as described in detail above. For example, ventilator protocol implementor 902 implements a protocol on a ventilator by way of user input at the ventilator. Furthermore, ventilator protocol customizer 925 customizes ventilator a protocol based on unique patient information, such as a patient ID, patient lab results, or patient test results. It should be understood that the protocols are pushed to the ventilator from system 1300, for example, by transmitter 1314.

In certain aspects, system 1300 utilizes system 1100 for implementing a ventilator rule on a ventilator 710, as described in detail above. For example, ventilator rules implementor 1120 implements at least one of the ventilator rules 1105 in response to a determined mode of operation. In such an example, if the ventilator 710 is in a pediatric ventilation mode, certain rules pertaining to gas supply may be implemented. Furthermore, ventilator rules 1105 are customized based on patient contextualized data (e.g., age, sex, weight). For example, maximum and minimum fresh gas flow may be customized based on age, sex or weight of a patient. It should be understood that the rules are pushed to the ventilator from system 1300, for example, by transmitter 1314. It should be appreciated that rules and protocols can result in the ventilator 710 performing an action automatically (e.g., closed loop) or in user guidance (e.g., open loop).

Figure 14:
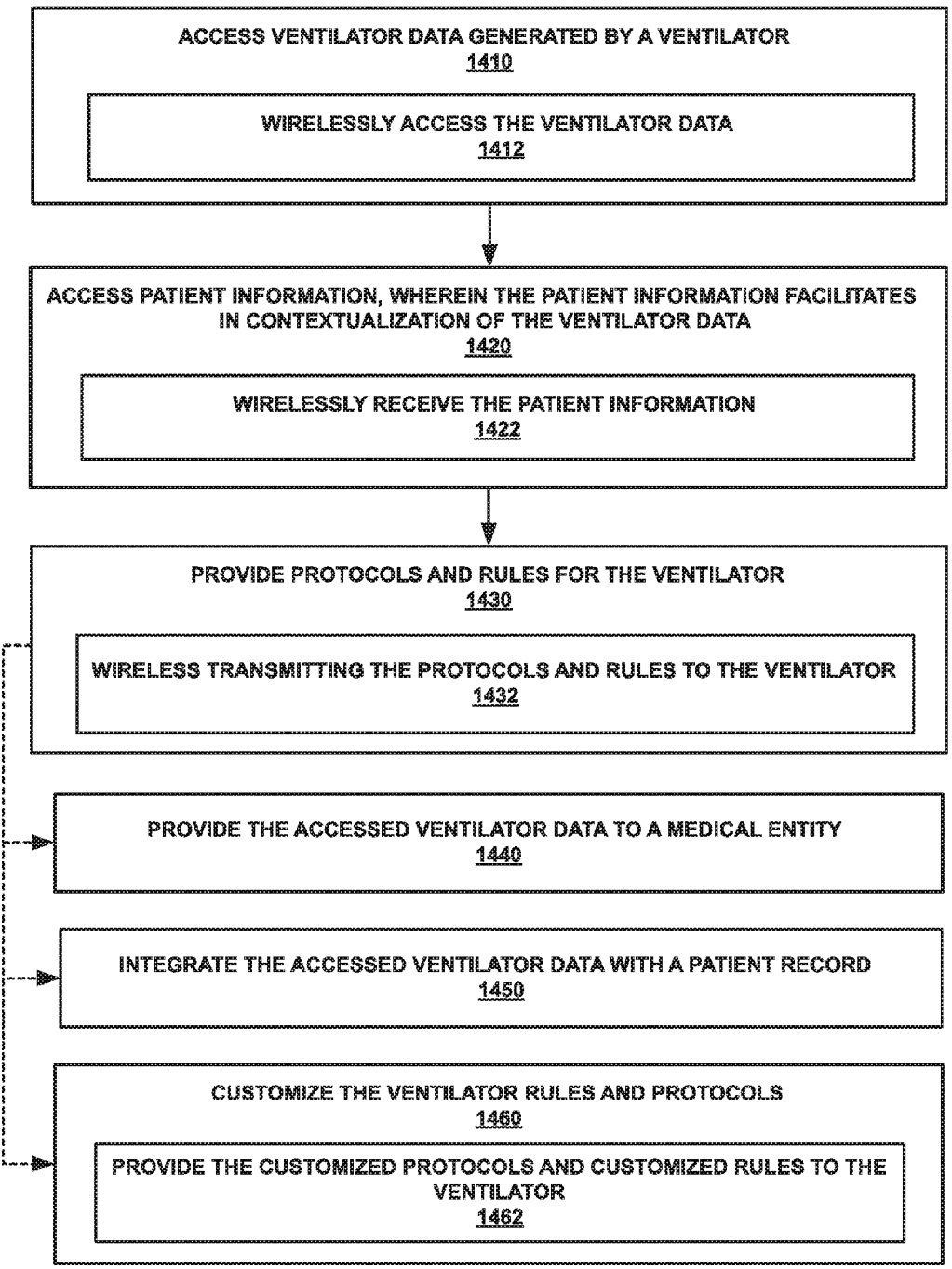
FIG. 14 illustrates an example method for healthcare facility ventilation management.

FIG. 14 depicts an example method 1400 for healthcare facility ventilation management. In various embodiments, method 1400 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1400 is performed at least by system 1300, as depicted in FIG. 13.

At step 1410 of method 1400, ventilator data generated by a ventilator is accessed. For example, ventilator data accessor 1312 accesses ventilator data from the ventilator 710. At step 1412, the ventilator data is wirelessly accessed. For example, ventilator data accessor 1312 wirelessly accesses ventilator data from the ventilator 710 via 802.11 WiFi. At step 1420, patient information is accessed, wherein the patient information facilitates in contextualization of the ventilator data. For example, context data (e.g., age, sex, height, etc.) is accessed. At step 1422, the patient information is wirelessly received. For example, context information is wirelessly received from a medical entity (e.g., medical entity 120). At step 1430, protocols and rules are provided for the ventilator 710. For example, ventilator protocol implementor 902 implements a protocol on a ventilator 710 by way of user input at the ventilator 710 and ventilator rules implementor 1120 implements at least one of the ventilator rules 1105 in response to a determined mode of operation. In certain aspects, the protocols and rules are wirelessly transmitted to the transmitter. At step 1440, accessed ventilator data is provided to a medical entity 120. For example, transmitter 1314 transmits the ventilator data to a handheld device associated with a medical entity 120.

At step 1450, the accessed ventilator data is integrated with a patient record. For example, ventilator data is integrated with unique patient information such that the ventilator data is contextualized. At step 1460, the ventilator rules and protocols are customized. For example, ventilator rule customizer 1130 customizes ventilator rules 1105 based on patient lab results, medications prescribed, etc. In certain aspects, at 1462, the customized protocols and rules are provided to the ventilator (e.g., ventilator 710).

Wide Area Ventilation Management

Figure 15:
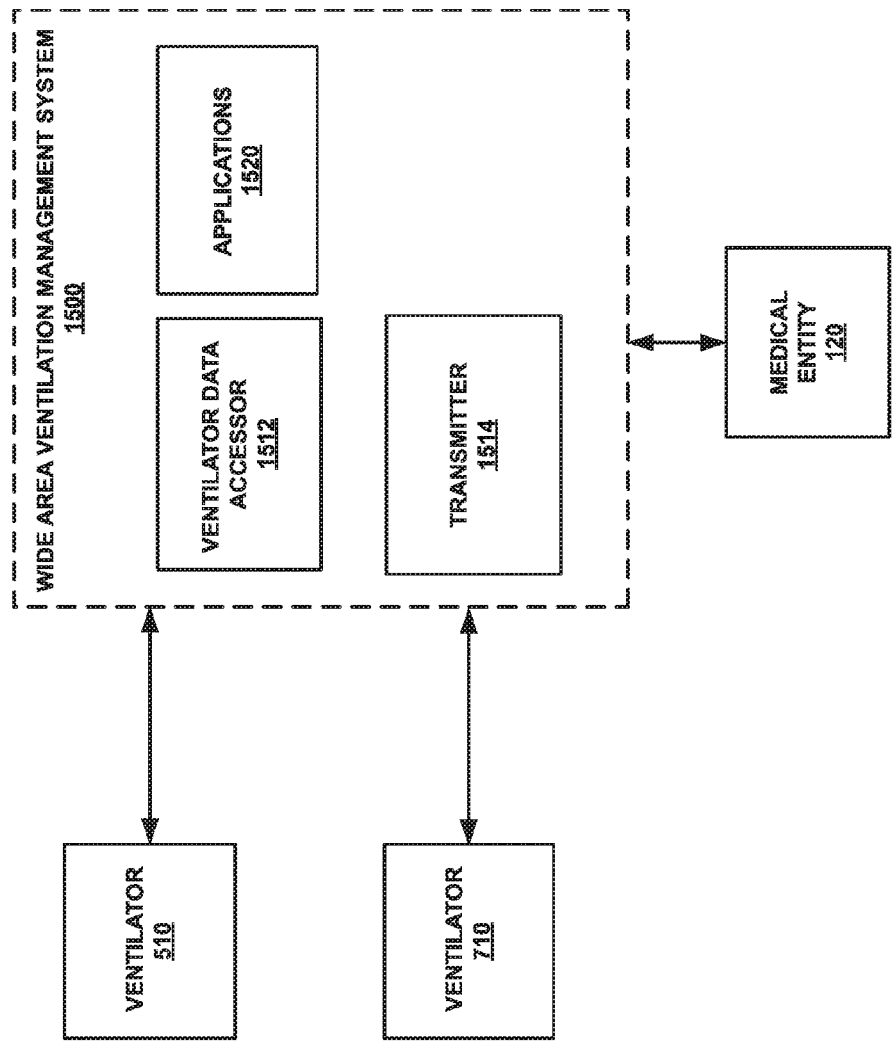
FIG. 15 illustrates an example wide area ventilation management system.

FIG. 15 depicts an embodiment of wide area ventilation management system 1500. System 1500 is associated with a wide area network and is configured to bi-directionally communicate with one or more ventilators (e.g., ventilator 710) and/or one or more medical entities (e.g., medical entity 120). The bi-directional communication of system 1500 is similar to the bi-directional communication as described above. In certain aspects, wireless bi-directional communication is provided via a cellular network.

System 1500 includes ventilator data accessor 1512, transmitter 1514 and applications 1520. Ventilator data accessor 1512 is configured for accessing ventilator data from the ventilators 510 and/or 710 (or any other ventilators and/or medical devices). For example, data (e.g., logged in ventilator 710 or streamed from the ventilator) is remotely accessed. Transmitter 1514 is configured for transmitting a communication/data to ventilators and/or a medical entity 120, which will be described in further detail below. In certain aspects, transmitter 1514 transmits ADT information (or other data) to a ventilator 710. In various embodiments, transmitter 1514 transmits data to a healthcare facility network to facilitate monitoring patient outcomes after they have been discharged. Additionally, data may be transmitted (or received) in a particular Electronic Medication Administration Record (eMAR) format (e.g., level 7 compatible interface).

Applications 1520 are any application that is utilized by system 1500 for ventilation management. For example, applications 1520 (or other systems described herein), can be, but are not limited to, a billing application, an inventory control application, cost avoidance application, remote access application, harm avoidance application, protocol application and a rules customization application. It is understood that applications 1520 are related to the variety of systems described herein. As such, system 1500 includes and/or utilizes a plurality of systems and functions described herein. In certain aspects, system 1500 utilizes system 400 for contextualizing ventilator data, which is described in detail above. In such an example, data associator 420 associates context data 407 and ventilator data 405 such that ventilator data 405 is contextualized. Additionally, transmitter 1514 transmits the contextualized data to medical entity 120 (e.g., a medical entity's handheld device, ventilator monitoring user interface 125, etc.).

In certain aspects, system 1500 utilizes system 900 for automatically implementing a ventilator protocol, as described in detail above. For example, ventilator protocol implementor 902 implements a protocol on a ventilator 710 by way of user input at the ventilator 710. Furthermore, ventilator protocol customizer 925 customizes a ventilator protocol based on unique patient information, for example, a patient ID, patient lab results, or patient test results. It should be understood that the protocols are pushed to the ventilator 710 from system 1500, for example, by transmitter 1514.

In certain aspects, system 1500 utilizes system 1100 for implementing a ventilator rule on a ventilator 710, as described in detail above. For example, ventilator rules implementor 1120 implements at least one of the ventilator rules 1105 in response to a determined mode of operation. In such an example, if the ventilator 710 is in a pediatric ventilation mode, certain rules pertaining to gas supply may be implemented. Furthermore, ventilator rules 1105 are customized based on patient contextualized data (e.g., age, sex, weight). For example, maximum and minimum fresh gas flow may be customized based on age, sex, or weight of a patient. It should be understood that the rules are pushed to the ventilator 710 from system 1500, for example, by transmitter 1514.

Figure 16:
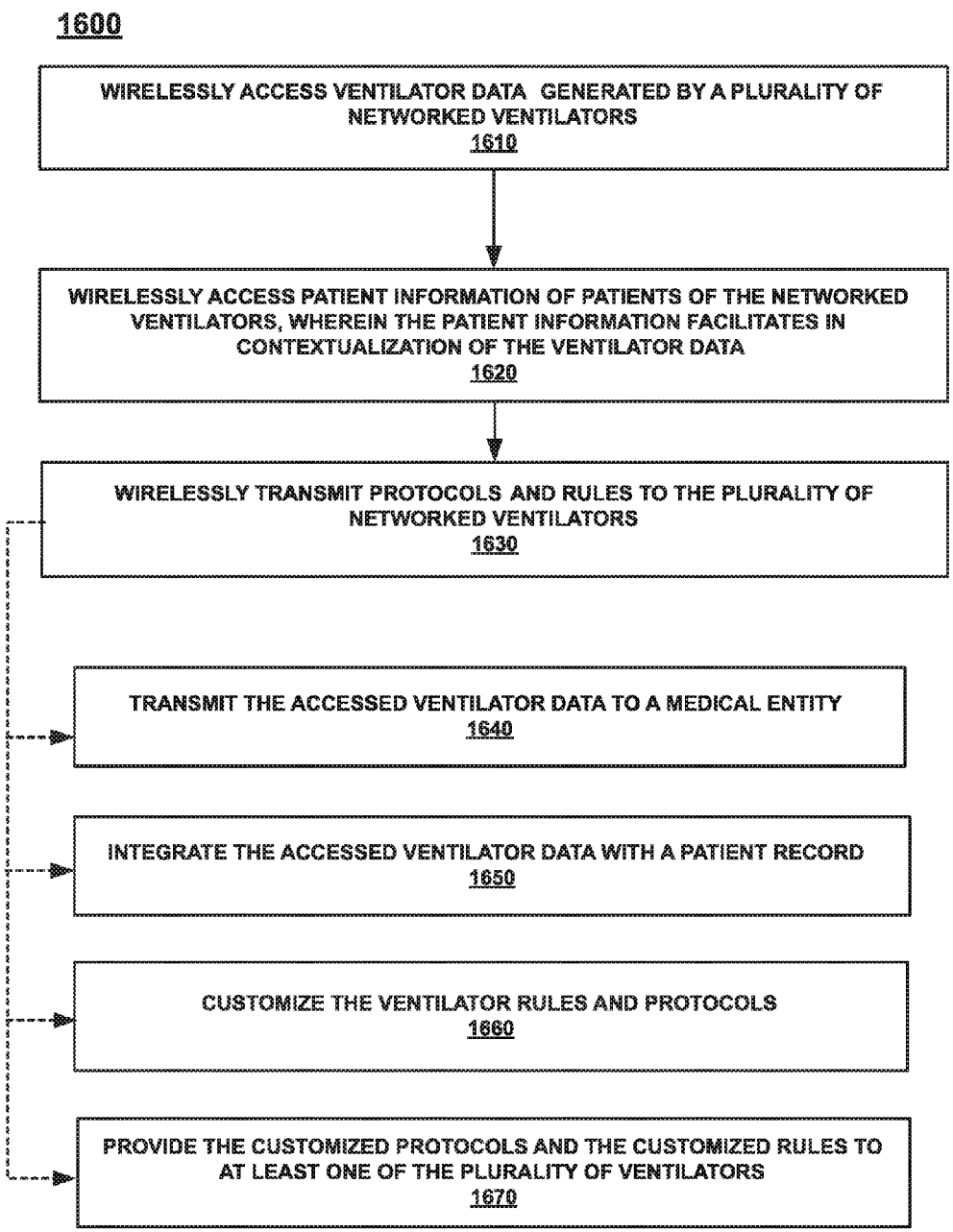
FIG. 16 illustrates an example method for wide area ventilation management.

FIG. 16 depicts an example method 1600 for wide area ventilation management. In various embodiments, method 1600 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1600 is performed at least by system 1500, as depicted in FIG. 15.

Figure 17A:
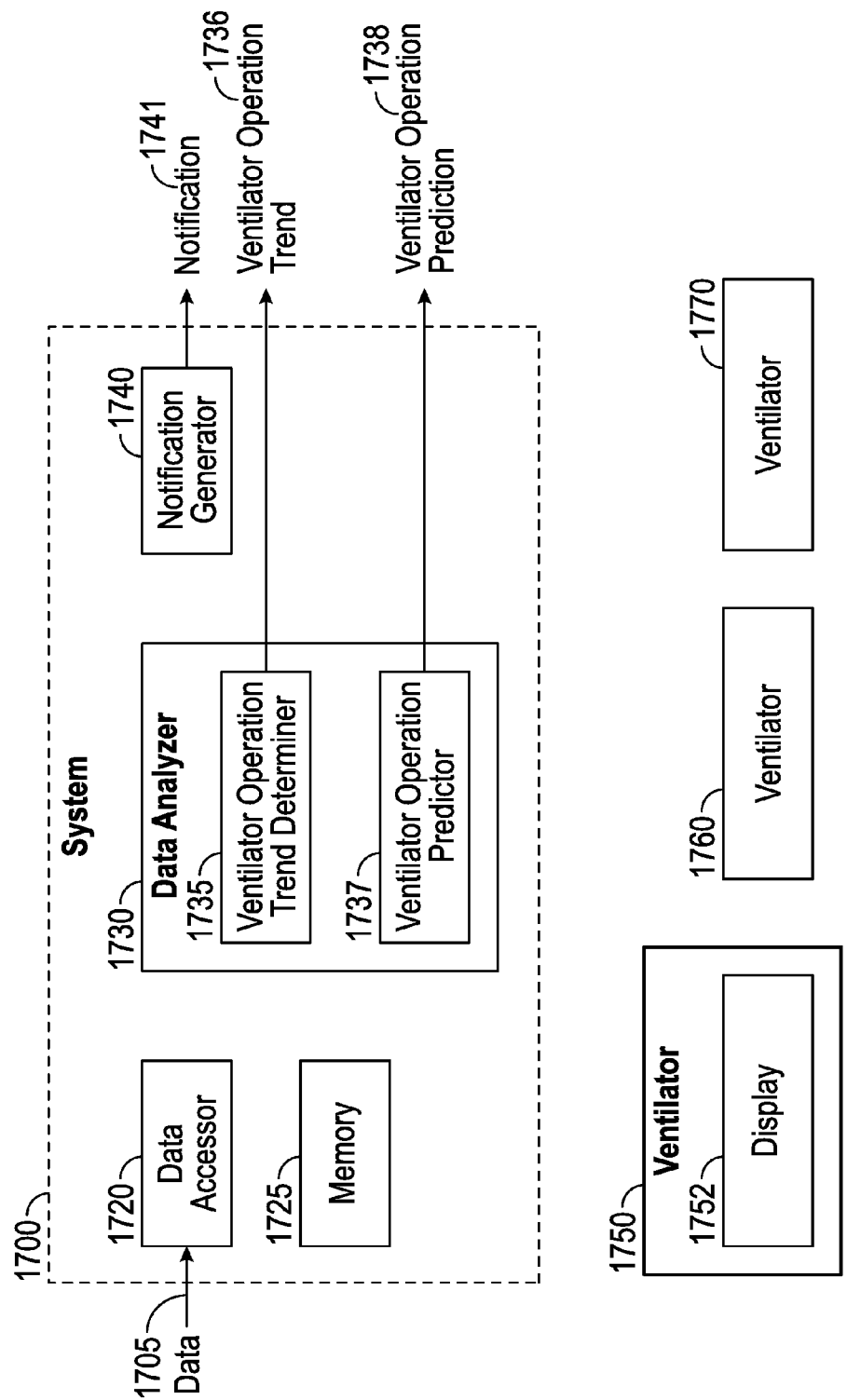
FIGS. 17A, 19, 21, 23, 25, 27, 29, 30, 32, 34, 36, 38 and 41 illustrate various aspects of a medical system.

At step 1610, ventilator data generated by a plurality of networked ventilators is accessed. For example, ventilator data generated by ventilators 510 and 710 is wirelessly accessed via a WAN. At step 1620, wirelessly access patient information of patients of the networked ventilators is wirelessly accessed, wherein the patient information facilitates in contextualization of the ventilator data. For example, patient information of patients associated with ventilators 510 and 710 is wirelessly accessed, wherein the patient information facilitates in contextualization of the ventilator data, as described above. At step 1630, protocols and rules are wirelessly transmitted to the plurality of networked ventilators. For example, protocols and rules are wirelessly transmitted to ventilator 510 and 710. At step 1640, the accessed ventilator data is transmitted to a medical entity. For example, the ventilator data is transmitted to medical entity 120 (e.g., a handheld device registered at a medical entity 120 and associated with a caregiver). At step 1650, the accessed ventilator data is integrated with a patient record. For example, the accessed ventilator data is associated with unique patient data such that the ventilator data is contextualized. At step 1660, the ventilator rules and protocols are customized. For example, the rules are customized based on a ventilator mode and the protocols are customized based on patient information. At step 1670, the customized protocols and the customized rules are provided to at least one of the plurality of ventilators. For example, the customized rules and protocols are wirelessly transmitted to at least one of the ventilators (e.g., ventilator 710), Analyzing Medical Device Data FIG. 17A depicts an embodiment of system 1700. System 1700 can be described as a ventilation data analyzer that includes the ventilator monitoring user interface 125. As will be described in detail below, system 1700 provides information which may assist a clinician or caregiver in observing and inputting certain information with respect to a ventilator. In certain aspects, system 1700 is an embodiment of medical entity 120 and includes instructions in memory 1725 for providing a ventilator monitoring user interface 125.

In certain aspects, the ventilator monitoring user interface 125 is an application for secure access respiratory patient data tracking and reporting. The application provides access to data available over a network 200 (e.g., an integrated delivery network) for respiratory patients using ventilators 1750. The ventilator monitoring user interface 125 is designed to provide a summary view, trending report, and mapping report to support respiratory patient care and management. Summary patient data may be displayed on a patient display page or notification display page of the ventilator monitoring user interface 125. A user with appropriate authorization can access a more detailed view of patient and ventilator data. Additionally, trend charts, detailed data, and detailed reports can be provided to improve an operational efficiency of a healthcare facility's respiratory operations and patient management system by tracking and managing patient respiratory care at many levels.

In certain aspects, the ventilator monitoring user interface 125 is configured to allow users to access the ventilator monitoring user interface 125 using a mobile device (e.g., a client 130 that is mobile). The ventilator monitoring user interface 125 is further configured to function with ventilators 1750 with various different configurations (e.g., by various different manufacturers). In certain aspects, the ventilator monitoring user interface 125 is limited to read-only access for data for a ventilator 1750, thereby protecting the ventilator data from unintended modification or corruption. Additionally, access to the ventilator data can be logged, which provides an audit history of access to the ventilator data. The ventilator monitoring user interface 125 is yet further configured to allow authorized users (e.g., caregivers) to configure thresholds for ventilator settings in order to be in compliance with policies of a healthcare institution. The ventilator monitoring user interface 125 can include a menu bar that includes features to manage and analyze patients' respiratory care, manage ventilator usage, and view summary patient and patient notification data for enhanced patient care.

In certain aspects, the ventilator monitoring user interface 125 may be limited in use to the monitoring of ventilator data from medical ventilators, and is not configured for use in providing a medical diagnosis or medical treatment. For example, in certain aspects, the ventilator monitoring user interface 125 does not directly interface with a medical ventilator or other medical device, but instead obtains data on a medical ventilator from a server.

Returning to the system 1700 of FIG. 17A, system 1700 is configured for analyzing medical device data, such as ventilator data associated with one or many ventilators 1750, 1760, and 1770. The analysis may be based on clinical data analysis or disease management strategies. The analysis can include a continuous quality improvement (CQI) analysis and reporting for ventilators 1750, 1760, and 1770, giving a healthcare institution or caregiver the ability to make improvements in the management of patients and ventilators.

System 1700 includes data accessor 1720, data analyzer 1730 and notification generator 1740. Moreover, system 1700 includes ventilators 1750-1770. Although FIG. 17A depicts three ventilators, it should be appreciated that system 1700 includes at least one ventilator. Data accessor 1720 is configured for accessing data from a plurality of ventilators. For instance, data accessor 1720 accesses data 1705 from the ventilators 1750-1770. In various embodiments, data accessor 1720 can access data from a single ventilator or any number of ventilators (e.g., ventilators 110, 510 and/or 710). Data 1705 can be any information, provided by a ventilator, such as information that facilitates in assisting a clinician in observing and inputting certain information for patient care. Data 1705 can be, but is not limited to, modes of operation, vent settings, patient vital signs, breath sounds, patient orientation, etc.

Data analyzer 1730 is configured for analyzing an aggregate of data 1705. Data analyzer 1730 includes ventilator operation trend determiner 1735 and ventilator operation predictor 1737. Ventilator operation trend determiner 1735 is configured for determining an operation trend 1736 for a ventilator(s), such as ventilators 1750-1770, based on data 1705. Ventilator operation predictor 1737 is configured for predicting a ventilator operation prediction 1738 for ventilator(s), such as ventilators 1750-1770, based on data 1705. Notification generator 1740 is configured for generating notification 1741 for one or more ventilators.

System 1700 can be connected to a variety of networks, such as but not limited to, healthcare facility networks, wide area networks, etc. Additionally, system 1700 can also be coupled directly to ventilators, such as ventilators 1750-1770. In certain aspects, one or more components of system 1700 are located within a ventilator. During use of system 1700, ventilators 1750-1770 are in operation with respective patients. During operation of ventilators 1750-1770, ventilators 1750-1770 generate data 1705 which is accessed by data accessor 1720. Data 1705 is the aggregate data from the ventilators 1750-1770. However, if only one ventilator is in operation or connected to system 1700, then data 1705 is data only from that single ventilator.

The ventilators 1750-1770 are capable of bi-directional communication with system 1700. For example, the ventilators 1750-1770 are able to send information to system 1700 and also receive information from system 1700. In various embodiments, the ventilators 1750-1770 can include a camera, information scanner, touch screen display, microphone, and memory. It should be appreciated that data 1705 is accessed over any time period. For example, data 1705 can be the aggregate data provided over days or months. In certain aspects, data 1705 can be stored in memory 1725.

Data analyzer 1730 receives data 1705. In general, data analyzer 1730 facilitates analyzing data 1705 to provide information that may assist a clinician in observing and inputting certain information with respect to a ventilator. Ventilator operation trend determiner 1735 determines ventilator operation trend 1736 based on data 1705. In general, ventilator operation trend 1736 applies to a general tendency or course of a particular ventilator's operation with a particular patient based on data 1705. Ventilator operation predictor 1737 determines ventilator operation prediction 1738 based on ventilator operation trend 1736 and/or data 1705. In general, ventilator operation prediction 1738 applies to an operation of a particular ventilator with a particular patient.

Ventilator operation prediction 1738 can be based on specific ventilator modes of operation and/or patient vitals that are compared to aggregated data 1705. Accordingly, this allows a clinician to know that certain outcomes are likely. Thus, the clinician can prepare accordingly, or provide proactive treatment to prevent the outcomes. In various embodiments, ventilator operation trend 1736 and/or ventilator operation prediction 1738 provides information that assists a clinician in observing and inputting certain information related to, but not limited to, delivery of neonatal oxygen, lung protective strategy, sedation effects or events surrounding sedation, weaning effects, suction effects, and transpulmonary pressure. Also, ventilator operation trend 1736 and/or ventilator operation prediction 1738 can be displayed on a ventilator's screen, hand-held device, or other network device.

Notification generator 1740 generates notification 1741 based on ventilator operation trend 1736 and/or aggregated data 1705. In other words, system 1700 monitors certain modes of operation and/or patient vitals. Accordingly, notification 1741 is generated for notifying a clinician of various levels of modes of operation and/or patient vitals. Notification 1741 can be customized. For example, notification 1741 can be selected to be a warning tone in response to negative trend analysis, ventilation being performed which contradicts with an assigned protocol, or violation of a rule. In various embodiments, notification 1741 is sent to a nursing station, supervisor, caregiver, or pager.

Figure 17B:
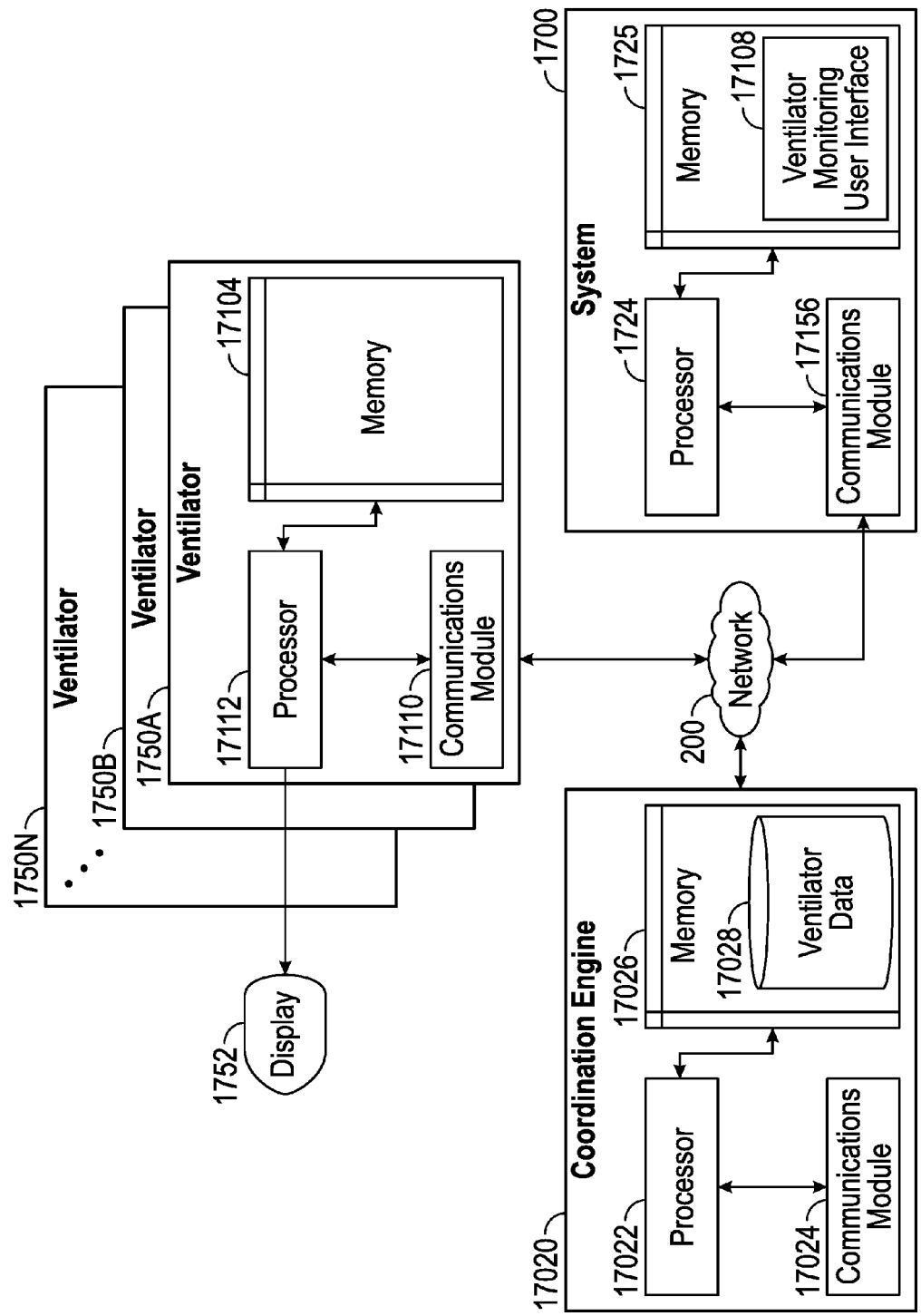
FIG. 17B is a block diagram illustrating example ventilators, coordination engine, and system from FIG. 17A according to certain aspects of the disclosure.

FIG. 17B is a block diagram illustrating example ventilators 1750A-1750N, a coordination engine 17020, and system 1700 according to certain aspects of the disclosure. Although one ventilator 1750A is shown in detail, it is understood that each of the remaining ventilators 1750A-1750N is configured similarly to ventilator 1750A. The ventilators 1750A-1750N, coordination engine 17020, and system 1700 are connected over the network 200 via respective communications modules 17110, 17024, and 17156. The communications modules 17110, 17024, and 17156 are configured to interface with the network 200 to send and receive information, such as data, requests, responses, and commands to other devices on the network 200. The communications modules 17110, 17024, and 17156 can be, for example, modems or Ethernet cards.

Each of the ventilators 1750A-1750N is configured to provide data 1705 to the coordination engine 17020 for storage in memory 17026 as ventilator data 17028 via respective processors 17112 and 17022 of the ventilators 1750A-1750N and coordination engine 17020. The ventilator data 17028 can include, for example, a medical ventilator start time, a medical ventilator mode, tidal volume, ventilation frequency, fraction of inspired oxygen, and positive end respiratory pressure.

In turn, the processor 17022 of the coordination engine 17020 is configured to provide the ventilator data 17028 to the processor 1724 of the system 1700 in response to a request sent over the network 200 from the ventilator monitoring user interface 17108 (e.g., ventilator monitoring user interface 125) in the memory 1725 of the system 1700. The processor 1724 of the system 1700 is further configured to execute instructions, such as instructions physically coded into the processor 1724, instructions received from software in memory 1725 (e.g., the ventilator monitoring user interface 17108), or a combination of both, to receive the ventilator data 17028 for the ventilators 1750A-1750N (e.g., over the network 200) and identify a configuration for each of the ventilators 1750A-1750N from the received data 17028.

The processor 1724 is also configured to associate each patient with a respective one of the ventilators 1750A-1750N, and determine an identification and status for each patient associated with one of the plurality of medical ventilators. The identification for each patient can include an account identification, a patient name, patient care area, and patient location. The processor 1724 is further configured to provide, for display (e.g., display 1752), information indicative of the configuration of each of the ventilators 1750A-1750N, and indicative of the identification and status of each patient associated with the ventilators 1750A-1750N. In certain aspects, the information is provided for display using an interface configured for a non-mobile device (e.g., system 1700), but can also be configured for display in a mobile format for a mobile device (e.g., client 130). The information provided for display can also include a total estimated ventilation cost for patients in a first period, a total estimated ventilation cost for patients in a second, baseline period, a total estimated weaning cost for patients in the first period, a total estimated weaning cost for patients in the second period, and a difference in cost between the first period and the second period.

The information indicative of the configuration of each of the ventilators 1750A-1750N can include, for example, an apnea interval, a bias flow, a compression volume, a $CO_2$ value, a demand flow, a diameter, an average end tidal $CO_2$, $FiO_2$, a flow cycle, or a flow trigger. The information indicative of the identification and status of each patient can include, for example, measured physiological statistics for dynamic compliance, inverse ratio ventilation, mandatory ventilation rate, mandatory exhaled tidal volume, total lung ventilation per minute, PEEP, PEFR, PIFR, mean airway pressure, peak airway pressure, or total ventilation rate. The information indicative of the identification and status of each patient can also include providing information for patients in a care area. The information for patients in the care area includes a number of weaning candidates, average number days on a medical ventilator, average number of hours from a first weaning marker to a first spontaneous breathing trial, average number of hours from the first weaning marker to a final extubation, a reintubation rate, a total estimated ventilation cost for patients with weaning markers, an average estimated ventilation cost for patients with weaning markers, patient weaning information grouped by physician, a number of patients with alarm notifications, an average number of times patients in the care area have had physiological statistics exceeding acceptable thresholds, or a percentage of time patients in the care area have had physiological statistics exceeding acceptable thresholds. The information for patients in the care area can be provided in a text format, chart format, or both.

In certain aspects, the ventilator monitoring user interface 17108 is configured to provide notifications when the information indicative of the configuration of a ventilator 1750A-1750N or of the identification or status of a patient exceeds a configured threshold value (e.g., a value defined by an administrator or health care provider). The notification can be issued as an alert for the ventilator 1750A-1750N associated with the patient, or an alert indicating a non-compliance of the ventilator 1750A-1750N with a compliance policy. The threshold values are configurable by authorized users. For example, when the ventilator data 17028 includes physiological statistics for a patient obtained from a ventilator 1750A-1750N, a threshold value can be defined in the ventilator monitoring user interface 17108 for generating a notification when a physiological statistic for the patient exceeds a threshold value.

The ventilator monitoring user interface 17108 is also configured to generate reports (e.g., for display on the system 1700 or on an authorized client 130) based on the ventilator data 17028. The reports can be specific to a patient, ventilator, care area, physician, or other identifier, and can include analytics data or summary data. Parameters for generating the report can be configured by a user at the system 1700 or on the authorized client 130.

Example reports can include weaning summary reports, weaning details reports, medical ventilator settings reports, medical ventilator history reports, lung protection reports, and patient detail reports. For instance, a weaning report can include current, minimum, and maximum values for a patient information for at least one of $FiO_2$, minute ventilation, PEEP, VT, total ventilation rate, and work of breathing measured.

In addition to receiving ventilator data 17028 from the coordination engine 17020, the processor 1724 of the system 1700 is configured to transmit requests to the ventilators 1750A-1750N, either through the coordination engine 17020 or directly to the ventilators 1750A-1750N. The requests can include requests to remotely access a ventilator 1750A-1750N, to remotely control a ventilator 1750A-1750N, to annotate data stored on a ventilator 1750A-1750N, to change information for a patient associated with a ventilator 1750A-1750N, or obtain diagnostic information for a ventilator 1750A-1750N.

Authorized users can have one of several security roles, such as a system administrator, customer user administrator, integrated data network viewer, or client viewer. Based on a user's role, a user may be granted or restricted access to various features of the ventilator monitoring user interface 17108. For example, a user may be limited from accessing graphical user interfaces for patient view, patient detail view, patient trend view, marker view, executive summary, key performance indicator (KPI) detail, patient thresholds configuration, hospital care area configuration, location to care area mapping, ventilator cost configuration, user security maintenance, weaning summary report, weaning details report, ventilator settings report, ventilator history report, lung protection analytics summary report, lung protection analytics details report, integrated data network access, and client access.

The ventilator cost configuration includes settings that enable a user to measure an estimated cost for a ventilator therapy metric KPI. The user security maintenance interface permits a management user to have certain privileges. The hospital care area configuration interface permits a user to design or organize and track patient ventilator locations within all hospital care areas. The hospital care area configuration functionality supports configuration and management of ventilators by care area within the facility. Records may be mapped by location. Location to care area mapping permits a user to view, track, and manage patient ventilator locations in hospital care areas. The mapping functionality supports management of ventilators by location and area within the facility. Location to care area mapping functionality provides location mapping for records in the hospital care area configuration.

The patient thresholds configuration permits a user to override system default criteria and apply setting selections in threshold categories. The threshold categories include weaning analytics, lung protection analytics, alarm settings analytics, and event definition.

Thresholds for weaning analytics include a weaning candidate threshold, which is a configurable setting that identifies what criteria need to be met for identifying a patient as a weaning candidate and for the creation of a weaning candidate marker. Thresholds for weaning analytics also include an SBT threshold, a configurable setting that determines the normal length of time an SBT should last. When an SBT exceeds this setting, a marker is generated identifying an SBT longer than the recommended length of time. Thresholds for weaning analytics further include an extubation candidate threshold, which is a configurable setting that identifies what criteria need to be met to identify the patient as an extubation candidate and for the creation of an extubation candidate marker.

Thresholds for lung protection analytics include tidal volume ratio limit, which specifies the criteria for tidal volume ratio limit and the criteria that are non-compliant with hospital policy. The metrics for tidal volume ratio limit can be composed using ideal body weight. Thresholds for lung protection analytics also include plateau pressure limit, which specifies the criteria for plateau pressure limit and criteria that are non-compliant with hospital policy. Thresholds for lung protection analytics further include transpulmonary plateau pressure limit, which specifies the criteria for transpulmonary plateau pressure limit and the criteria that are non-compliant with hospital policy.

Thresholds for alarm settings analytics include a low and high peak inspiratory pressure (Ppeak) limit, which specify the criteria when low Ppeak and high Ppeak is out of compliance. Thresholds for alarm settings analytics also include a low ventilation (VE) and high VE limit, which specify the criteria when low VE and high VE are out of compliance.

Thresholds for event definition include a reintubation rate threshold, which identifies the length of time a patient needs to be disconnected from a ventilator in order to start a new ventilation session and be counted as a reintubation event. A patient who is away from the ventilator for less than the configured length of time (e.g., for a transport to radiology, an operating room, or another ICU room) and is then returned to their ventilator will have the previous ventilator session resumed.

Figure 17C:
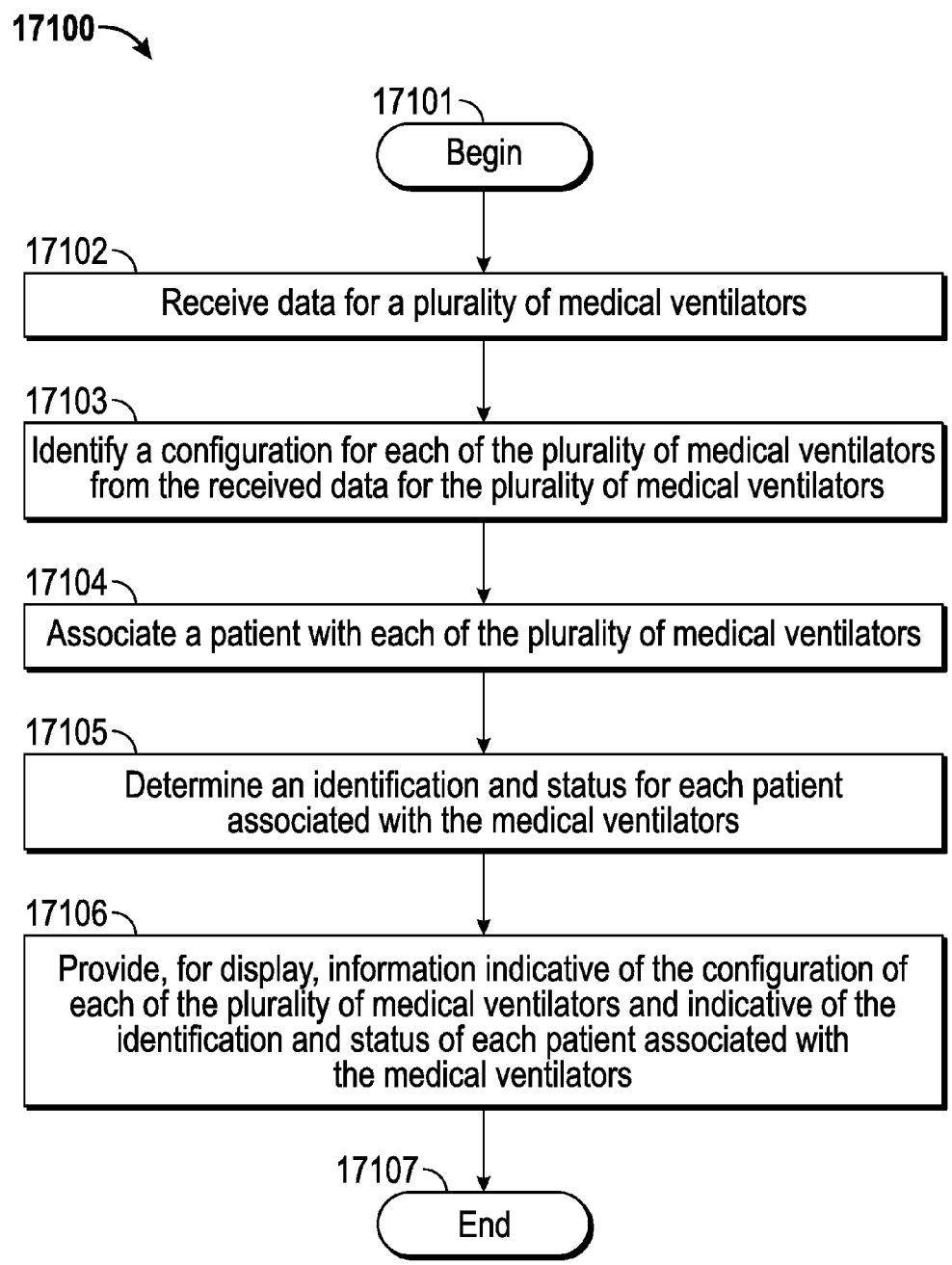
FIG. 17C illustrates an example process for monitoring multiple medical ventilators using the system of FIG. 17B.
Figure 17D:
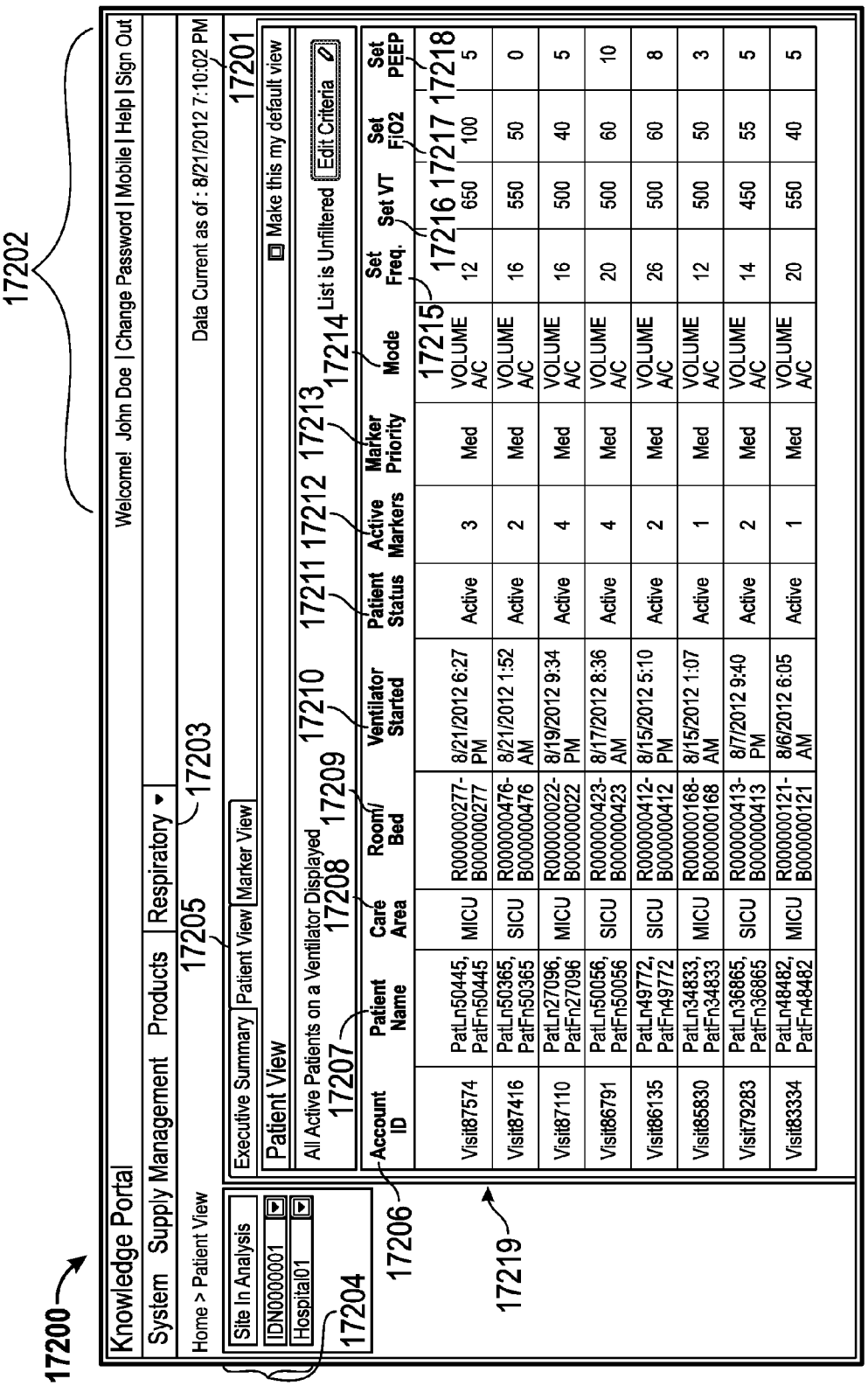
FIGS. 17D-17X are example illustrations of a ventilator monitoring user interface associated with the example process of FIG. 17C.

FIG. 17C illustrates an example process 17100 for monitoring ventilators 1750A-1750N using the system 1700 of FIG. 17B. While FIG. 17C is described with reference to the system 1700 of FIG. 17B, it should be noted that the process steps of FIG. 17C may be performed by other systems. The process 17100 begins by proceeding from beginning step 17101 when the ventilator monitoring user interface 17108 is initialized on the system 1700 to step 17102 when the system 1700 receives ventilator data 17028 for the medical ventilators 1750A-1750N. In step 17103, the system 1700 identifies a configuration for each of the ventilators 1750A-1750N and in step 17104 associates a patient with each of the ventilators 1750A-1750N. Next, in step 17105, the system 1700 determines an identification and status for each patient associated with the ventilators 1750A-1750N. In step 17106 the system 1700 provides, for display (e.g., in the ventilator monitoring user interface 17108 on display 1752), information indicative of the configuration of each ventilator 1750A-1750N and indicative of the identification and status of each patient associated with the ventilators 1750A-1750N, and the process 17100 ends in step 17107. FIGS. 17D-17X are example illustrations of information as provided for display in the ventilator monitoring user interface 17108.

With reference to FIG. 17D, an example illustration 17200 of a patient view in the ventilator monitoring user interface 17108 is provided. The patient view is selected in the ventilator monitoring user interface 17108 by selecting the patient view tab 17205 after gaining authorized access to the ventilator monitoring user interface 17108. The patient view includes a timestamp 17201 indicating the time of the data being displayed, and an authorized user account menu bar 17202 for identifying the authorized user, updating the authorized user's account, changing to a mobile interface mode, obtaining additional information on how to use the ventilator monitoring user interface 17108, and signing out of the ventilator monitoring user interface 17108. The authorized user account menu bar 17202 permits the user to acquire a first-time user password, reset a password, and find contact information for customer support.

The displayed tab interface (e.g., patient view tab 17205) provides an authorized user with access to each of the graphical user interfaces available for the ventilator monitoring user interface 17108. For example, the user can access a user security maintenance interface for ventilator cost configuration, user security maintenance, hospital care area configuration, location to care area mapping, and patient thresholds configuration. The user can access a reports interface for viewing a weaning summary report, weaning details report, ventilator settings report, ventilator history report, lung protection analytics summary report, and lung protection analytics details report. The user can access a patient view interface in which all active patients on a ventilator are displayed, as well as ventilator information (e.g., ventilator type, ventilator started date and time), such as settings, measured values, reports, markers, and care notes. The user can access a marker view interface in which all active markers are displayed as well as ventilator information (e.g., ventilator type, ventilator started date and time), such as settings, measured values, reports, markers, and care notes. The user can access an executive summary interface, which can be set as the default home page when logging on to the ventilator monitoring user interface 17108.

The patient view of FIG. 17D further includes a table of patient data 17219 organized by a selected healthcare institution site 17204. The table of patient data 17219 includes, for each listed patient, an account identification 17206, a patient name 17207, the patient's care area 17208, the patient's room and bed identifier 17209, a time at which a ventilator for the patient was started 17210, the patient's status 17211, active markers 17212 associated with the patient, a priority of the markers 17213 associated with the patient, the current mode 17214 of the ventilator associated with the patient, a ventilation frequency 17215, tidal volume 17216, fraction of inspired oxygen 17217, and positive end respiratory pressure 17218. For example, for a first patient 17219 is identified as being located in the mobile intensive care unit (MICU) care area 17208 and has an active status 17211 with three associated patient markers 17213.

FIG. 17E provides an example illustration 17230 of a marker view in the ventilator monitoring user interface 17108. The marker view is selected in the ventilator monitoring user interface 17108 by selecting the marker view tab 17231. The marker view includes a table of patient marker data organized by medical record number (MRN) and sorted by marker priority 17213. The table includes an account identifier 17206, a patient's name 17207, the time the marker was generated 17233, a patient status 17211, a priority of the market 17213, and a marker description 17234. For example, two markers 17234 are displayed for a patient 17235 indicating the patient's "Ve high alarm limit" and "Ppeak low alarm limit" are not in compliance with operational policy. In certain aspects, markers can be configured by permitting a user to define required and optional metric when specifying a threshold.

FIG. 17F provides an example illustration 17240 of an executive summary in the ventilator monitoring user interface 17108. The executive summary focuses on historical retrospective data measures (e.g., length of stay (LOS) with KPIs) categorized by various analytics. The executive summary is selected in the ventilator monitoring user interface 17108 by selecting the executive summary tab 17241. The executive summary can be configured to summarize certain aspects of the ventilator data 17028. In the example illustration 17240, a monthly performance scorecard 17242 for the ventilators 1750A-1750N is provided for a particular hospital site. The performance scorecard includes information on KPIs 17243, current period values 17244, comparison period values 17245, a difference 17246 between the current period values 17244 and the comparison period values 17245, and trend reports 17249 organized by categories, namely, weaning analytics 17247 and lung protection analytics 17248. The weaning analytics 17247 includes information indicating a number of all patients on a ventilator at the site, an average number of days all of the patients have been on a ventilator 17251, a total estimated ventilator cost for all of the patients 17252, a reintubation rate for all of the patients 17253, a number of weaning candidates 17254, an average number of ventilation days for the weaning candidates 17255, and a total estimated ventilation cost for the weaning candidates 17256. The executive summary can also include visual indicators (e.g., icons) that indicate whether an associated value meets or exceeds a configured threshold.

Figure 17G:

FIG. 17G provides an example illustration 17260 of a detailed patient report. A detailed patient report can be accessed by selecting a patient identified in the ventilator monitoring user interface 17108. The illustrated detailed patient report includes an identification 17261 of the patient and the patient's ventilator, the identification of the patient including the patient's name, medical record number, and status, and the identification of the ventilator including the ventilator type and time the ventilator was started. The detailed patient report also includes, for the patient, settings information 17262 for the patient's ventilator and values 17263 measured by the patient's ventilator. The detailed patient report further includes an interface for generating a patient report 17264, a view of markers 17265 associated with the patient, and care notes 17266 associated with the patient. The settings information 17262 includes information indicating, for the ventilator, an AAC status, an apnea interval, a bias flow, a compression volume, a $CO_2$ value, a demand flow, a diameter, an average end tidal $CO_2$, a fraction of inspired oxygen ($FiO_2$), a flow cycle, and a flow trigger. The measured values 17263 include dynamic compliance, inverse ratio ventilation, mandatory ventilation rate, mandatory exhaled tidal volume (VTE), total lung ventilation per minute, positive end respiratory pressure (PEEP), peak expiratory flow rate (PEFR), peak inspiratory flow rate (PIFR), mean airway pressure, peak airway pressure, and total ventilation rate. The measured values 17263 illustrate trends in the values as lines 17267 angled in the direction of the trend. FIG. 17H provides an example illustration 17270 of an alternative view for a detailed patient report. Unlike the detailed patient report in the example illustration 17260 of FIG. 17G, the detailed patient report in FIG. 17H provides chart graphs 17273 and 17274 illustrating trends for the settings 17271 and the measured values 17272 of the detailed patient report.

Figure 17I:
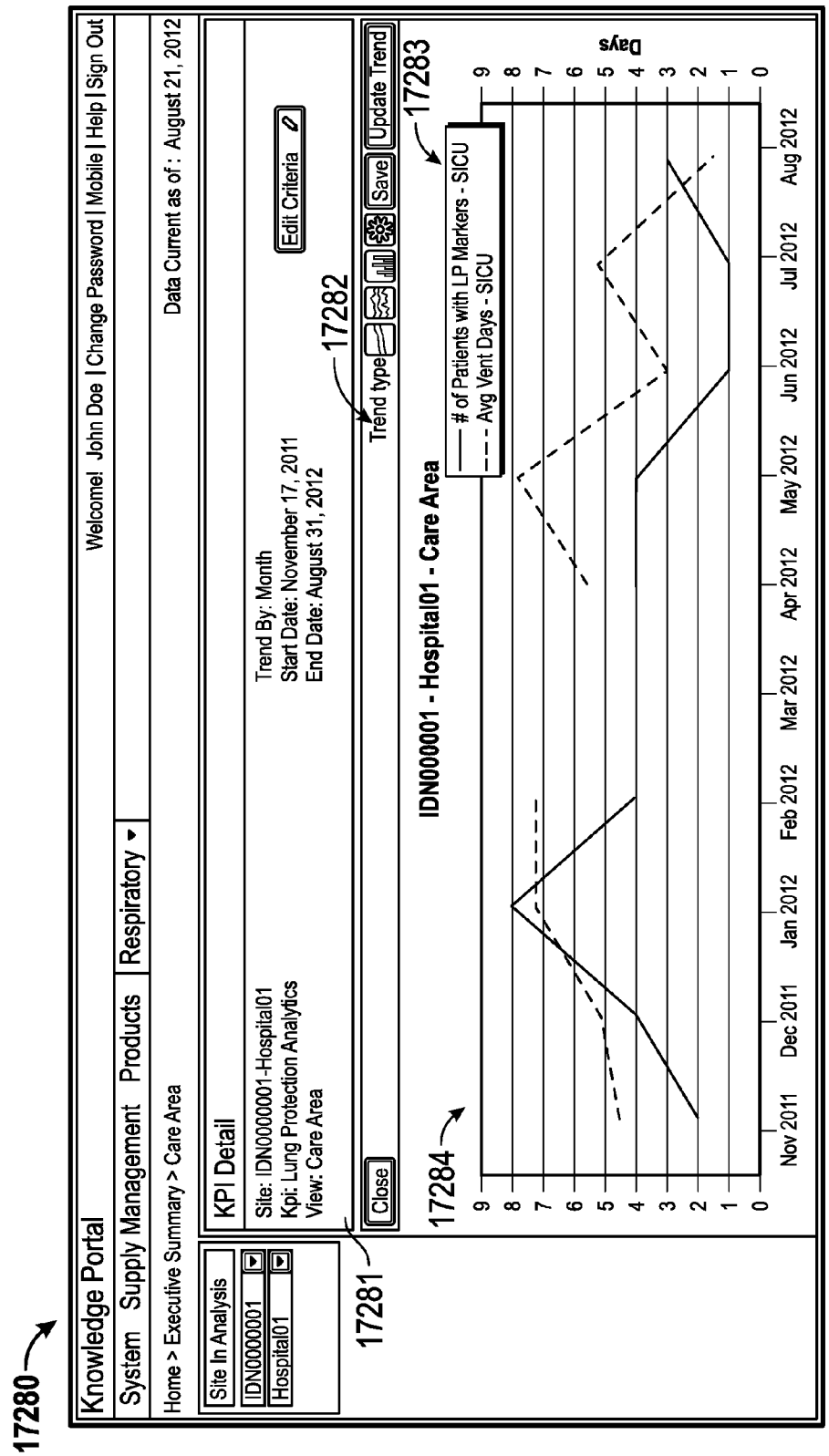

FIG. 17I provides an example illustration 17280 of a lung protection analytics trend report. A lung protection analytics trend report can be generated and accessed through various different interfaces for generating reports provided in the ventilator monitoring user interface 17108 (e.g., by selecting a "trend" link associated with displayed information). The lung protection analytics trend report details 17281 the key performance indicator, health care institution site, view, and time for a graphic illustration of a trend 17284. The graphic illustration of the trend 17284 includes a key 17283 for facilitating an understanding of the trend 17284. The type of graphic illustration type for the trend can also be selected 17282 using the provided interface.

FIG. 17J provides an example illustration 17290 of a lung protection analytics report that is organized by care area and physician. The lung protection analytics report identifies a care area 17208, physician 17291, number of patients with lung protection (LP) markers 17292, an average number of days for patients on the ventilator 17293, an average number of times patients have exceeded acceptable threshold values 17294, and an average number of hours during which patients have exceeded acceptable threshold values 17295. For example, in a first surgical intensive care unit (SICU) 17296, physician DocLn00120 has one patient with an LP marker that has been outside acceptable threshold values an average of three times. In certain aspects, a user can configure a threshold for lung protective strategies and whether and how notifications are to issue when such thresholds are exceeded. Furthermore, the lung protection analytics report can be based on information for each patient that indicates the patient's height and weight.

Figure 17K:

FIG. 17K provides an example illustration 17300 of an interface for selecting report parameters to generate a detailed lung protective strategies report. The selectable parameters include the patients to populate the report 17301, a start date and end date of the report 17302, and a patient discharge status 17303. FIG. 17L provides an example illustration 17310 of an interface for selecting report parameters to generate a summary lung protective strategies report, which is different than the detailed lung protective strategies report of FIG. 17K. The summary lung protective strategies report of FIG. 17L includes similar selectable parameters to the detailed lung protective strategies report of FIG. 17K.

FIG. 17M provides an example illustration 17320 of another lung protection analytics report. The lung protection analytics report of FIG. 17M provides information organized by patient care area 17208, unlike the lung protection analytics report of FIG. 17J, which provides similar information that is further organized by physician 17291.

Figure 17N:
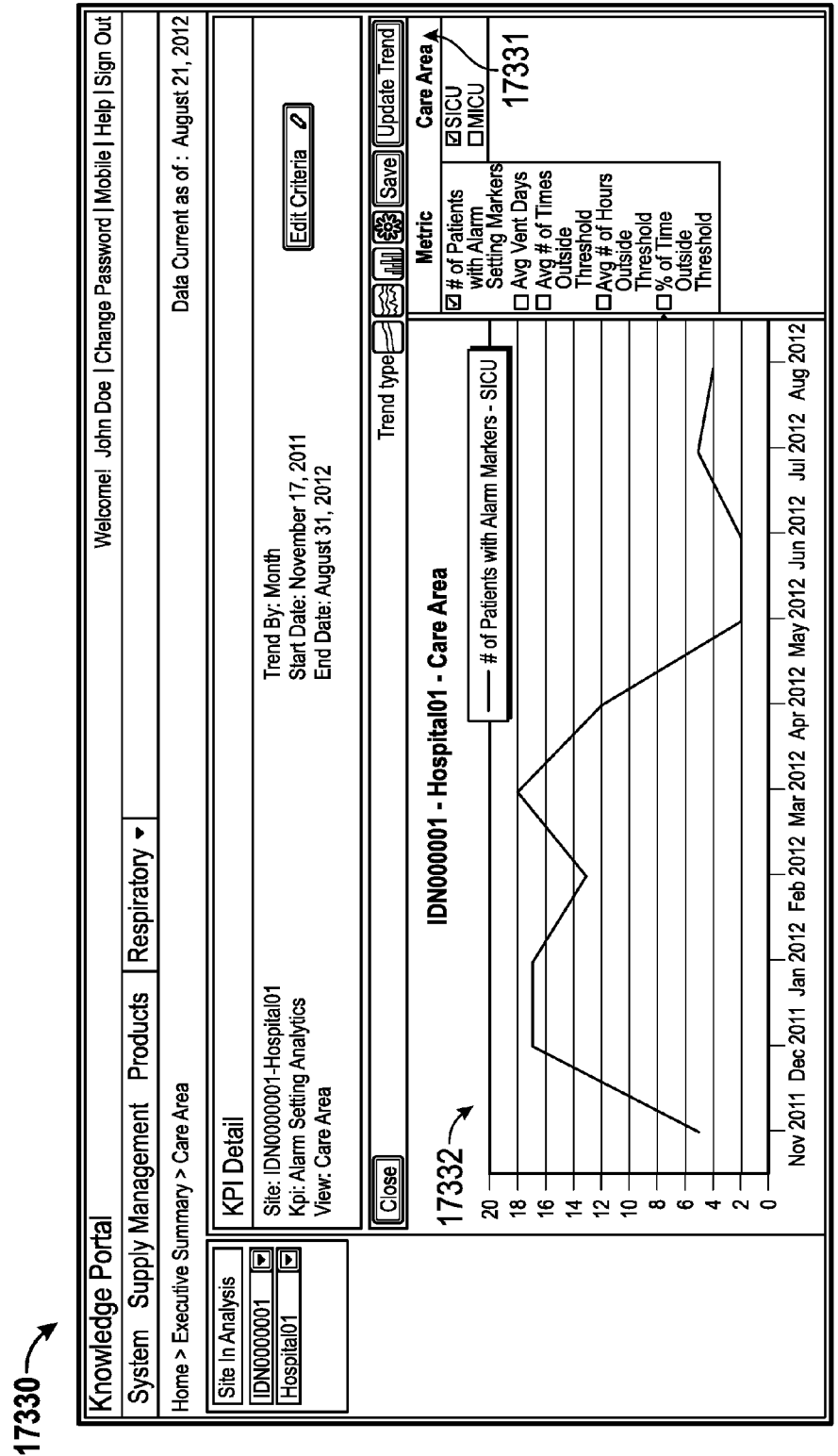

FIG. 17N provides an example illustration 17330 of an alarm setting analytics trend report. The alarm setting analytics trend report provides a graphical illustration 17332 of trends associated with patients with alarm settings markers. The graphical illustration is provided according to a specific site, key performance indicator, and care area. The parameters used in generating the graphical illustration 17332 can be configured using the provided interface 17331.

Figure 17O:
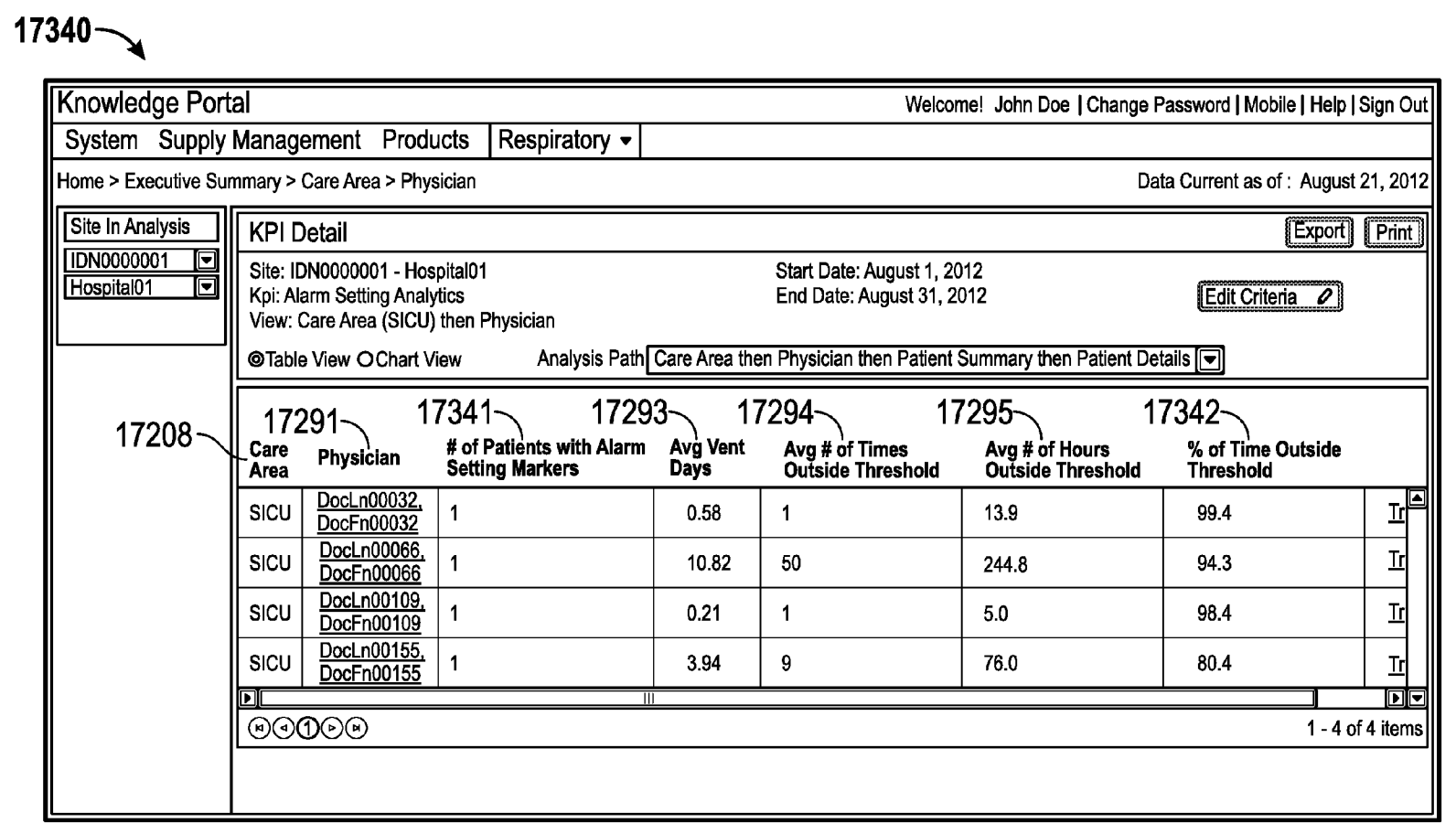

FIG. 17O provides an example illustration 17340 of an alarm setting analytics trend report that is organized by care area 17208 and physician 17291. The report of FIG. 17O includes information, for each care area and physician, indicative of a number of patients with alarm setting markers 17341, an average number of days on a ventilator 17293, an average number of times patients have exceeded acceptable threshold values 17294, an average number of hours during which patients have exceeded acceptable threshold values 17295, and a percentage of time on the ventilator that the patients have exceeded acceptable threshold values 17342. FIG. 17P provides an example illustration 17350 of an alarm setting analytics report. Unlike the alarm settings analytics trend report of FIG. 17O, the information provided for display in the alarm setting analytics report of FIG. 17P is organized by patient care area 17208 and not also by physician.

FIG. 17Q provides an example illustration 17360 of a weaning summary report. The weaning summary report includes, for each listed patient 17207, information indicative of an account identification 17206, admission date and time 17361, discharge date and time 17362, discharge status 17363, care area 17208, time on a ventilator 17364, time to a first weaning criteria 17365, time from weaning to a first spontaneous breathing event 17366, time from weaning to final extubation 17367, and whether the patient has been reintubated 17368. The time to the first weaning criteria 17365 shows the duration between when patient was placed on a ventilator for the first time and when the patient reached weaning criteria for the first time during the encounter. For example, if the patient was placed on a ventilator at 6:00 AM, and met the weaning criteria for the first time at 10:00 AM, the value for the column would be 4 hours. The time from weaning to a first spontaneous breathing event 17366 shows the duration between when a patient met weaning criteria for the first time and when the patient reached the SBT criteria for the first time during the encounter. For example, if the patient was placed on the ventilator at 6:00 AM, met the weaning criteria for the first time at 10:00 AM, and met the SBT criteria at 1:00 PM, the value for the column is 3 hours. The time from weaning to final extubation 17367 shows the duration between when a patient met weaning criteria for the first time and when the patient was extubated during the encounter. For example, if the patient was placed on the ventilator at 6:00 AM, and last ventilator data received for the patient was at 4:00 PM, and the patient is currently discharged, the value for the column is 10 hours. For reintubation 17368, if a time span is configured for a certain number of hours and a patient has multiple ventilator sessions in a given hospital stay, and if the gap between any of these ventilator sessions is greater than the certain number of hours, the patient is considered reintubated.

FIG. 17R provides an example illustration 17370 of a weaning analytics report. The weaning analytics report includes information organized by care area 17208. The information for each listed care area includes a number of weaning candidates 17254, an average number of days on a ventilator 17255, an average number of hours to a first weaning marker 17371, an average number of hours from the first weaning marker to a first spontaneous breathing event 17372, an average number of hours from the first weaning marker to a final extubation 17373, a reintubation rate 17374, a total estimated ventilator cost for patients with weaning markers 17375, and an average estimated ventilator cost for patients with weaning markers 17376.

FIG. 17S provides an example illustration 17380 of a weaning analytics report that is organized by care area 17208 and physician 17291. The weaning analytics report includes information indicating, for patients in each care area 17208, a number of weaning candidates 17254, an average number of days on a ventilator 17255, an average number of hours to a first weaning marker 17371, an average number of hours from the first weaning marker to a first spontaneous breathing event 17372, an average number of hours from the first weaning marker to a final extubation 17373, a reintubation rate 17374, and a total estimated ventilator cost for patients with weaning markers 17375.

Figure 17T:
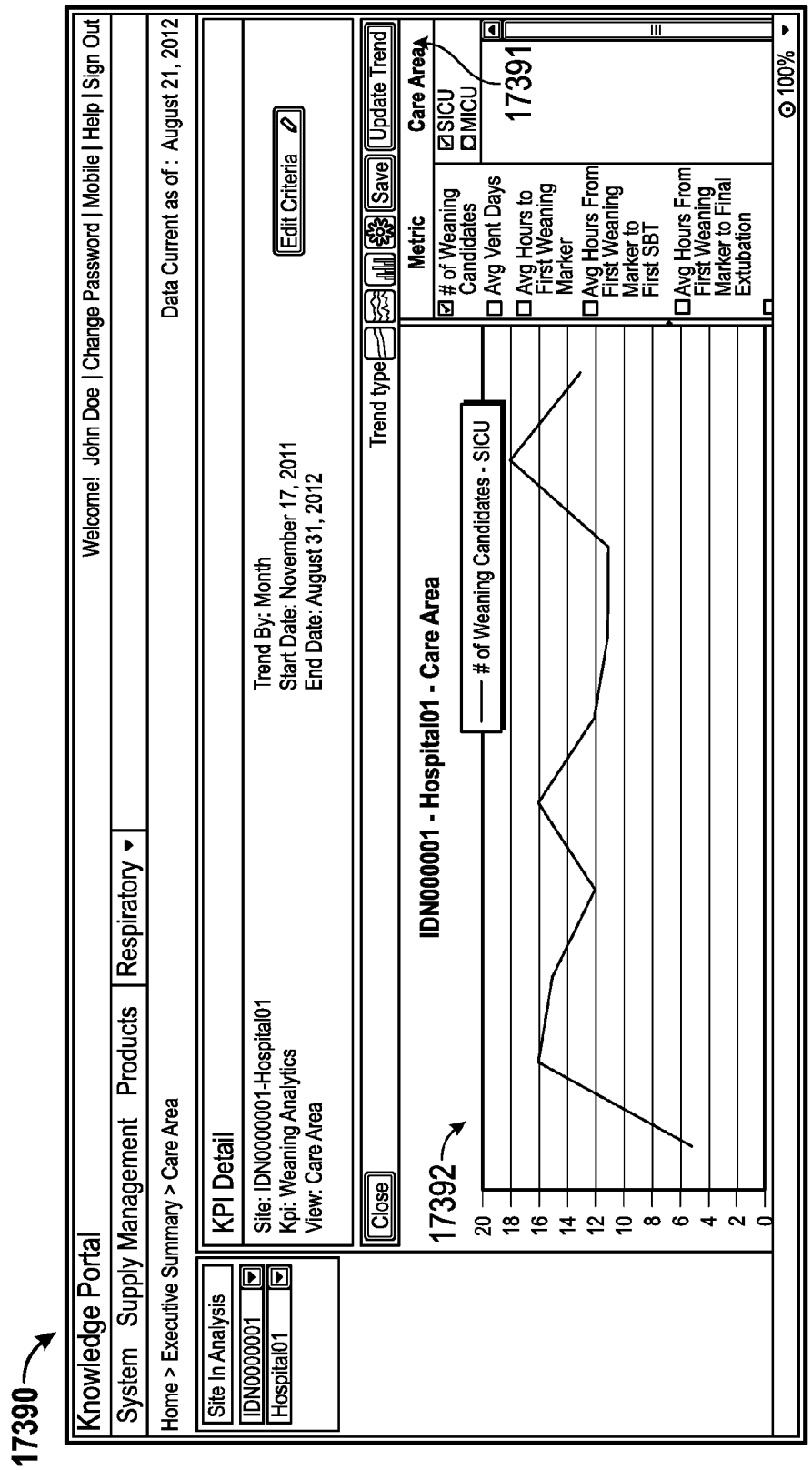
Figure 17V:
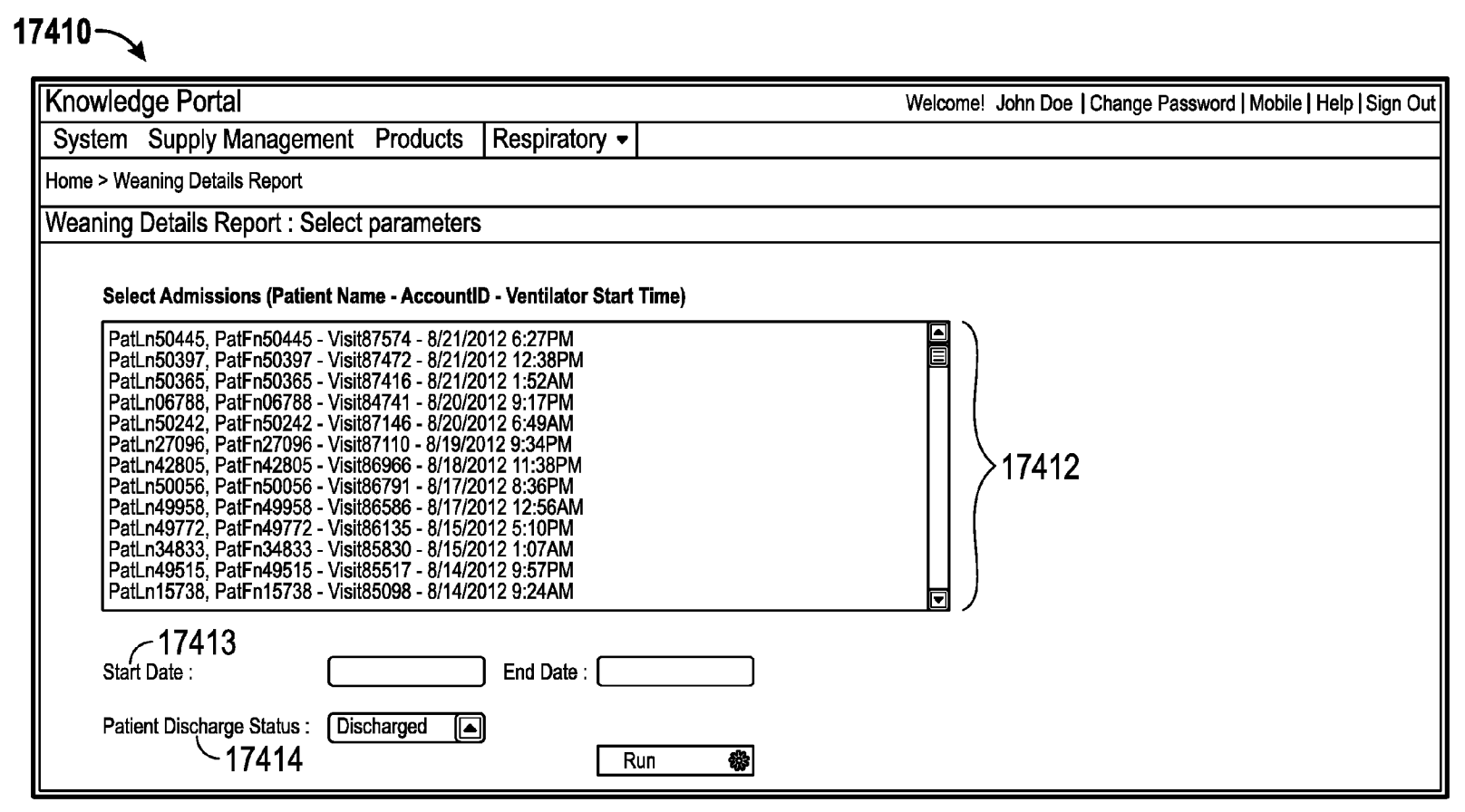
Figure 17X:
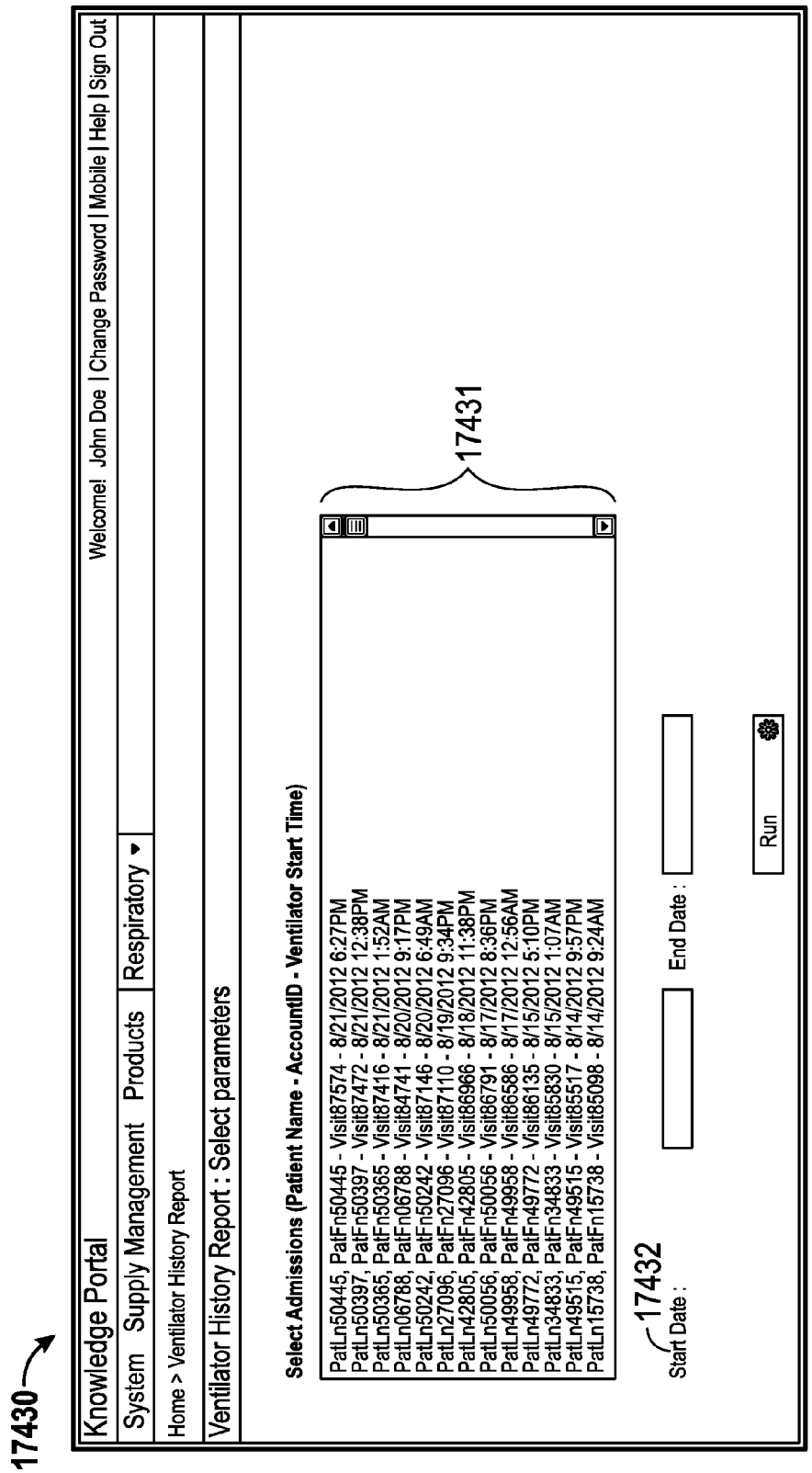

FIG. 17T provides an example illustration 17390 of a weaning analytics trend report. The weaning analytics trend report provides a graphic illustration 17392 of the number of weaning candidates in the hospital care area over time. The parameters used to generate the graphic illustration 17392 for the weaning analytics trend report can be configured using the provided interface 17391.

FIG. 17U provides an example illustration 17400 of a detailed weaning report. The illustrated detailed weaning report is generated for a specific patient at a hospital. The detailed weaning report includes information for the patient indicative of an event category 17401 (e.g., an hourly summary, weaning analytics), an event type 17402 (e.g., $FiO_2$, PEEP), an event date and time 17403, a value 17404 for the event type 17402, a minimum value 17405 for the event type 17402, a maximum value 17406 for the event type 17402, and the unit of measure 17407 used. FIG. 17V provides an example illustration 17410 of a parameter selection interface for the detailed weaning report of FIG. 17U. Parameters including a patient identification 17412, start date and end date 17413, and patient discharge status 17414 can be defined in order to generate a detailed weaning report.

Similar to the weaning report of FIG. 17U, the ventilator monitoring user interface 17108 is configured to generate a ventilator settings report and ventilator history report. FIG. 17W provides an example illustration 17420 of a parameter selection interface for such a ventilator settings report. Parameters, including a patient identification 17421 and start date and end date 17422, can be defined in order to generate a ventilator settings report. FIG. 17X provides an example illustration 17430 of a parameter selection interface for such a ventilator history report. Parameters including a patient identification 17431 and start date and end date 17432 can be defined in order to generate a ventilator history report.

Figure 18:
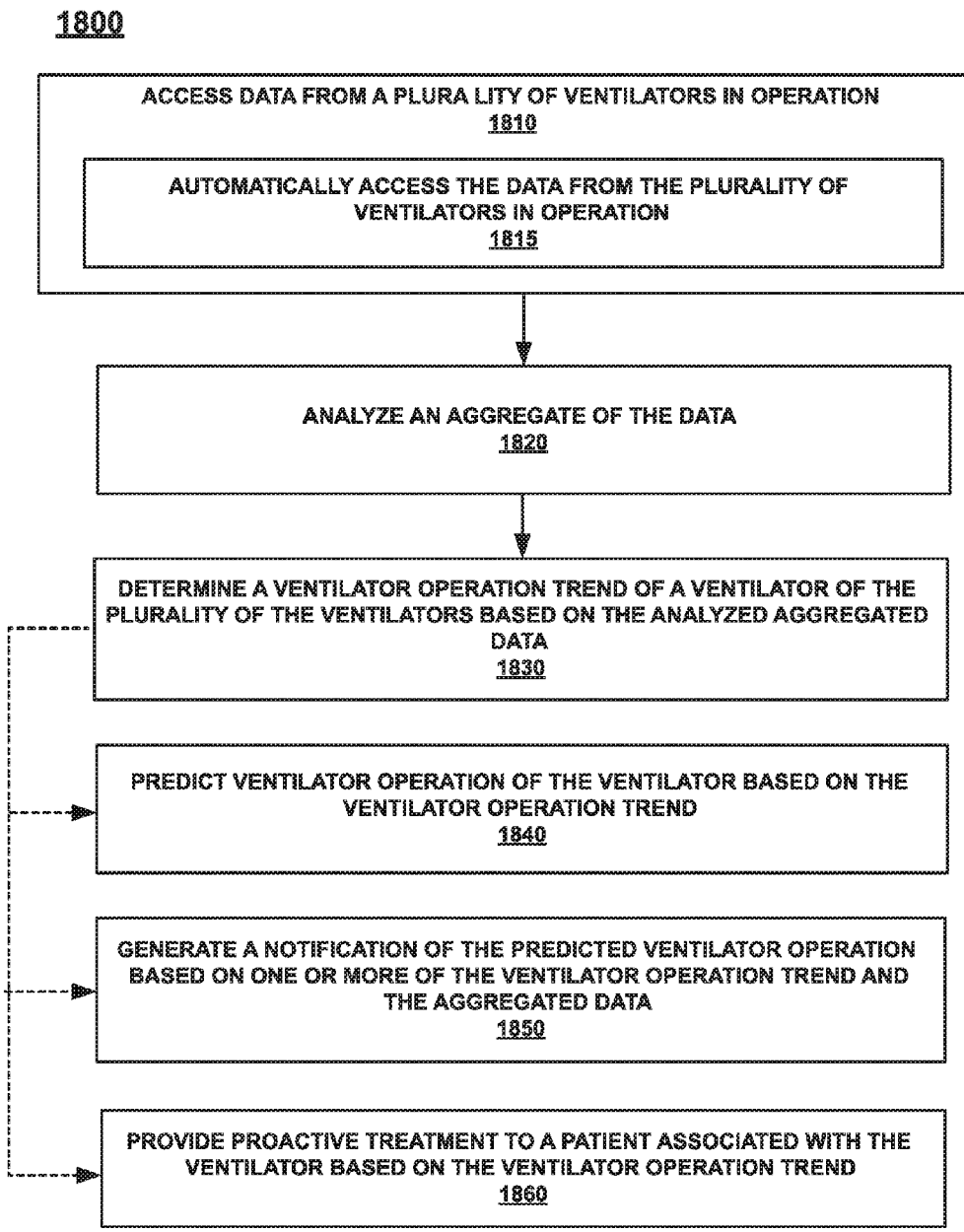
FIG. 18 illustrates an example method for analyzing medical device data.

The ventilator monitoring user interface 17108 is configured to analyze medical device data, namely, data from one or many ventilators 1750A-1750N. FIG. 18 depicts an example method 1800 for analyzing medical device data (e.g., from a ventilator 1750A-1750N). In various embodiments, method 1800 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1800 is performed at least by system 1700, as depicted in FIG. 17A.

At step 1810 of method 1800, data is accessed from a plurality of ventilators in operation. For example, data 1705 is aggregated data from the ventilators 1750-1770 and is accessed by data accessor 1720. In certain aspects, at step 1815, data 1705 is automatically accessed from the ventilators 150-170. At step 1820, an aggregate of the data is analyzed. For example, data analyzer 1730 (or other components) analyzes data 1705. At step 1830, a ventilator operation trend of a ventilator is determined based on the analyzed aggregated data. For example, ventilator operation trend determiner 1735 determines ventilator operation trend 1736 based on analyzed data 1705. At step 1840, a ventilator operation of the ventilator 1750A is predicted based on the ventilator operation trend. For example, ventilator operation predictor 1737 predicts ventilator operation prediction 1738 based on ventilator operation trend 1736. At step 1850, a notification of the predicted ventilator operation is predicted based on one or more of the ventilator operation trend and the aggregated data. For example, notification generator 1740 generates notification 1741 of predicted ventilator operation based on ventilator operation trend 1736 and/or data 1705. At step 1860, a proactive treatment is provided to a patient associated with the ventilator based on the ventilator operation trend.

Ventilator Report Generation

Figure 19:
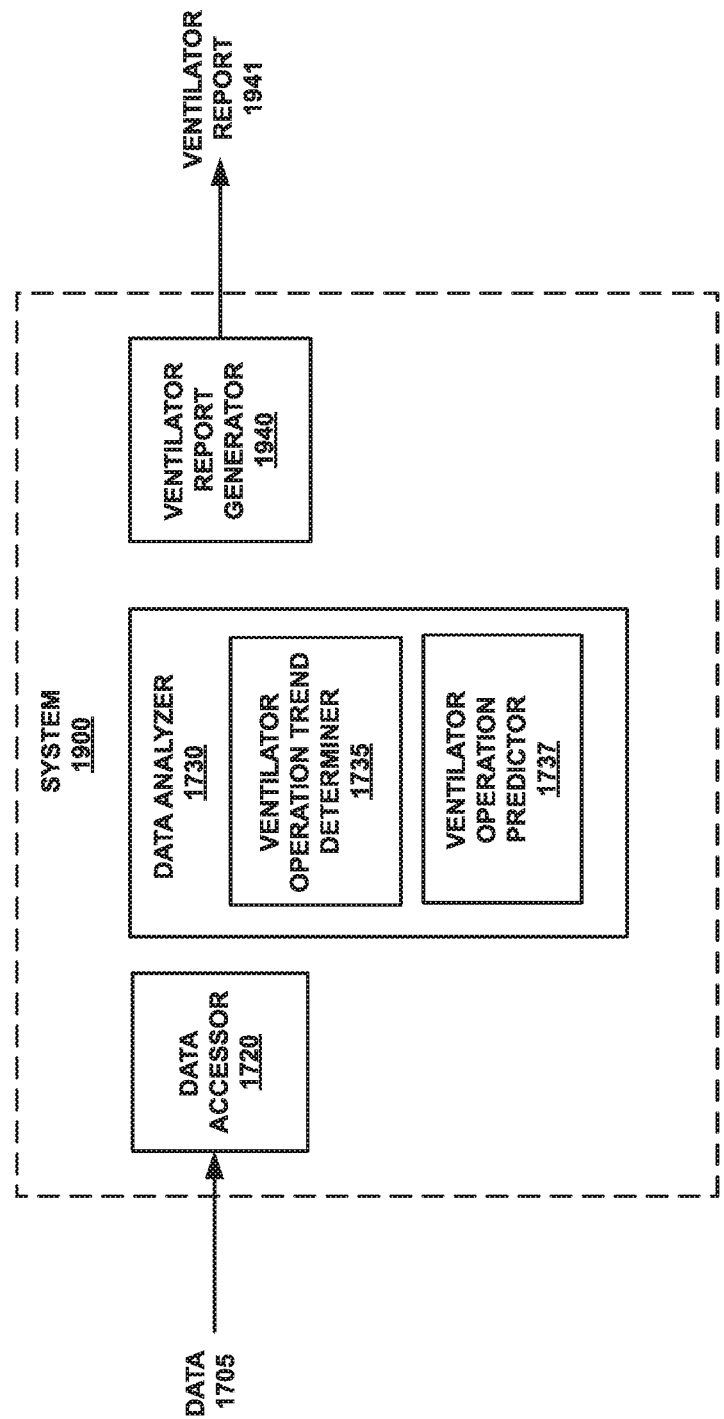

FIG. 19 depicts an embodiment of system 1900 for ventilation report generation, such as the weaning, medical ventilator settings, medical ventilator history, lung protection, and patient details reports discussed above. It should be appreciated that system 1900 is similar to system 1700, however, system 1900 includes ventilator report generator 1940 configured for generating report 1941. Ventilator report generator 1940 generates ventilator report 1941 for a ventilator based on the analyzed aggregated data.

Ventilator report 1941 can be a variety of different reports. In certain aspects, ventilator report 1941 includes a protocol compliance (or success analysis) report which compares the success of a ventilator protocol to other similar protocols. In such a report, the report is based on aggregated data of a plurality of ventilators (e.g., ventilators 1750-1770). In certain aspects, ventilator report 1941 includes a rounding report. Typically, a rounding report is for a clinician or caregiver and summarizes key information from a shift. As such, the rounding report allows for streamlined changeover at the end of a shift of one caregiver and the beginning of a shift of another caregiver. The rounding report can be generated as a service. In various embodiments, ventilator report 1941 can be based on trend analysis or comparison to aggregated ventilator information. For example, a report can compare best practice rules and/or protocols to collected data to determine discrepancies. Accordingly, the discrepancies are a part of the report.

Figure 20:
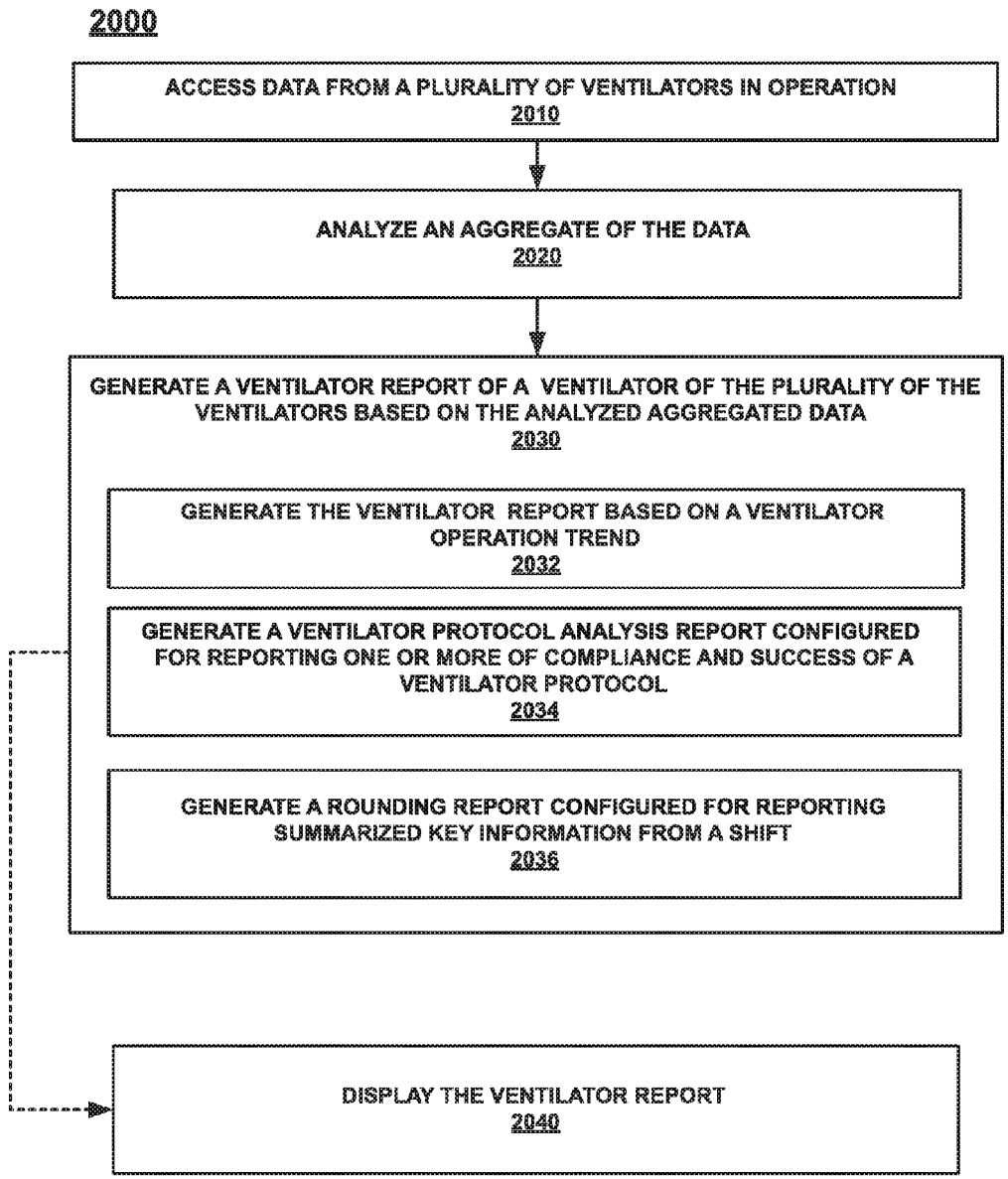
FIG. 20 illustrates an example method for generating a ventilator report.

FIG. 20 depicts an example method 2000 for generating a ventilator report. In various embodiments, method 2000 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2000 is performed at least by system 1900, as depicted in FIG. 19.

At step 2010 of method 2000, data 1705 is accessed from a plurality of ventilators in operation. At step 2020, an aggregate of the data is analyzed. At step 2030, a ventilator report of a ventilator is generated based on the analyzed aggregated data. For example, ventilator report generator 1940 generates ventilator report 1941 based on data 1705. At step 2032, the ventilator report based on a ventilator operation trend. For example, ventilator report generator 1940 generates ventilator report 1941 based on ventilator operation trend 1736. At step 2034, a ventilator protocol analysis report is generated and configured for reporting one or more of compliance and success of a ventilator protocol. At step 2036, a rounding report is generated and configured for reporting summarized key information from a shift. At step 2040, the ventilator report is displayed. For example, ventilator report is displayed on a ventilator 1750.

Suggesting Ventilator Protocols

Figure 21:
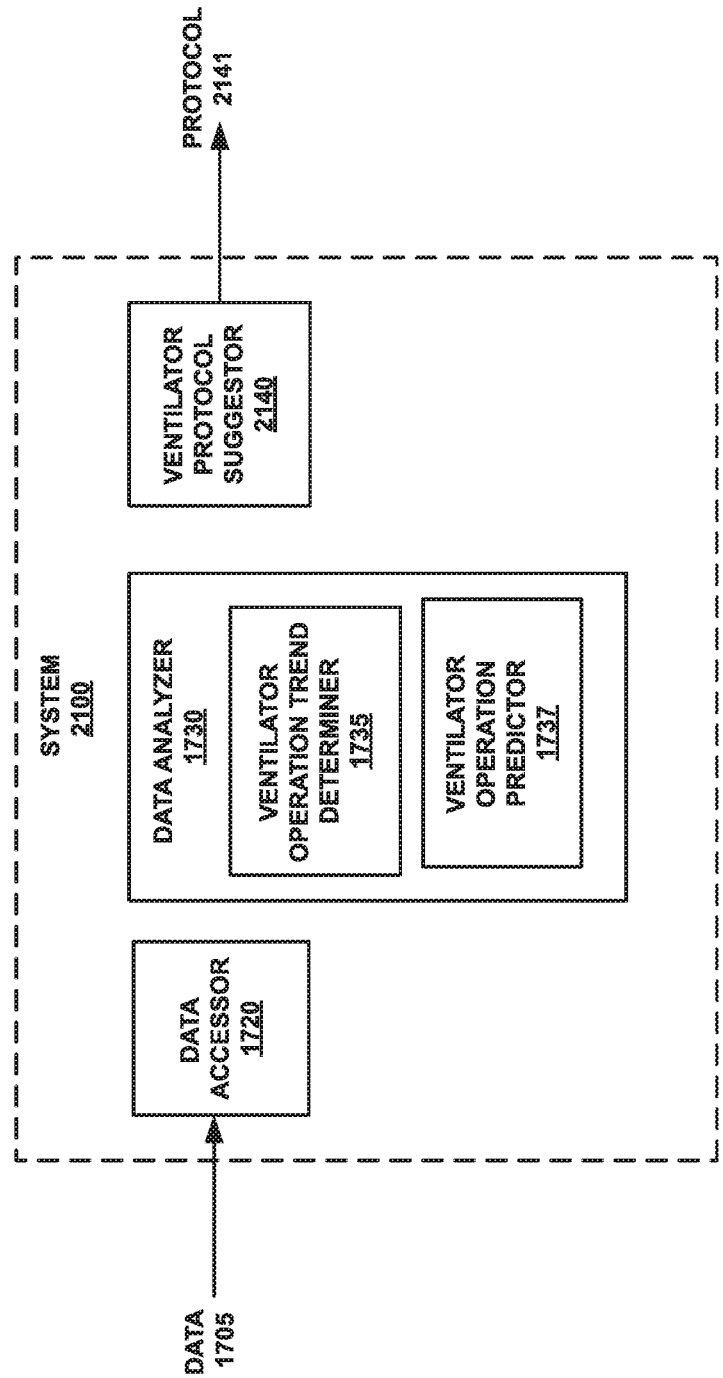

FIG. 21 depicts an embodiment of system 2100 for suggesting ventilator protocols. It should be appreciated that system 2100 is similar to system 1700, however, system 2100 includes ventilator protocol suggestor 2140 configured for suggesting protocol 2141. Ventilator protocol suggestor 2140 generates protocol 2141 for a ventilator 1750 based on the analyzed aggregated data.

In general, system 2100 receives patient information such as symptoms, medication, age, sex, weight. Accordingly, ventilator protocol suggestor 2140 suggests a protocol based on clinician based provided diagnostic information and a comparison of the patient information to aggregated ventilation outcome information. Protocol 2141 may be a variety of different protocols, such as, but not limited to, weaning, sedation, neonatal, $O_2$ settings, etc. In certain aspects, protocol 2141 is customizable. In various embodiments, protocol 2141 can be displayed on a display screen of a ventilator and/or forwarded to a hand-held interface or other network device.

Figure 22:
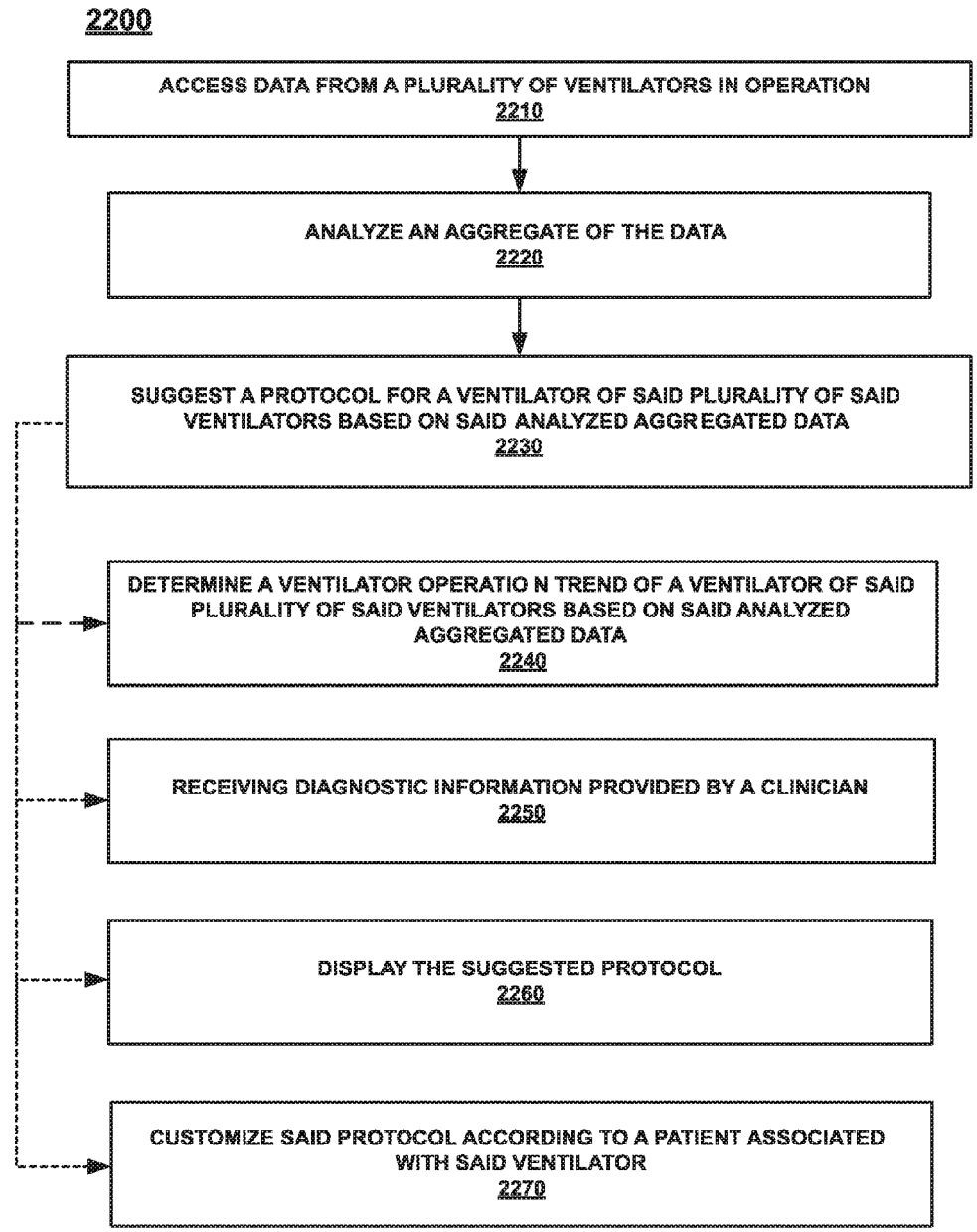
FIG. 22 illustrates an example method for suggesting ventilator protocols.

FIG. 22 depicts an example method 2200 for suggesting ventilator protocols. In various embodiments, method 2200 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2200 is performed at least by system 2100, as depicted in FIG. 21.

At step 2210 of method 2200, data is accessed from a plurality of ventilators in operation. At step 2220, an aggregate of the data is analyzed. At step 2230, a protocol for a ventilator is suggested based on the analyzed aggregated data. For example, ventilator protocol suggestor 2140 suggests protocol 2141 for a ventilator 1750. At step 2240, a ventilator operation trend is determined based on the analyzed aggregated data. At step 2250, diagnostic information provided by a clinician is received. For example, data accessor 1720 receives data 1705, which includes diagnostic information provided by a clinician. At step 2260, the protocol is displayed. For example, protocol 2141 is displayed on a display of a ventilator 1750. At step 2270, the protocol is customized according to a patient associated with the ventilator. For example, protocol 2141 is customized according to a patient associated with ventilator 1750.

Ventilation Harm Index

Figure 23:
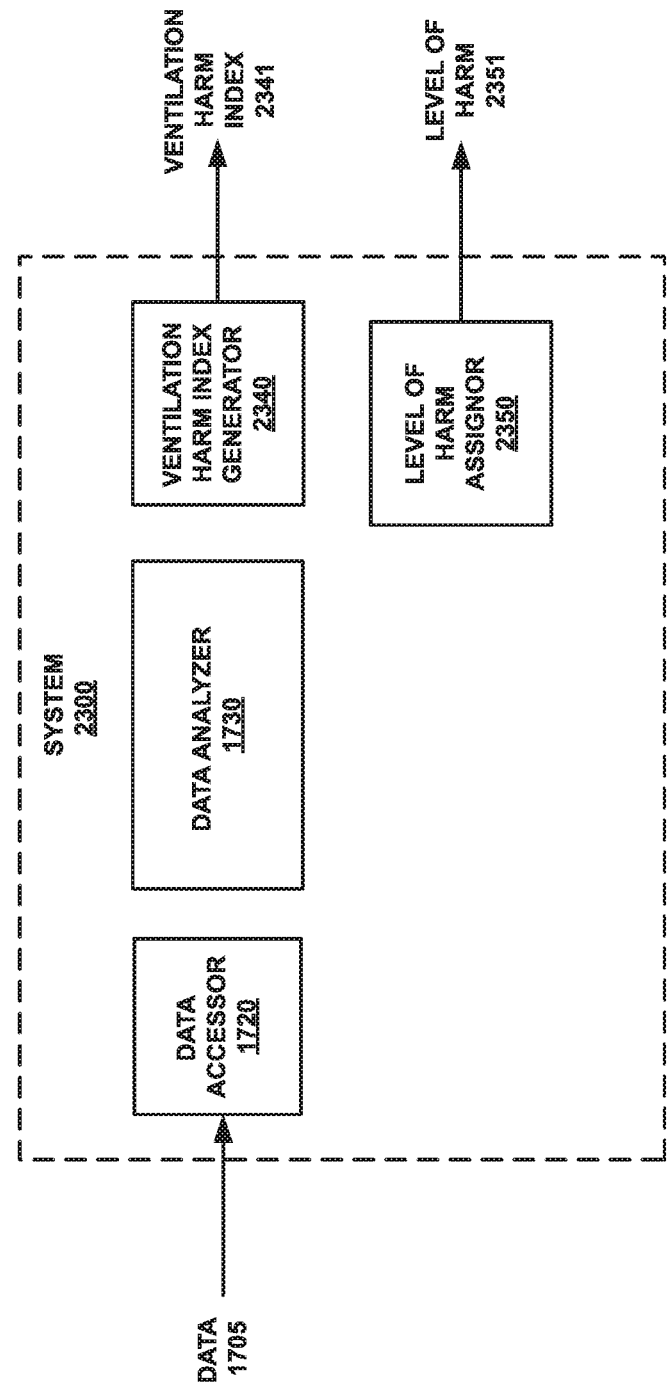

FIG. 23 depicts an embodiment of system 2300 for generating a ventilation harm index. It should be appreciated that system 2300 is similar to system 1700, however, system 2300 includes ventilation harm index generator 2340 and level of harm assignor 2350. Ventilation harm index generator 2340 generates ventilation harm index 2341 based on the analyzed aggregated data or outcomes from the plurality of ventilators. In various embodiments, ventilator harm index 2341 can be viewed on the hosted or deployed user interface. Level of harm assignor 2350 is configured for assigning a level of harm 2351 to a ventilator setting. Typically, a ventilator is able to perform a plurality of operations that are adjusted or controlled by ventilator settings. The ventilator settings may include, for example, time of ventilation at various levels or level of oxygen. During use, when a clinician attempts to set or adjust the operation of the ventilator by inputting a ventilator setting, a level of harm 2351 is assigned to the attempted input or change of ventilator setting. The level of harm 2351 is displayed or presented to the clinician in response to the attempted input or change of ventilator setting. In various embodiments, the level of harm 2351 includes a degradation of low, medium or high level of harm. It should be appreciated that the level of harm may have other degradations.

In certain aspects, there may be a delayed implementation of the ventilator setting (e.g., three seconds) to allow the clinician to cancel the ventilator setting because the level of harm assigned to the setting was high. In certain aspects, the clinician may be presented with the level of harm and then required to verify the setting. In such an embodiment, the verification may be required for certain levels of harm. In a further embodiment, for certain harm index levels, only certain personnel may be allowed to initiate the setting/adjustment of the ventilator 1750. This could be assured, for example, by some form of clinician identification or logon.

Figure 24:
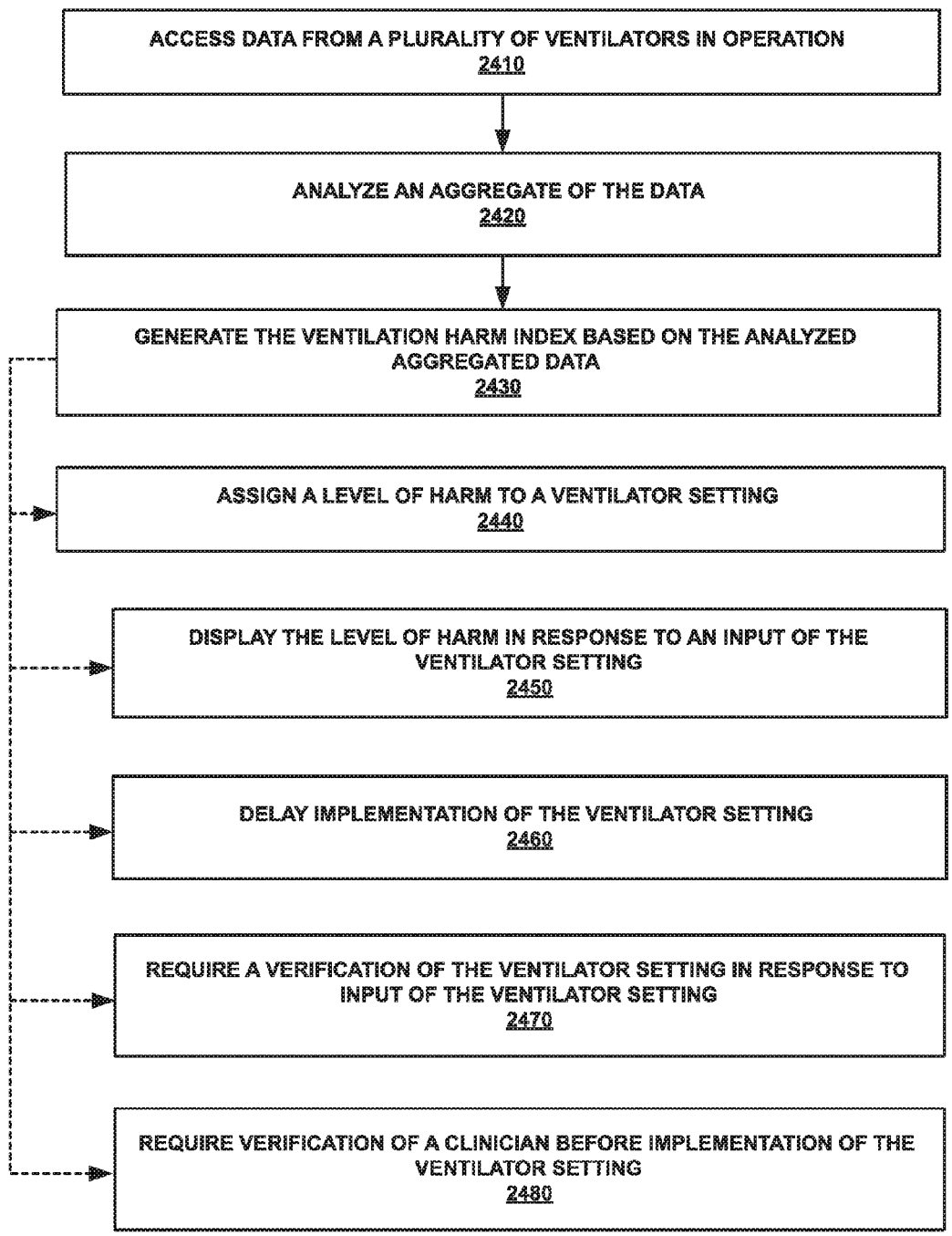
FIG. 24 illustrates an example method for generating a ventilation harm index.

FIG. 24 depicts an example method 2400 for generating a ventilation harm index. In various embodiments, method 2400 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2400 is performed at least by system 2300, as depicted in FIG. 23.

At step 2410 of method 2400, data is accessed from a plurality of ventilators in operation. At step 2420, an aggregate of the data is analyzed. At step 2430, the ventilation harm index is generated based on the analyzed aggregated data. For example, ventilation harm index generator 2340 generates ventilation harm index 2341. At step 2440, a level of harm is assigned to a ventilator setting. For example, a high level of harm is assigned to a certain level of oxygen setting. At step 2450, the level of harm is displayed in response to an input of the ventilator setting. For example, a clinician adjusts the level of oxygen setting and the level of harm is displayed in response to the adjustment. At step 2460, implementation of the ventilator setting is delayed. For example, the level of oxygen is substantially increased, and as a result, the implementation of the increased level of oxygen is delayed such that the clinician can correctly adjust the level of oxygen. At step 2470, a verification of the ventilator setting is required in response to input of the ventilator setting. For example, the level of oxygen is substantially increased, and as a result, a verification of the ventilator setting is required to ensure that the level of oxygen change is correct. At step 2480, verification of a clinician is required before implementation of the ventilator setting. For example, certain ventilator settings are only allowed by certain verified clinicians.

Ventilator Avoidance Report

Figure 25:
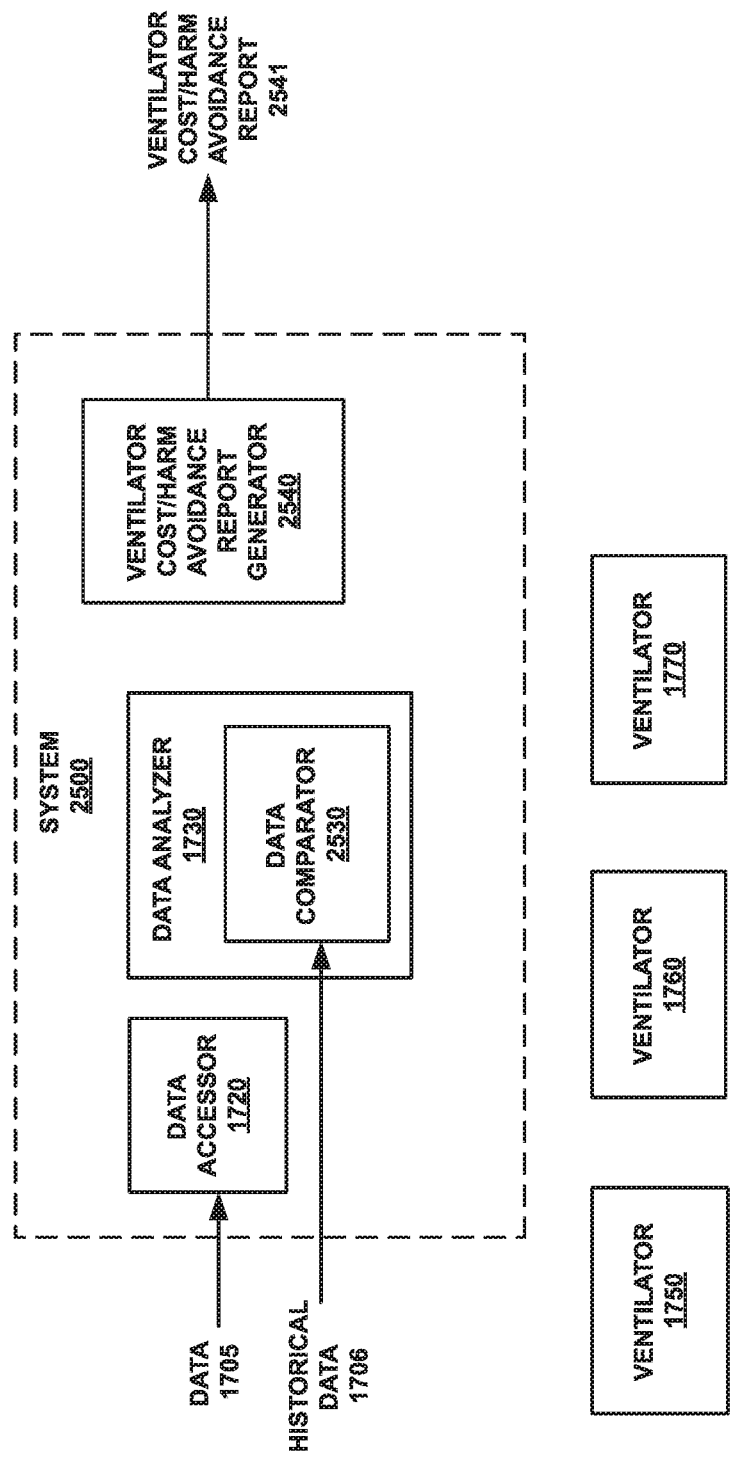

FIG. 25 depicts an embodiment of system 2500 for generating a ventilator avoidance report. In certain aspects, system 2500 is similar to system 1700, however, system 2500 includes data comparator 2530 and a report generator (e.g., cost/harm avoidance report generator 2540) configured to generate a ventilator avoidance report (e.g., ventilator cost/harm avoidance report 2541). During use of system 2500, data accessor 1720 accesses data 1705 from a ventilator (e.g., ventilator 1750) during operation. Data 1705 may be any operation data from the ventilator. For example, data 1705 may be associated with any protocol and/or customizable protocol.

Data comparator 2530 compares data 1705 with historical data 1706. Historical data 1706 is any operational data associated with one or more other ventilators. For example, historical data 1706 can include empirical data, rules of thumb, protocols, or operational history. In various embodiments, historical data 1706 can also include hospital costs, such as, reimbursement, cost to ventilate a patient, or labor expenses. Ventilator 1750 may be similar to the other ventilators (e.g., ventilator 1760 and 1770). However, ventilator 1750 is distinguished or different than the other ventilators in some way. For example, ventilator 1750 may be an upgraded version of ventilator 1760 and/or 1770. Data comparator 2530 compares data 1705 with associated historical data from at least one other ventilator. For example, data comparator compares operation data of ventilator 1750 with historical operation data from another ventilator. In such an example, data comparator 2530 compares the results of protocols related to oxygen levels of ventilator 1750 with results of protocols related to oxygen levels of other ventilators.

Report generator 2540 generates ventilator avoidance report 2541 based on the comparison of data comparator 2530. The ventilator avoidance report can describe the costs and/or harm that are avoided by utilizing ventilator 1750 rather than ventilators 1760 and/or 1770. The avoidance of costs can describe the amount of money saved, hospitalization days saved, etc. Moreover, because hospital beds may be scarce commodities, the report can help make the case for the use of ventilator 1750 rather than ventilators 1760 and/or 1770. The ventilator avoidance report can capture or record harms avoided based on a variety of factors, such as, shorter hospitalization, faster weaning (versus a basic ventilator), number of times that ventilator rules prevented danger to a patient and what the likely outcome would have been (e.g., additional hospitalization, longer ventilation, death, etc.). As a result, the report helps make the case for the benefits of ventilator 1750 versus basic ventilators (e.g., ventilators 1760 and/or 1770) by preventing harms (which would also save money). In certain aspects, ventilator avoidance report 2541 describes how much money was saved by getting the patient off of the ventilator sooner versus a basic ventilator.

Figure 26:
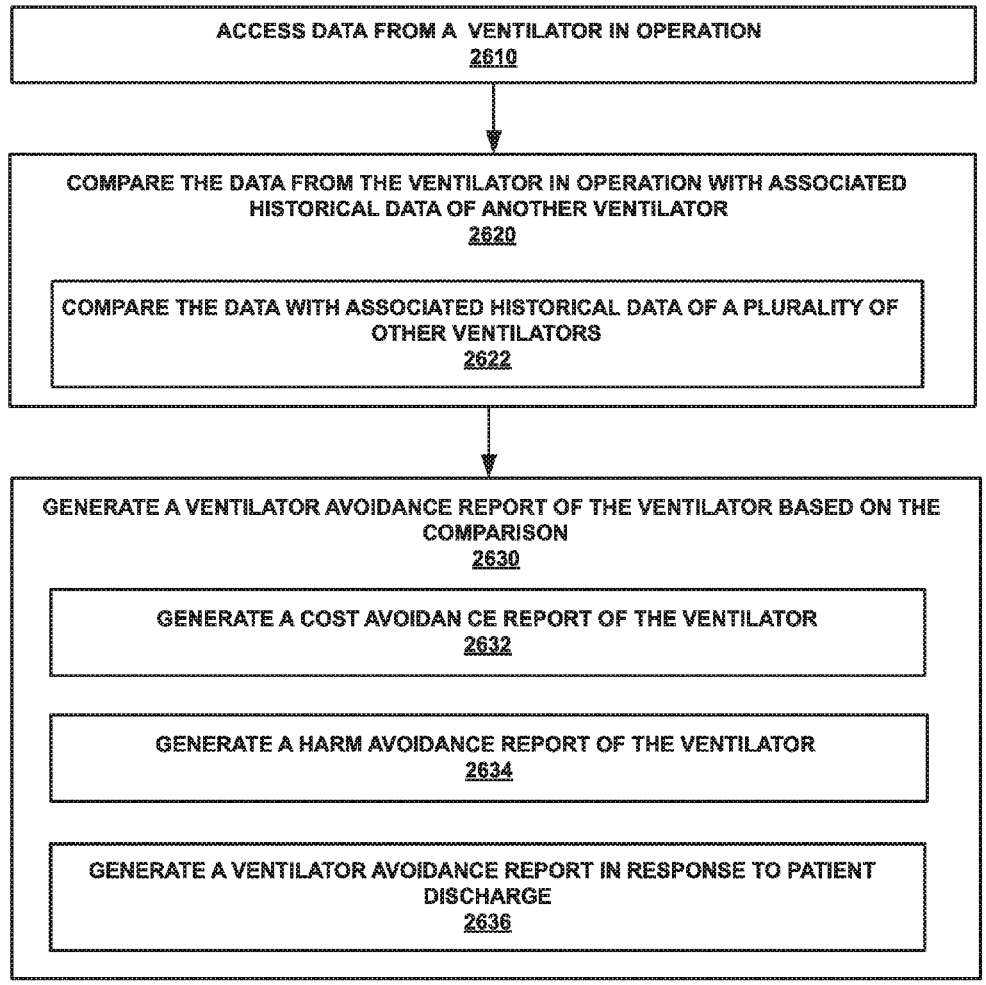
FIG. 26 illustrates an example method for generating a ventilator avoidance report.

FIG. 26 depicts an example method 2600 for generating a ventilator avoidance report. In various embodiments, method 2600 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2600 is performed at least by system 2500, as depicted in FIG. 25.

At step 2610 of method 2600, data is accessed from a ventilator in operation. For example, data 1705 is accessed from the ventilator 1750 by data accessor 1720. At step 2620, the data from the ventilator in operation is compared with associated historical data of another ventilator. For example, data 1705 (e.g., oxygen level data) of ventilator 1750 is compared with associated historical data 1706 (e.g., oxygen level data) of ventilator 1760. At step 2622, the data is compared with associated historical data of a plurality of other ventilators. For example, data 1705 (e.g., oxygen level data) of ventilator 1750 is compared with associated historical data 1706 (e.g., oxygen level data) of ventilators 1760 and 1770. At step 2630, a ventilator avoidance report of the ventilator is generated based on the comparison. For example, report generator 2540 generates avoidance report 2541 based on the comparison by data comparator 2530. At step 2632, a cost avoidance report is generated. At step 2634, a harm avoidance report is generated. In a further embodiment, a ventilator avoidance report is generated in response to a patient being discharged from the hospital or having the ventilation services end.

Assisting Ventilator Documentation at a Point of Care

Typically, ventilator documentation is executed manually by a clinician and/or executed at a computer system that is in another location than the point of care (e.g., immediate location of ventilator and/or patient). Accordingly, the work flow of ventilator documentation is inefficient. Moreover, human error, such as incorrect transcribing, may occur.

Figure 27:
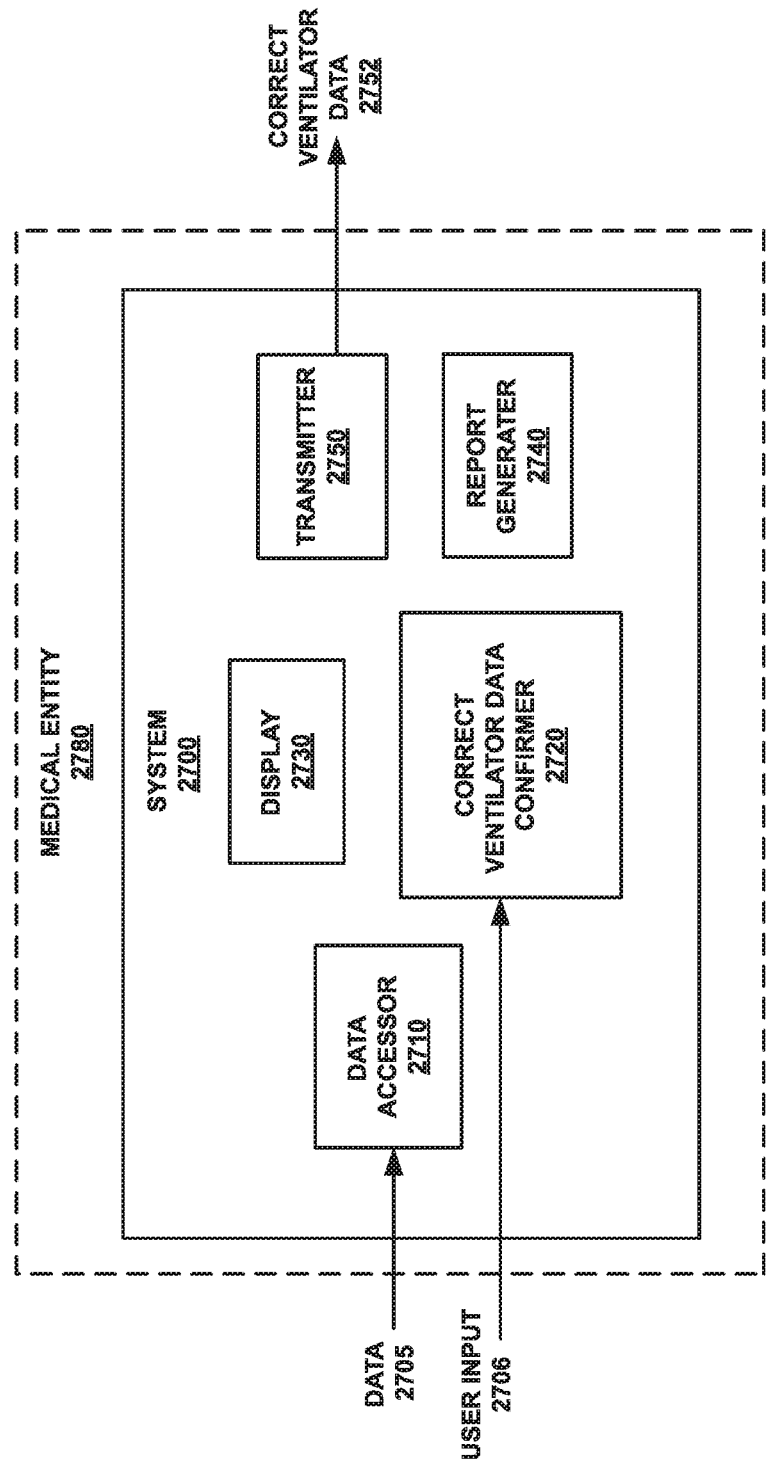

FIG. 27 depicts an embodiment of system 2700 for assisting ventilator documentation at a point of care. In general, system 2700 facilitates a more efficient, accurate, and/or timely method of documentation at a point of care. System 2700 includes data accessor 2710, correct ventilator data confirmer 2720, display 2730, report generator 2740, and transmitter 2750. Data accessor 2710 is configured to access data 2705. Data 2705 can be any ventilator data associated with a ventilator. For example, data 2705 is streaming (e.g., full) ventilator data or a snapshot of ventilator data that can be annotated for the rounds with patient vitals (e.g., breath sounds) and observations (e.g., patient orientation, rescue equipment is near point of care). Data 2705 can also include any information that facilitates in ventilator documentation. For example, data 2705 can include ventilator parameters, medication treatment (e.g., assess breathing before and after treatment), ventilator changes, or weaning. Data 2705 can be accessed directly from the ventilator 1750 or can be accessed from a medical entity such as a healthcare facility network, user interface, etc. In certain aspects, data 2705 includes any data associated with any another medical device that is associated with the ventilator 1750 and/or patient. Data 2705 is displayed on display 2730. For example, data 2705 is pre-populated into a ventilator documentation format.

Correct ventilator data confirmer 2720 is configured for confirming that ventilator data is correct at point of care based on user input. For example, data 2705 is displayed on display 2730 for viewing by a clinician. The data is used to generate ventilation documentation. The clinician reviews and signs off that the ventilation documentation is correct and thereby confirms whether or not that ventilation documentation is correct. The confirmed correct ventilation documentation at the point of care improves the accuracy of the ventilation documentation. The accuracy is improved, for example, because transcribing is not required, and the ventilation documentation information is prepopulated and the clinician verifies the documentation, if correct, at the point of care.

Transmitter 2750 is configured to transmit correct ventilator data 2752 (e.g., signed off ventilation documentation). In certain aspects, correct ventilator data 2752 is transmitted to a patient medical record, for example, in EMAR formant (e.g., level 7 compatible interface). Report generator 2740 is configured to generate reports based on correct ventilator data 2752. In certain aspects, report generator 2740 generates a round report based on correct ventilator data 2752. In certain aspects, system 2700 is disposed or integrated in medical entity 2780. In certain aspects, medical entity 2780 is a ventilator. In certain aspects, medical entity 2780 is configured to connect to a handheld device (e.g., handheld computer, tablet, PDA, etc.). In such an embodiment, the handheld device can wirelessly communicate with a ventilator over WiFi, short range wireless, WPAN, or cellular network. System 2700 can also be utilized for caregiver verification for login/access to a ventilator (e.g., ventilator 110, ventilator 710, etc.). The verification may be authorized by a caregiver identifier obtained by a card, barcode, or biometric input.

Figure 28:
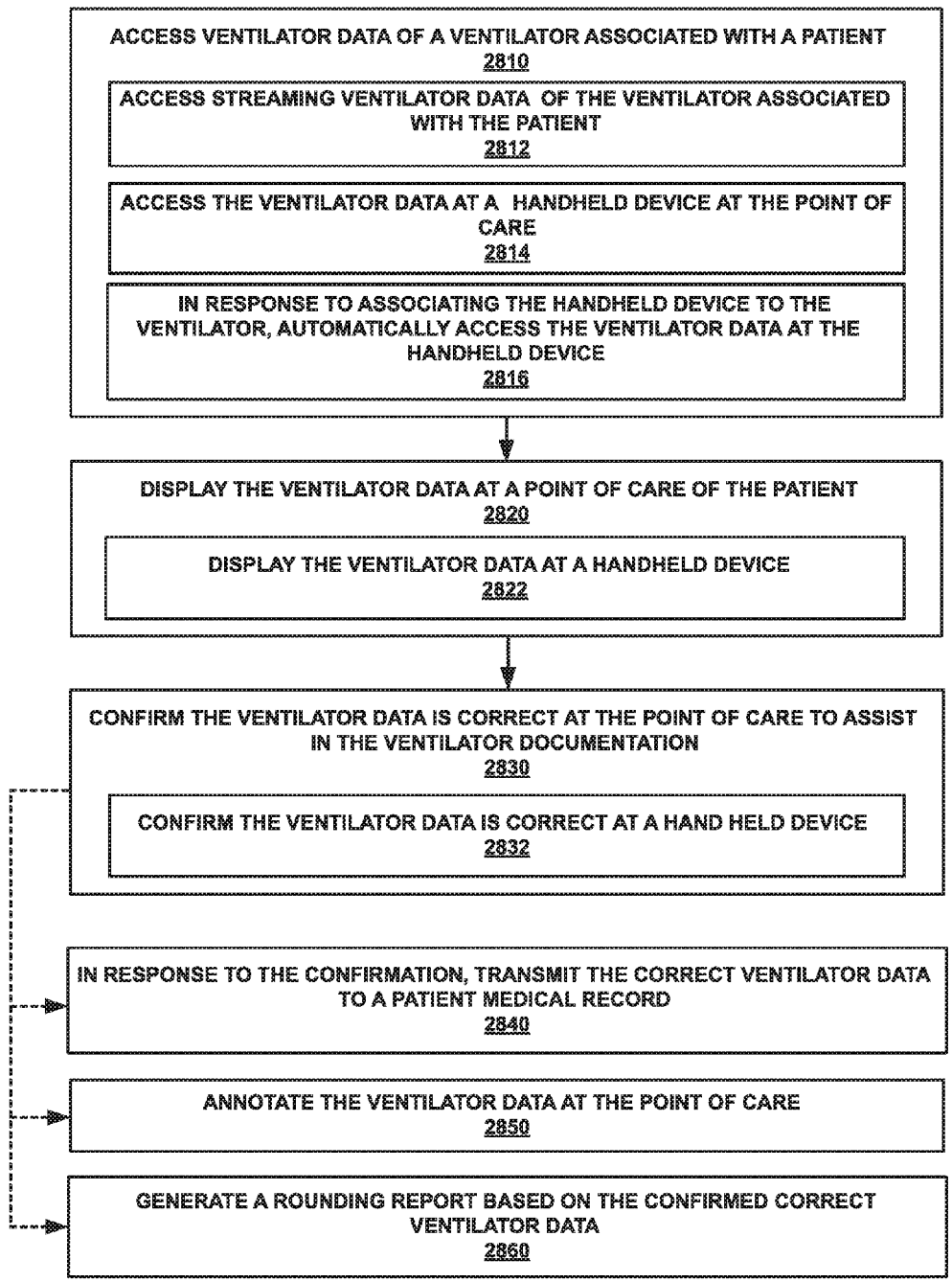
FIG. 28 illustrates an example method for assisting ventilator documentation at a point of care.

FIG. 28 depicts an example method 2800 for assisting in ventilator documentation at a point of care. In various embodiments, method 2800 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2800 is performed at least by system 2700, as depicted in FIG. 27.

At step 2810, ventilator data of a ventilator associated with a patient is accessed. For example, data 2705 that is associated with a ventilator and a patient is accessed by data accessor 2710. At step 2812, streaming ventilator data of ventilator associated with the patient is accessed. For example, data accessor 2710 accesses or captures streaming (full) ventilator data from the ventilator. In other words, data accessor 2710 captures data 2705 which is in real-time. At step 2814, the ventilator data is accessed at a handheld device at the point of care. For example, system 2700 is implemented in a handheld device. Therefore, data 2705 is accessed at the handheld device at the point of care. At step 2816, in response to associating the handheld device to the ventilator, the ventilator data at the handheld device is automatically accessed. For example, a handheld device (including system 2700) is associated with the ventilator, for example, by scanning a barcode on the ventilator. As a result the handheld device is synced to the ventilator. In response to the association, all available vitals are automatically accessed and coupled to the handheld device. At step 2820, the ventilator data is displayed at a point of care of the patient. For example, a ventilator (including system 2700) displays data 2705 on display 2730. In certain aspects, at step 2832, the ventilator data is displayed at the point of care on a handheld device. For example, a handheld client device 130 associated with a clinician displays data 2705 on display 2730.

At step 2830, the ventilator data is confirmed to be correct at the point of care to assist in the ventilator documentation. For example, a clinician reviews data 2705 that is utilized to form ventilator documentation. If the displayed data is correct for proper ventilator documentation, then the clinician confirms the propriety of the ventilator documentation by generating user input 2706. At step 2832, the ventilator data is confirmed to be correct at a handheld device. For example, the clinician confirms the propriety of the ventilator documentation by generating user input 2706 at the handheld device. At step 2840, in response to the confirmation, the correct ventilator data is transmitted to a patient medical record. For example, transmitter 2750 transmits correct ventilator data 2752, corresponding to a proper and correct ventilator documentation, to a patient medical record. At step 2850, the ventilator data is annotated at the point of care. For example, data 2705 displayed on display 2730 is annotated by a clinician. In such an example, the clinician annotates or inputs data about weaning, change of ventilator, etc. At step 2860, a rounding report based on the confirmed correct ventilator data is generated. For example, report generator 2740 generates a rounding report based on correct ventilator data 2752.

Example System

Figure 29:
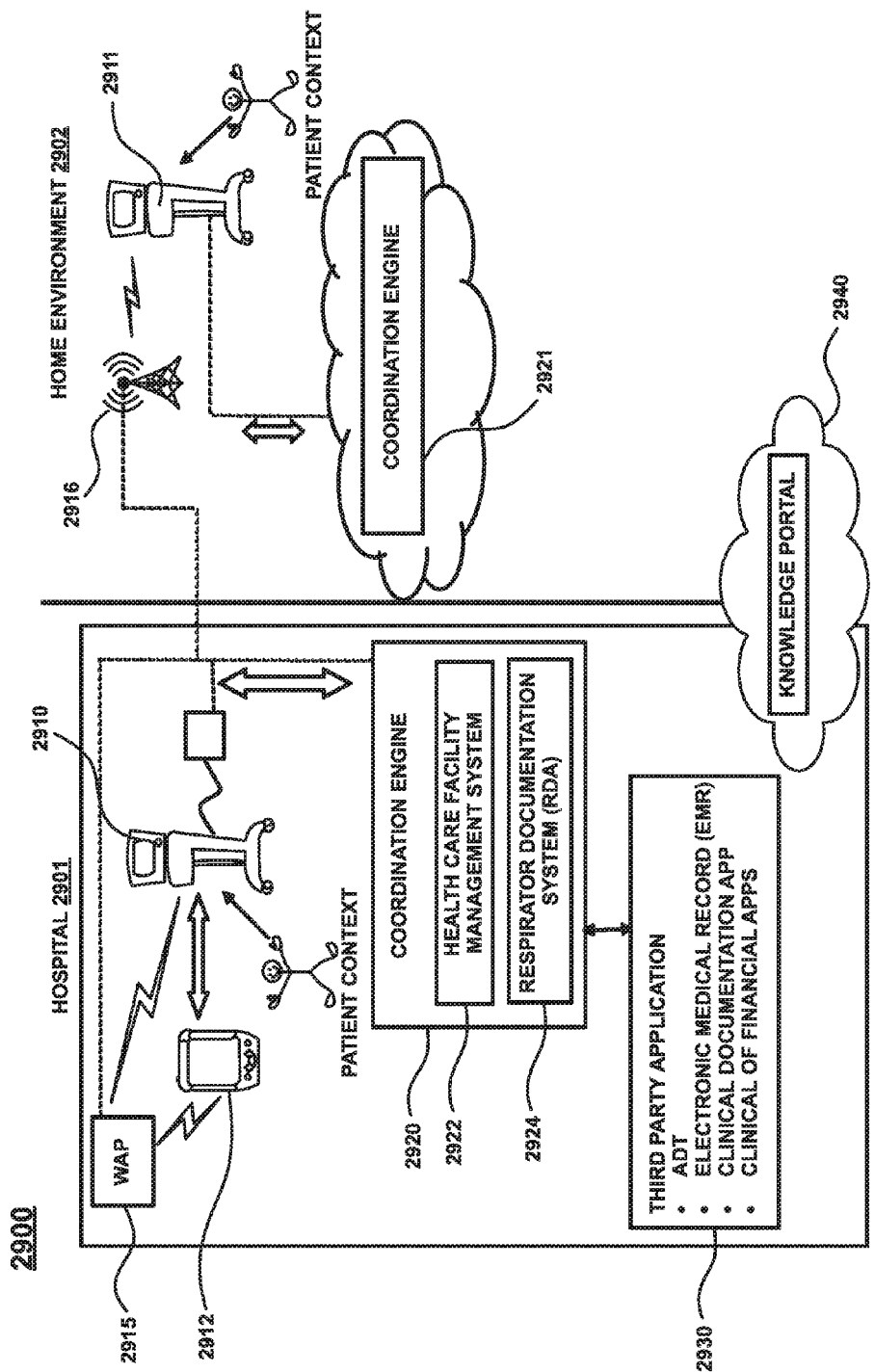

FIG. 29 depicts an example medical system 2900. In various embodiments, medical system 2900 includes variations and combinations of devices, systems, methods described in detail above.

Medical system 2900 includes a hospital 2901 and/or home environment 2902. In certain aspects, hospital 2901 includes ventilator 2910 (e.g., ventilator 110, ventilator 710, etc.) that bi-directionally communicates with medical entities in a network (e.g., WAN). For example, ventilator 2910 bi-directionally communicates with coordination engine 17020, third party application 2930, knowledge portal 2940, handheld device 2912, etc. Ventilator 2910 can wirelessly connect to the network via WAP 2915. In certain aspects, home environment 2902 includes ventilator 2911 (e.g., ventilator 110, ventilator 710, etc.) that bi-directionally communicates with medical entities. For example, ventilator 2911 bi-directionally communicates with medical entities in the network of hospital 2901 (as described above) via cellular network 2916 and/or with coordination engine 2921. In certain aspects, system 2900 allows for contextualizing ventilator data (e.g., patient context) for ventilators 2910 and 2911, as described above with respect to FIGS. 4-6.

Coordination engine 17020 and 2921 include an interface for third party applications (e.g., third party applications 2930). For example, ventilator 2910 may access ADT information from a third party ADT via coordination engine 17020. It should be appreciated that the coordination engines can be integrated in a single location, such as a server, or can be distributed across various computer devices/systems. Third party applications 2930 can include, but are not limited to, an ADT application, electronic medical record (EMR) application, clinical documentation application, or various clinical or financial applications. In various embodiments, ventilators 2910 and/or 2911 may bi-directionally communicate with various applications associated with coordination engine 17020 (or coordination engine 2921). For example, ventilator 2910 bi-directionally communicates with healthcare facility management system 2922.

In certain aspects, ventilator 2910 bi-directionally communicates with respiratory documentation system or application (RDA) 2924. It should be appreciated that the RDA can also run on other medical devices such as handheld device 2912. In various embodiments, the ventilators are capable of ventilator data logging. For example, ventilator 2911 may be offline, however, it is still able to capture and store data. Once the ventilator comes back online the stored data is transmitted to medical entities such as coordination engine 2921.

Ventilator Suction Management

Figure 30:
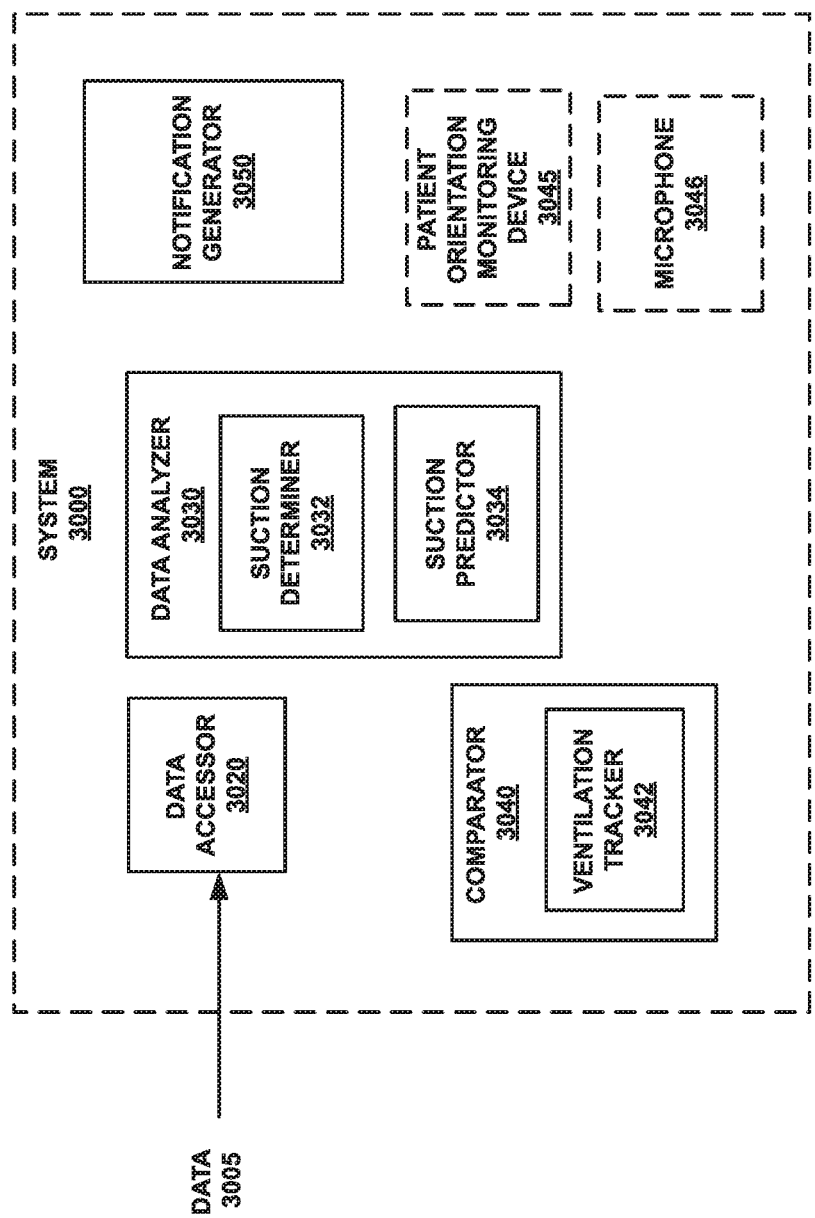

FIG. 30 depicts an embodiment of system 3000 for ventilator suction management. In general, ventilator suction management is for the control/management of suction, by a ventilator, on a patient associated with the ventilator. System 3000 includes data accessor 3020, data analyzer 3030, comparator 3040, and, optionally, patient orientation device 3045, and microphone 3046.

Data accessor 3020 is configured to access data 3005. Data 3005 can be any data or information associated with a patient who is being treated by a ventilator (e.g., ventilator 110, ventilator 710, etc.). Data 3005, can be, but is not limited to, ventilator data, trending of ventilator data, contextualized patient data from ADT/lab reports, or patient vitals. In various embodiments, data 3005 can be the output of patient orientation monitoring device 3045 and/or microphone 3046. Patient orientation monitoring device 3045 is configured for monitoring the orientation of a patient associated with the ventilator. For example, patient orientation monitoring device 3045 monitors whether the patient is on his/her side, back stomach, etc in certain aspects, patient orientation monitoring device 3045 is configured for monitoring patient orientation to facilitate in the determining whether or not suction is needed on a patient, which will be described below. For example, suction is needed less often when a patient is oriented on his or her stomach. Microphone 3046 is configured for capturing or sensing breathing sounds of the patient (e.g., wheezing) to facilitate in the determining whether or not suction is needed on a patient, which will be described below.

Data analyzer 3030 receives data 3005 and analyzes data 3005 for ventilator suction management. In particular, data analyzer 3030 includes suction determiner 3032 and suction predictor 3034. Suction determiner 3032 is configured for determining that suction is needed on the patient based on the analyzed data. For example, based on a patient oriented on his or her back, suction determiner 3032 determines that suction is presently needed for the patient. In response to the determination, suction is performed on the patient based on data 3005. It should be appreciated that the term "suction," as used herein, pertains to any ventilator suction event, for example, the suction of saliva or mucous from the airway of a patient, by a ventilator.

Notification generator 3050 is configured for generating a notification for when suction is needed or required. For example, when suction determiner 3032 determines that suction is presently needed, notification generator 3050 generates a notification that the suction is presently needed. This notification assists the caregiver that the suction is needed and/or to be performed. It should be appreciated that the notification can be, but is not limited to, a message on the screen of the ventilator, sound, light, notice at the nursing station, or a page to the caregiver/respiratory therapist. Suction predictor 3034 is configured for predicting a time when suction is needed and/or to be performed on the patient based on the analyzed data. In certain aspects, if suction determiner 3032 determines that suction is not presently needed for a patient, then suction predictor 3034 will predict a time (e.g., in the future) when suction will be needed for the patient based on the analyzed data. In various embodiments, predicting when suction will be needed is a mode of operation which may automatically engage or be manually engaged. As a result of the predicted time of suction, rounds or visits of a caregiver can be scheduled to coincide with the predicted time for suction.

Comparator 3040 is configured for comparing patient ventilation prior to suction to patient ventilation after suction. Ventilation tracker 3042 is configured for tracking patient ventilation after suction. In particular, once suction is performed on the patient, ventilator tracker 3042 tracks the patient's respiratory health following the suction. Comparator 3040 compares the patient ventilation prior to suction to patient ventilation after suction to facilitate in determining whether or not the suction improved patient ventilation. If the patient ventilation is improved, the tracking/comparing also determines how effective the suction was at improving ventilation. As a result, the caregiver is able to determine if suction was warranted and/or how effective the suction was at improving ventilation.

Figure 31:
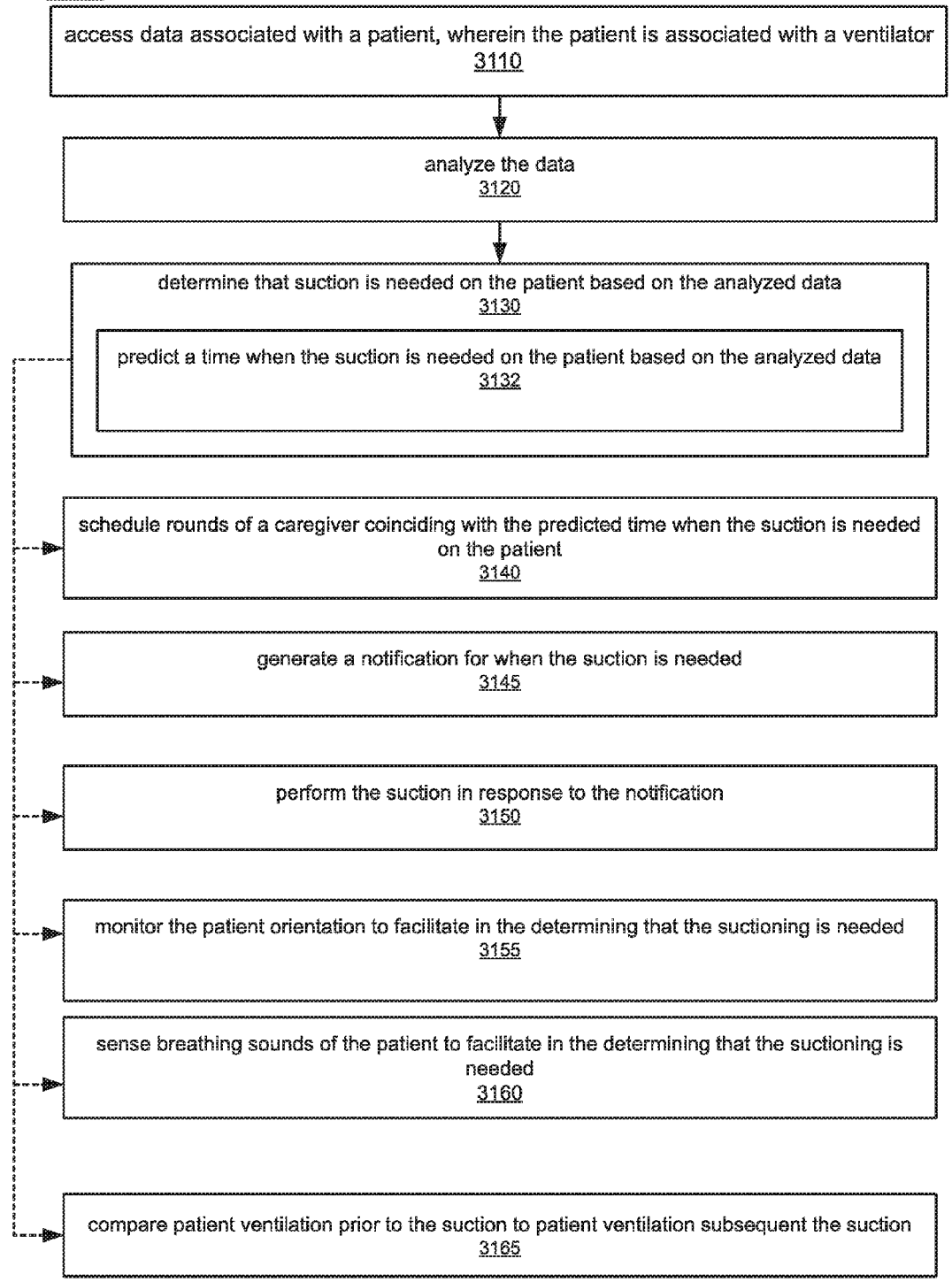
FIG. 31 illustrates an example method for ventilation suction management.

FIG. 31 depicts an embodiment of method 3100 for ventilation suction management. In various embodiments, method 3100 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 3100 is performed at least by system 3000, as depicted in FIG. 30.

At step 3110, data associated with a patient is accessed, wherein the patient is associated with a ventilator. For example, data 3005 (e.g., breathing sounds, patient orientation, contextualized data, etc.) that is associated with a patient is accessed by data accessor 3020. In particular, the patient is receiving respiratory care from a ventilator (e.g., ventilator 110). At step 3120, the data is analyzed. For example, data 3005 is analyzed by data analyzer 3030. At step 3130, suction is determined to be needed on the patient based on the analyzed data. For example, suction determiner 3032 determines that a patient is in need of suction based on data 3005. It should be appreciated that suction may be actually performed on the patient subsequent the determination that suction is needed. At step 3132, a time is predicted when the suction is needed on the patient based on the analyzed data. For example, suction predictor 3034 predicts a time when suction is needed on the patient based on data 3005, such as contextualized data. At step 3140, rounds of a caregiver are scheduled to coincide with the predicted time when the suction is needed on the patient. For example, suction predictor 3034 predicts that suction is needed for a patient at 12:00 PM. Accordingly, a round of a caregiver is scheduled to coincide with the predicted suction at 12:00 PM. At step 3145, a notification is generated for when the suction is required. For example, suction determiner 3032 determines that a patient is in need of suction at the present time (e.g., 1:00 PM). Accordingly, notification generator 3050 generates a notification (e.g., beep, text) at 1:00 PM to notify a caregiver that suction is needed for the patient. At step 3150, suction is performed in response to the notification. For example, suction is automatically performed on the patient in response to notification generator 3050 generating a notification that suction is needed. At step 3155, the patient orientation monitored to facilitate in the determining that suction is needed. For example, a patient is determined to be oriented on his back, based on patient orientation monitoring device 3045. Accordingly, suction determiner 3032 determines that suction is needed and/or to be performed. At step 3160, breathing sounds of the patient are sensed to facilitate in the determining that the suctioning is needed. For example, wheezing sounds of the patient are captured by microphone 3046. Accordingly, suction determiner 3032 determines that suction is needed. At step 3165, patient ventilation prior to the suction is compared to patient ventilation subsequent the suction. For example, comparator 3040 compares patient ventilation prior to suction to patient ventilation subsequent the suction, to facilitate in determining the effectiveness of the suction.

Remotely Accessing a Ventilator

Figure 32:
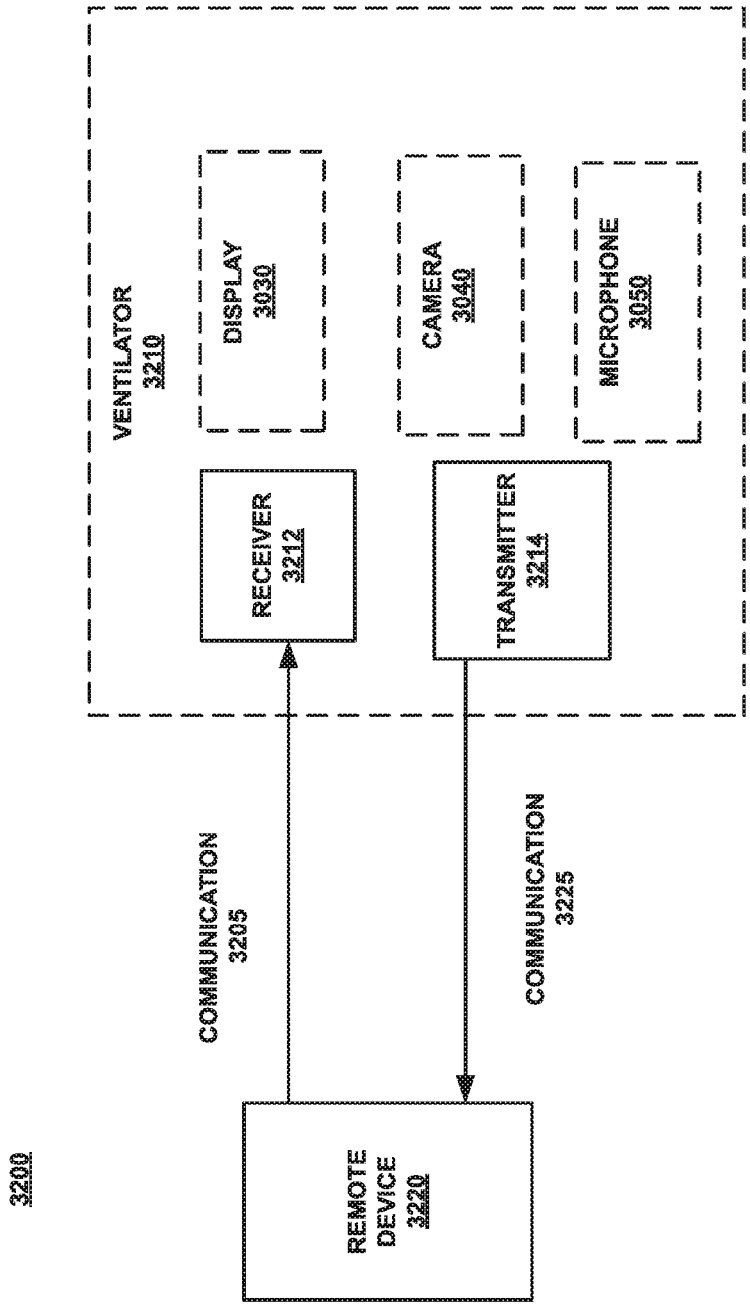

FIG. 32 depicts an embodiment of system 3200 for remotely accessing a ventilator. System 3200 includes ventilator 3210 and remote device 3220. It should be appreciated that system 3200 is similar to system 100, as described above. It should also be appreciated that ventilator 3210 has similar structure and functionality as other ventilators described herein, such as ventilator 110 and ventilator 710.

In general, remote device 3220 is able to remotely communicate (e.g., bi-directionally communicate) with ventilator 3210. For example, ventilator 3210, which is in a home environment (e.g., home environment 2902 of FIG. 29) is able to bi-directionally communicate with remote device 3220, which is in a hospital (e.g., hospital 2901 of FIG. 29). In various embodiments, system 3200 can include one or more ventilators that are able to bi-directionally communicate with one or more medical entitles or other ventilators, which may be at the same or different remote locations. Ventilator 3210 includes receiver 3212, transmitter 3214 and optionally, display 3031, camera 3040 and microphone 3050. Receiver 3212 is configured for receiving communication from 3205 from remote device 3220. Communication 3205 can be any information or data that facilitates in managing/controlling ventilator 3210 and/or providing respiratory care to the patient. In certain aspects, communication 3205, received by receiver 3212, is a request to remotely access ventilator data of ventilator 3210, for example, a request from a caregiver.

In certain aspects, communication 3205 is streaming video (which also includes audio) that is displayed on display 3030 (e.g., a touch screen display). Accordingly, the patient is able to view the video and communicate in real-time with the caregiver. In various embodiments, communication 3205 (or remote caregiver data) can be, but is not limited to, instructions that remotely control ventilator 3210 or suggestions/instructions regarding ventilator setting/protocols. Communication 3225 can be any information or data (e.g., ventilator data) that facilitates in providing respiratory care to the patient. For example, transmitter 3214 transmits ventilator data to remote device 3220 such that a caregiver is able to review the ventilator data. In certain aspects, communication 3225 is streaming video of a patient captured by camera 3040. The streaming video is displayed at the remote device, such that the caregiver is able to communicate in real-time with the patient.

In certain aspects, communication 3225 is audio of the patient captured by microphone 3050. For example, a caregiver may listen to the breathing sounds which are transmitted to and received by remote device 3220. The bi-directional communication between remote device 3220 and ventilator 3210, as described above, allows for a variety of remote caregiving features. For example, a remote caregiver can listen to and see the patient and may discuss patient matters with an on-site caregiver, images may be presented to the patient at display 3030 and/or at remote device 3220, or the remote caregiver may suggest or instruct ventilator 3210 with ventilator settings and protocols. As a result, these features allow for remote consultations with respiratory therapists and/or remote diagnosis. Additionally, these features allow for remotely performing rounds/check-ups on patients.

Figure 33:
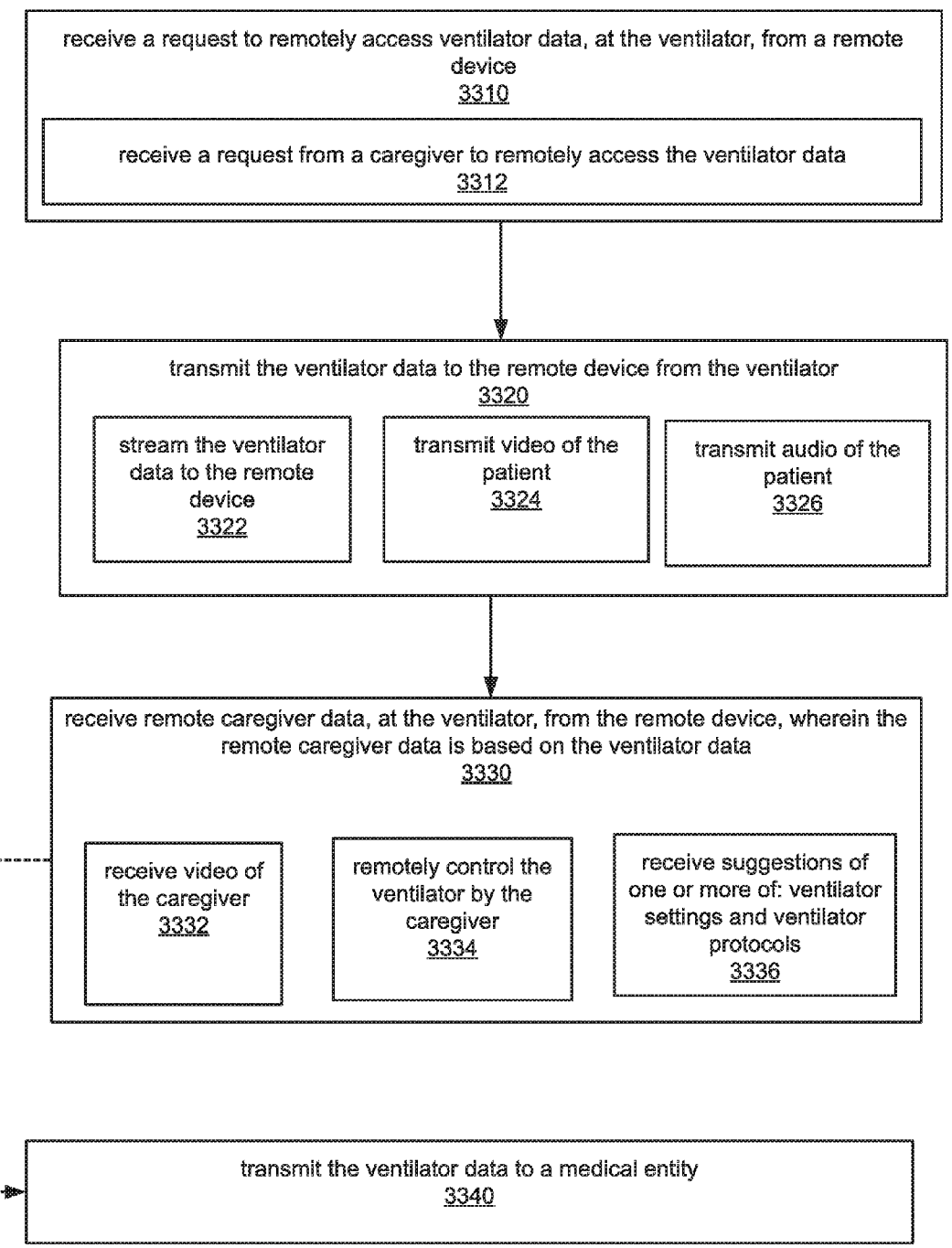
FIG. 33 illustrates an example method for remotely accessing a ventilator.

FIG. 33 depicts an embodiment of method 3300 for remotely accessing a ventilator. In various embodiments, method 3300 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 3300 is performed at least by system 3200, as depicted in FIG. 32.

At step 3310, a request to remotely access ventilator data is received, at the ventilator, from a remote device. For example, a request for remotely accessing ventilator data is sent from remote device 3220 to ventilator 3210. At step 3312, a request from a caregiver to remotely access the ventilator data is received. For example, a remote caregiver requests (via remote device 3220) access to the ventilator data which received at receiver 3212. At step 3320, the ventilator data is transmitted to the remote device from the ventilator. For example, communication 3225 is transmitted to remote device 3220. At step 3322, ventilator data is streamed to the remote device. At step 3324, video of the patient is transmitted to the remote device. At step 3326, audio of the patient is transmitted to the remote device. At step 3330, remote caregiver data is received, at the ventilator, from the remote device, wherein the remote caregiver data is based on the ventilator data. For example, in response to the caregiver receiving communication 3225 (e.g., ventilator data, breathing sounds, etc.), communication 3205 is received at ventilator 3210 based, in part, to communication 3225. At step 3332, video of the caregiver is received at ventilator 3210. At step 3334, instructions to remote control the ventilator by the caregiver are received at ventilator 3210. At step 3336, suggestions of ventilator settings, ventilator protocols, and the like are received at ventilator 3210. At step 3340, communication 3225 (e.g., ventilator data) is transmitted to a medical entity, such as, but not limited to, another remote device, medical device, or system.

Modifying Ventilator Operation Based on Patient Orientation

Figure 34:
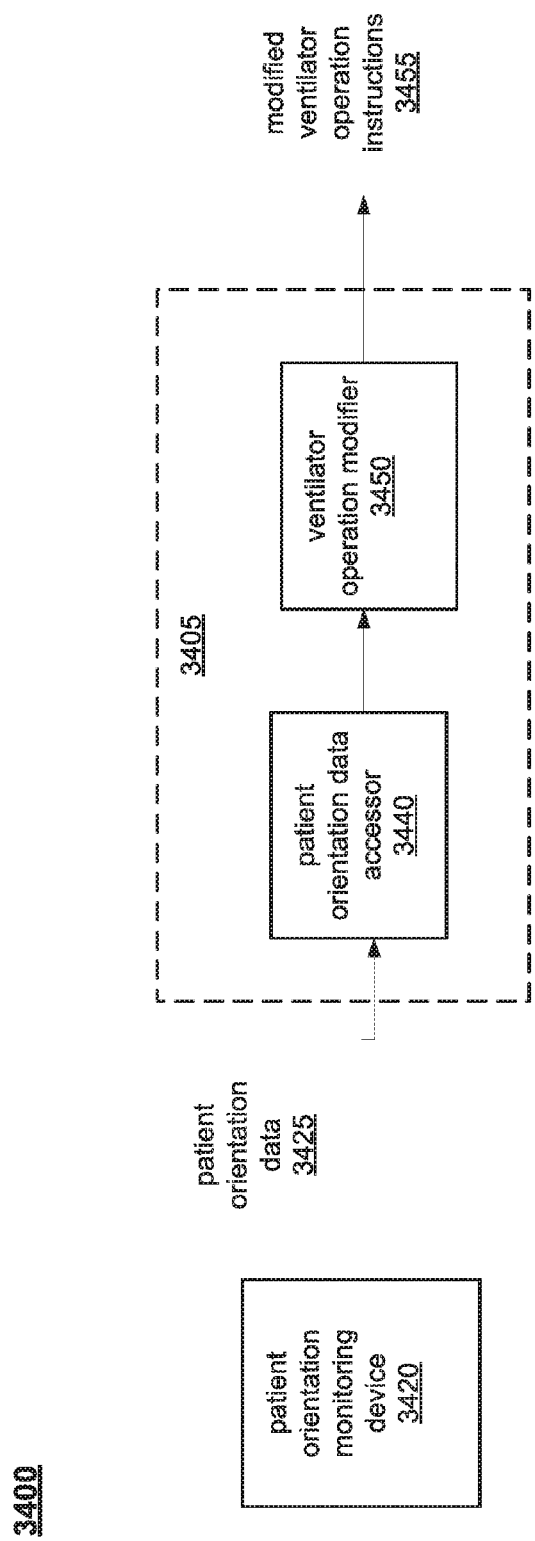

FIG. 34 depicts an embodiment of system 3400 for modifying ventilator operation based on patient orientation. System 3400 includes patient orientation monitoring device 3420, patient orientation data accessor 3440, and ventilator operation modifier 3450. In certain aspects, subsystem 3405 includes patient orientation data accessor 3440 and ventilator operation modifier 3450. It should be appreciated that system 3400 is utilized in conjunction with a ventilator (e.g., ventilator 110, 710, etc.). For example, ventilator operation modifier 3450 is integrated with or associated with the ventilator 110.

Patient orientation monitoring device 3420 is configured to monitor and determine the orientation of a patient (e.g., the patient is on his/her back, side, stomach, etc.) that is associated with a ventilator (e.g., ventilator 110, 710, etc.). In particular, patient orientation monitoring device 3420 generates patient orientation data 3425 that is accessed by patient orientation accessor 3440 to facilitate in modifying ventilator operation based on the patient orientation. In certain aspects, patient orientation monitoring device 3420 includes one or more accelerometers that are attached to the patient. In certain aspects, patient orientation monitoring device 3420 includes a passive radio-frequency identification (RFID) coupled with one or more accelerometers. For example, the RFID is "pinged" and briefly energized by the ventilator 110. In response, the RFID responds with patient orientation data 3425. In various embodiments, patient orientation monitoring device 3420 is attached in any manner, such as an adhesive patch, at a location on the patient that facilitates a proper determination of the orientation of the patient. For example, patient orientation monitoring device 3420 is attached to the middle of the chest or on a shoulder and then initialized. In certain aspects, patient orientation monitoring device 3420 is attached to or integral with a mask that is placed on the patient. In a further embodiment, patient orientation monitoring device 3420 is a camera (e.g., camera 730) associated with the ventilator that captures images of the patient. For example, the camera captures images of the physical orientation of the patient. In another example, the camera utilizes facial recognition techniques to facilitate in determining the orientation of the patient.

It should be appreciated that patient orientation monitoring device 3420 may be in wired or wireless communication with patient orientation accessor 3440. It should also be appreciated that patient orientation is useful in predicting when suction may be needed, as described above. Ventilator operation modifier 3450 is configured to modify the operation of the ventilator 110 based on the patient orientation. In certain aspects, ventilator operation modifier 3450 receives patient orientation data 3425 from patient orientation data accessor 3440 and provides modified ventilator operation instructions 3455 to the ventilator 110 such that the current or normal operation of the ventilator 110 is modified. For example, if a patient is on his side or stomach, then ventilator operation modifier 3450 provides modified ventilator operation instructions 3455 that instruct the ventilator 110 to increase the amount of fresh gas (e.g., by some percentage) to the patient. In certain aspects, modified ventilator operation instructions 3455 instruct the ventilator 110 to modify one or more protocols (e.g., length of the protocol or amount of fresh gas provided during certain portions of the protocol) based on the orientation of the patient.

FIG. 35 depicts an embodiment of method 3500 for modifying ventilator operation based on patient orientation. In various embodiments, method 3500 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 3500 is performed at least by system 3400, as depicted in FIG. 34.

At step 3510, patient orientation of a patient is monitored. The patient is associated with a ventilator. For example, patient orientation monitoring device 3420 monitors the orientation of the patient. At step 3512, images of the patient are captured. For example, a video camera captures images of the patient orientation. At step 3514, patient orientation is monitored based on accelerometers attached to the patient. For example, an adhesive patch comprising accelerometers is attached to the back of a patient to monitor patient orientation. At step 3516, patient orientation is monitored based on accelerometers attached to a mask. For example, accelerometers attached to a mask are utilized to monitor patient orientation. At step 3518, patient orientation is periodically monitored. For example, in response to periodic "pinging," an RFID provides patient orientation. At step 3520, ventilator operation of the ventilator 110 is modified based on the patient orientation. For example, the current or normal operation of the ventilator 110 is modified based on patient orientation. At step 3522, an amount of fresh gas to the patient is increased. For example, based on the patient lying on his back, ventilator operation modifier 3450 provides modified ventilator operation instructions 3455 to the ventilator 110 to increase the amount of fresh gas provided to the patient. At step 3524, a protocol of the ventilator 110 is modified. For example, based on the patient orientation, the length of the protocol is modified.

Logging Ventilator Data

Figure 36:
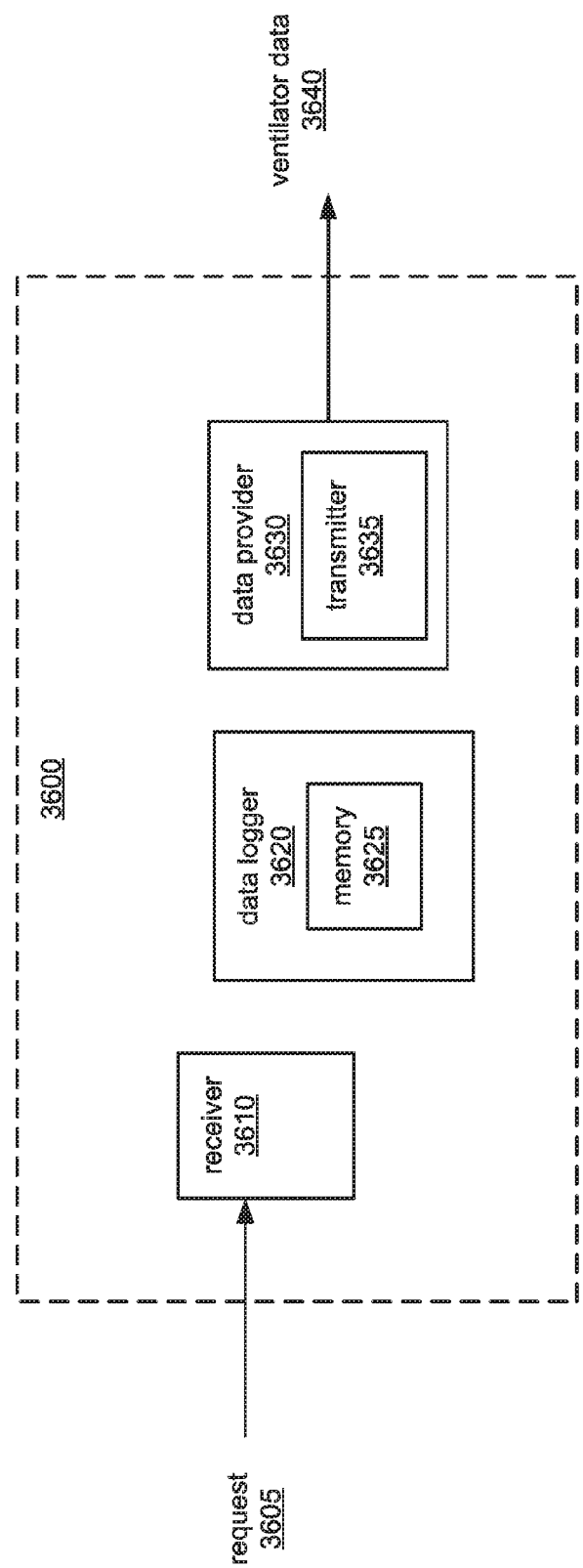

FIG. 36 depicts an embodiment of system 3600 configured for logging ventilator data. In general, system 3600 allows access to the logged ventilator data. It should be appreciated that system 3600 is utilized in conjunction with a ventilator (e.g., ventilator 110, 710, etc.). For example, system 3600 is integrated with or associated with the ventilator 110.

In one example, the ventilator utilizing system 3600 is located at a home of a patient. Accordingly, a caregiver may not be able to check the patient ventilation in person very often. However, as will be described in detail further below, ventilator data is able to be logged and provided to a medical entity, such as a client device of the caregiver. Moreover, system 3600 may store and/or forward or allow remote access to the ventilator data (e.g., ventilator data 17028). The ventilator data 17028 can be any information generated by the ventilator or information associated with ventilator functionality with regards to patient care. For example, the ventilator data 17028 can be, but is not limited to, ventilator mode, oxygen level, flow rates, timing, ventilator settings, or physiological statistics of a patient. The term "logging," used herein describes keeping records or compiling of the ventilator data 17028.

System 3600 includes receiver 3610, data logger 3620 and data provider 3630. Data logger 3620 is configured for logging the ventilator data 17028. For example, as the ventilator 110 generates ventilator data 17028, data logger 3620 logs the data. In certain aspects, the ventilator data 17028 is stored in memory 3625. Receiver 3610 is configured to receive a request for accessing the logged or stored ventilator data 17028. For example, receiver 3610 receives request 3605 for accessing the logged ventilator data 17028 for use by a medical entity 120. In certain aspects, receiver 3610 receives the ventilator data 17028 from the ventilator 110.

Data provider 3630 is configured to provide ventilator data 3640 for use by a medical entity 120. For example, in response to request 3605, transmitter 3635 transmits ventilator data 3640 to the medical entity 120, such as a healthcare system and/or a user interface for patient record keeping. In various embodiments, the ventilator data 17028 is stored for a certain or predetermined amount of time. Also, the ventilator data can be stored locally (e.g., at memory 3625) and forwarded continually, in real-time. In other embodiments, the ventilator data 17028 can be forwarded in intervals, or forwarded in response to one or more triggers. It should be appreciated that the ventilator data 17028 can be overwritten.

The ventilator data 17028 can be logged or captured for billing/charge purposes. For example, the ventilator 110 can track time of use in association with a particular patient to confirm that the patient should be billed for ventilator use. Moreover, the particular ventilator protocols that have been utilized in association with the patient can be tracked. Accordingly, the ventilator data 17028 (e.g., the charge information) can be forwarded into a healthcare network or other network for use in billing or confirmation of charges. The ventilator data 17028 can also be logged or captured for inventory control purposes. For example, the ventilator 110 can positively track the use of oxygen or other gasses, use of disposable tubes/masks, and other consumables associated with the ventilator 110. In particular, the logging of ventilator data 17028 for inventory control purposes is to provide the ventilator data 17028 to a healthcare facility network for use in inventory control/reorder.

Based on contextualized data, the ventilator 110 can positively track a time of use and associate that time of use with a patient. In certain aspects, this tracking is for compliance with federal and/or insurance company rules and to prevent billing fraud. For example, certain billing codes are associated with certain amounts of time that a patient is ventilated, such as the 96 hour rule. For instance, once a patient is ventilated for a minimum of 96 hours, a different billing code is utilized. As a result, the patient's bill may be higher. Therefore, positive tracking of ventilator use in association with a particular patient prevents guessing or estimating a time of use and thus prevents a healthcare facility from committing fraud by overestimating the time a patient has been ventilated.

Figure 37:
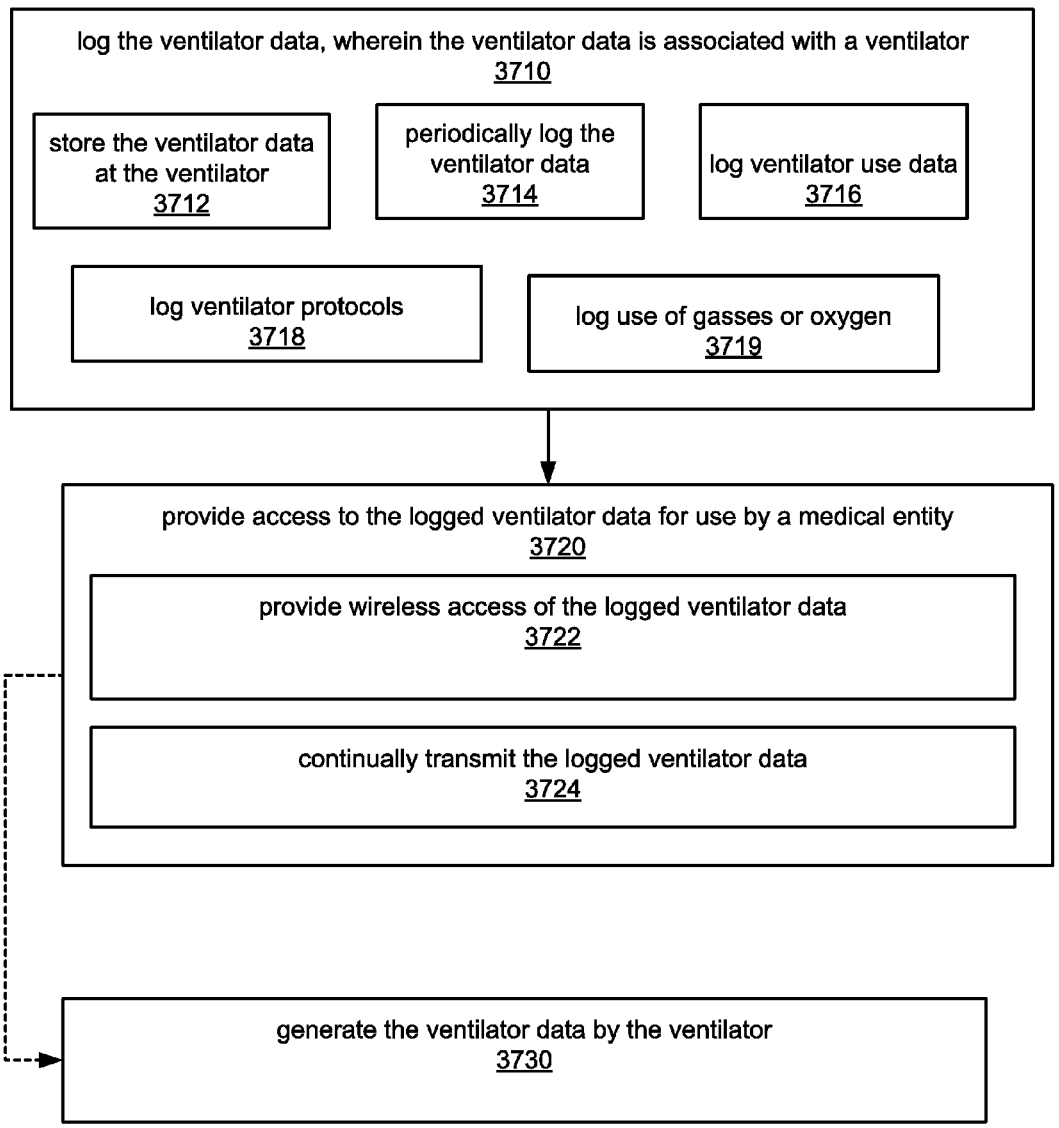
FIG. 37 illustrates an example method for logging ventilator data.

FIG. 37 depicts an embodiment of method 3700 for logging ventilator data. In various embodiments, method 3700 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 3700 is performed at least by system 3600, as depicted in FIG. 36.

At step 3710 of method 3700, ventilator data 3640 is logged, wherein the ventilator data 3640 is associated with a ventilator 1750. At step 3712, ventilator data 3640 is stored at the ventilator 110. For example, ventilator data 3640 is stored locally in memory 3625 of the ventilator 110. At step 3714, ventilator data 3640 of the ventilator 110 is periodically logged. At step 3716, the ventilator use data is logged. For example, the length of use of a ventilator 110 on a patient is logged. At step 3718, ventilator protocols are logged. For example, one or more of a weaning protocol or a lung protection protocol is logged. At step 3719, use of gasses or oxygen is logged. At step 3720, access to the logged ventilator data is provided for use by a medical entity 120. For example, a remote caregiver requests access to the logged ventilator data and the ventilator data is subsequently transmitted to the remote caregiver. At step 3722, wireless access is provided to the logged ventilator data. For example, logged ventilator data is accessed via a cellular connection with the ventilator. At step 3724, the logged ventilator data is continually transmitted. For example, the ventilator data is continually transmitted in real-time to a remote caregiver. The ventilator data 3640 may be generated by the ventilator 110. For example, a ventilator (e.g., ventilator 110 or 710) generates the ventilator data that is logged.

Ventilator Billing and Inventory Management

Figure 38:
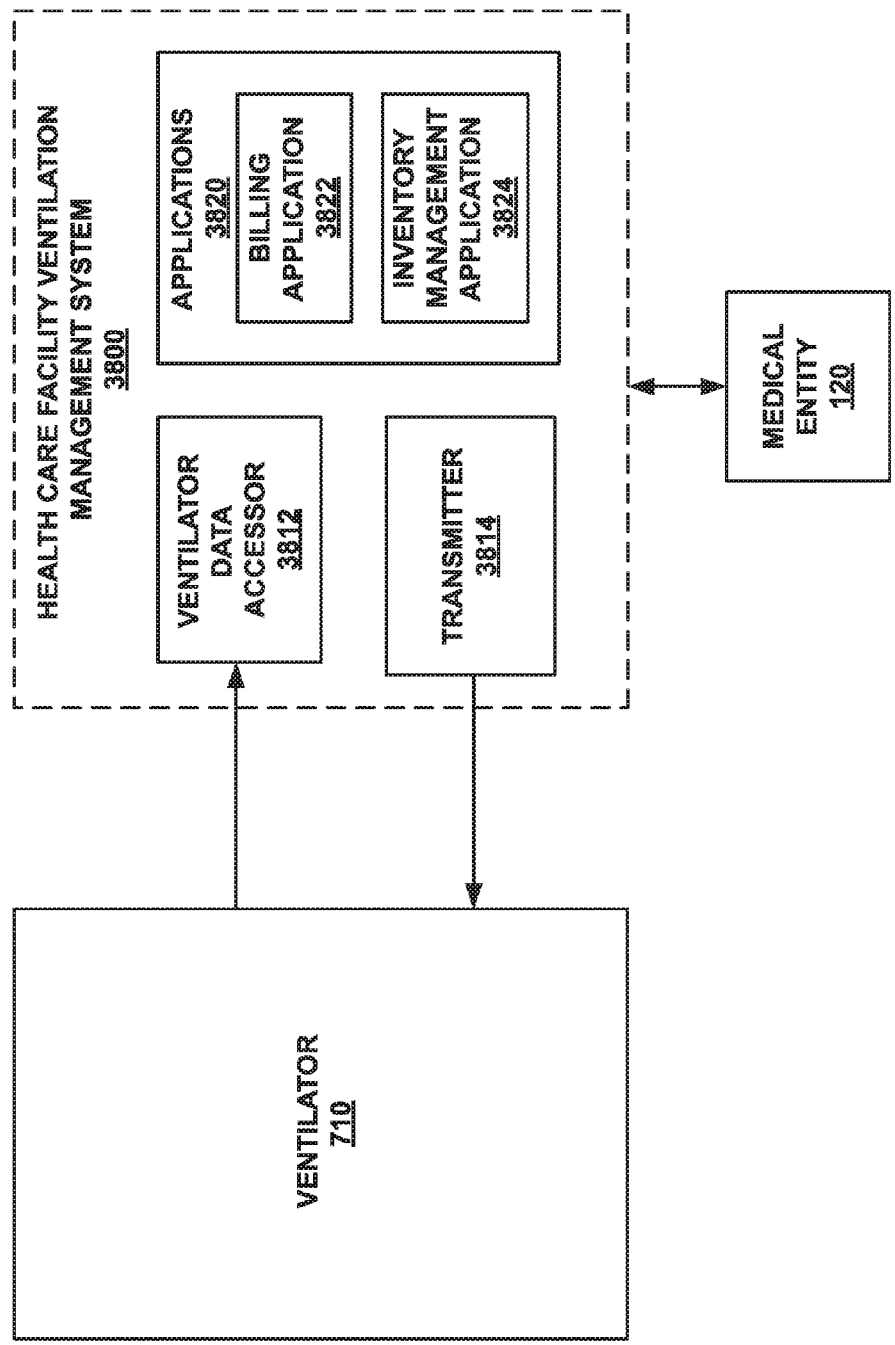

FIG. 38 depicts an embodiment of healthcare facility ventilation management system 3800. System 3800 is associated with a healthcare facility network and is configured to bi-directionally communicate with one or more ventilators (e.g., 710) and/or one or more medical entities (e.g., medical entity 120). System 3800 is similar to system 1300 described above.

System 3800 includes ventilator data accessor 3812, transmitter 3814 and applications 3820. Ventilator data accessor 3812 is configured for accessing ventilator data 3640 from the ventilator 710 (or any other ventilators and/or medical devices). For example, data 3640 (e.g., logged in ventilator or streamed from the ventilator) is remotely accessed. Transmitter 3814 is configured for transmitting a communication/data to a ventilator 710 and/or a medical entity 120, which will be described in further detail below. In certain aspects, transmitter 3814 transmits ADT information to a ventilator 710. Applications 3820 include applications that are utilized by system 3800 for ventilation management. Applications 3820 can include, but are not limited to, billing application 3822 and inventory control application 3824.

Billing application 3822 can utilize ventilator data to generate billing/charges for a patient. For example, billing application 3822 utilizes tracked time, protocols and the like for billing a patient. In certain aspects, the ventilator data 3640 is stored at system 3800, for example, in memory. Inventory management application 3824 can utilize ventilator data 3640 to manage/control inventory. For example, system 3800 receives/accesses ventilator data 3640 and inventory management application 3824 utilizes the ventilator data 3640 for inventory management. In such an example, the use of consumables such as, disposable tubes and/or masks, are tracked and inventory management application 3824 utilizes this data to reorder the consumables. As such, system 1300 includes and/or utilizes a plurality of systems and functions described herein.

In certain aspects, system 1300 includes and utilizes batch data management. For example, batches of data are able to be sent from a ventilator without real-time communication. In certain aspects, system 1300 utilizes system 400 for contextualizing ventilator data, which is described in detail above. In such an example, data associator 420 associates context data 407 and ventilator data 405 such that ventilator data 405 is contextualized. Additionally, transmitter 1314 transmits the contextualized data to medical entity 120 (e.g., a handheld device or ventilator monitoring user interface associated with the medical entity 120).

In certain aspects, system 1300 utilizes system 900 for automatically implementing a ventilator protocol, as described in detail above. For example, ventilator protocol implementor 902 implements a protocol on a ventilator 710 by way of user input at the ventilator 710. Furthermore, ventilator protocol customizer 925 customizes ventilator a protocol based on unique patient information, such as a patient ID, patient lab results, or patient test results. It should be understood that the protocols are pushed to the ventilator from system 1300, for example, by transmitter 1314.

In a further embodiment, system 1300 utilizes system 1100 for implementing a ventilator rule on a ventilator 710, as described in detail above. For example, ventilator rules implementor 1120 implements at least one of the ventilator rules 1105 in response to a determined mode of operation. In such an example, if the ventilator 710 is in a pediatric ventilation mode, certain rules pertaining to gas supply may be implemented. Furthermore, ventilator rules 1105 are customized based on patient contextualized data (e.g., age, sex, weight). For example, maximum and minimum fresh gas flow may be customized based on age, sex or weight of a patient. It should be understood that the rules are pushed to the ventilator 710 from system 1300, for example, by transmitter 1314. It should be appreciated that rules and protocols result in the ventilator 710 doing something automatically (e.g., closed loop) or can result in user guidance (e.g., open loop).

Figure 39:
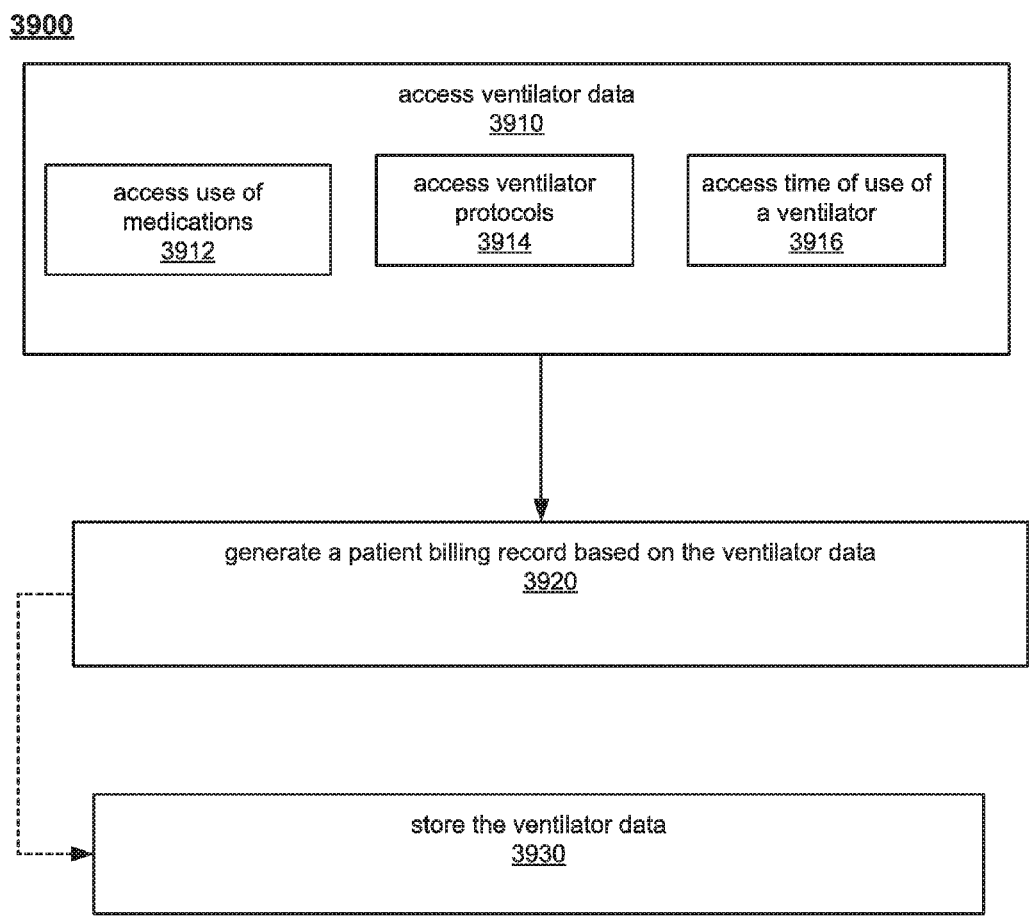
FIG. 39 illustrates an example method for generating a patient billing record.

FIGS. 39 and 40 depict embodiments of a method 3900 for generating a patient billing record and of a method 4000 for ventilation inventory management, respectively. In various embodiments, methods 3900 and 4000, respectively, are carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, methods 3900 and 4000, respectively, are performed at least by system 3800, as depicted in FIG. 38.

At step 3910 of method 3900, ventilator data is accessed. For example, ventilator data accessor 3812 accesses ventilator data 3640 from the ventilator 710. At step 3912, use of medications information is accessed. For example, the information regarding the medication used by a patient is accessed. Also, medications administered through the ventilator 710 may be tracked or recorded. Such information regarding the use of medications may be accessed. At step 3914, ventilator protocols are accessed. At step 3916, time of use of the ventilator is accessed. At step 3920, a patient billing record is generated based on the ventilator data 3640. For example, if a patient uses a ventilator 710 for 48 hours, then billing application 3822 generates a billing record for a patient based on 48 hours of use of the ventilator 710. At step 3930, ventilator data 3640 is stored. For example, system 3800 locally stores the ventilator data 3640.

At step 4010 of method 4000, information regarding use of ventilator consumables is accessed. For example, information regarding tubes or masks is accessed. At step 4012, use of ventilator consumables is accessed by a health care facility ventilation management system. For example, health care facility ventilation management system 3800 accesses the use of ventilator consumables. At step 4020, ventilation inventory is managed based on said use of ventilator consumables. At step 4022, ventilator consumables are reordered. For example, if consumables such as masks, tubes, and the like, are low in quantity, then the consumables are reordered, based in part, on inventor management application 3824. At step 4030, the information regarding the use of ventilator consumables is stored at system 3800, for example, in memory.

Virtual Ventilation Screen

Figure 41:
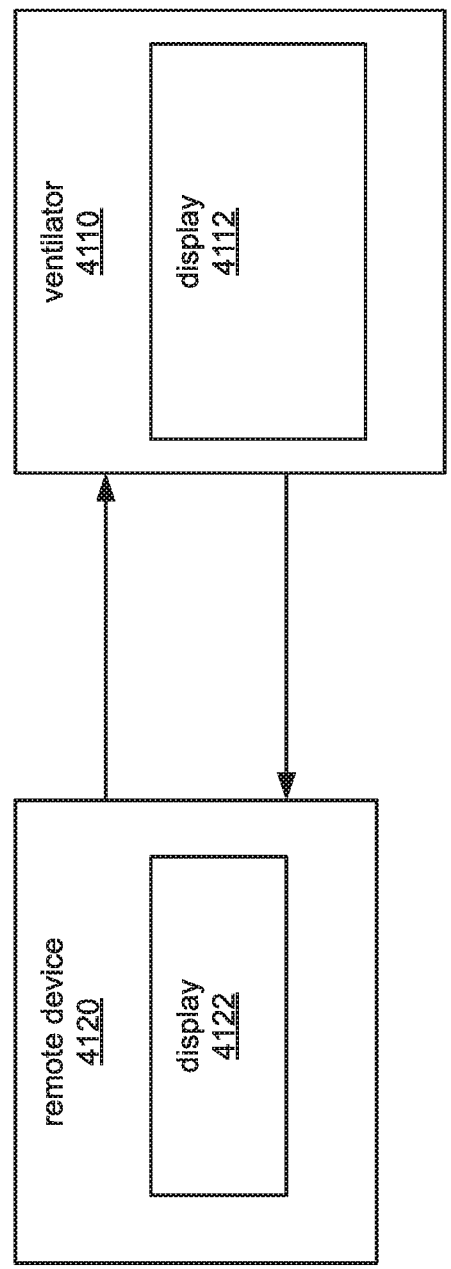

FIG. 41 depicts an embodiment of system 4100 for displaying ventilator data 3640 at a remote device. System 4100 includes at least one ventilator 4110 that bi-directionally communicates (e.g., a local wired/wireless or wide area wired/wireless communication) with remote device 4120. For example, ventilator 4110 is in a home environment (e.g., home environment 3902) and remote device 4120 is located at a remote location, such as hospital 2901. Remote device 4120, can be, but is not limited to a handheld device. Remote device 4120 includes display 4122 and is able to access ventilator data 3640 associated with ventilator 4110. Once remote device 4120 receives the ventilator data 3640, the data can be displayed on display 4122. As such, display 4122 associated with the remote device is a virtual ventilator screen of ventilator 4110. As a result, depending on the device and the login of the user, the virtual ventilator screen allows for remote viewing of ventilator settings and/or remote changing of settings.

Figure 42:
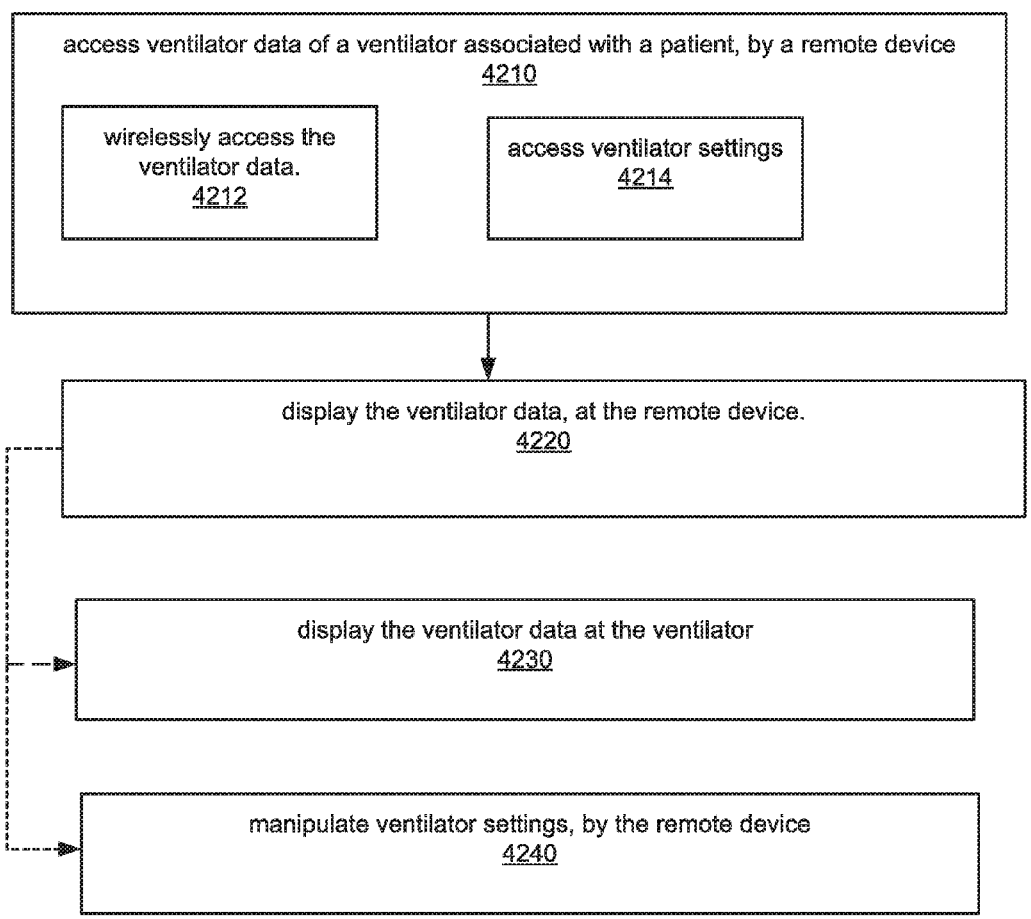
FIG. 42 illustrates an example method for displaying ventilator data at a remote device.

FIG. 42 depicts an embodiment of method 4200 for displaying ventilator data 3640 at a remote device. In various embodiments, method 4200 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 4200 is performed at least by system 4100, as depicted in FIG. 41.

At step 4210 of method 4200, ventilator data 3640 is accessed by a remote device, wherein the ventilator 4110 is associated with a patient. For example, remote device 4120 accesses ventilator 3640 data from the ventilator 4110. At step 4212, ventilator data 3640 is wirelessly accessed. For example, remote device 4120, located in a hospital, wirelessly accesses ventilator data 3640 of ventilator 4110 located at the home of the patient. At step 4214, ventilator settings are accessed. At step 4220, the ventilator data 3640 is displayed at the remote device. For example, the ventilator settings are displayed at remote device 4120. At step 4230, the ventilator data 3640 is displayed at the ventilator. For example, the ventilator data 3640 is concurrently displayed on display 4122 and display 4112. In certain aspects, different ventilator data is displayed on the displays. At step 4240, the ventilator settings are manipulated by the remote device. For example, a caregiver views the ventilator settings on display 4122 and changes/manipulates the ventilator settings of ventilator 4110 via remote device 4120.

Figure 43:
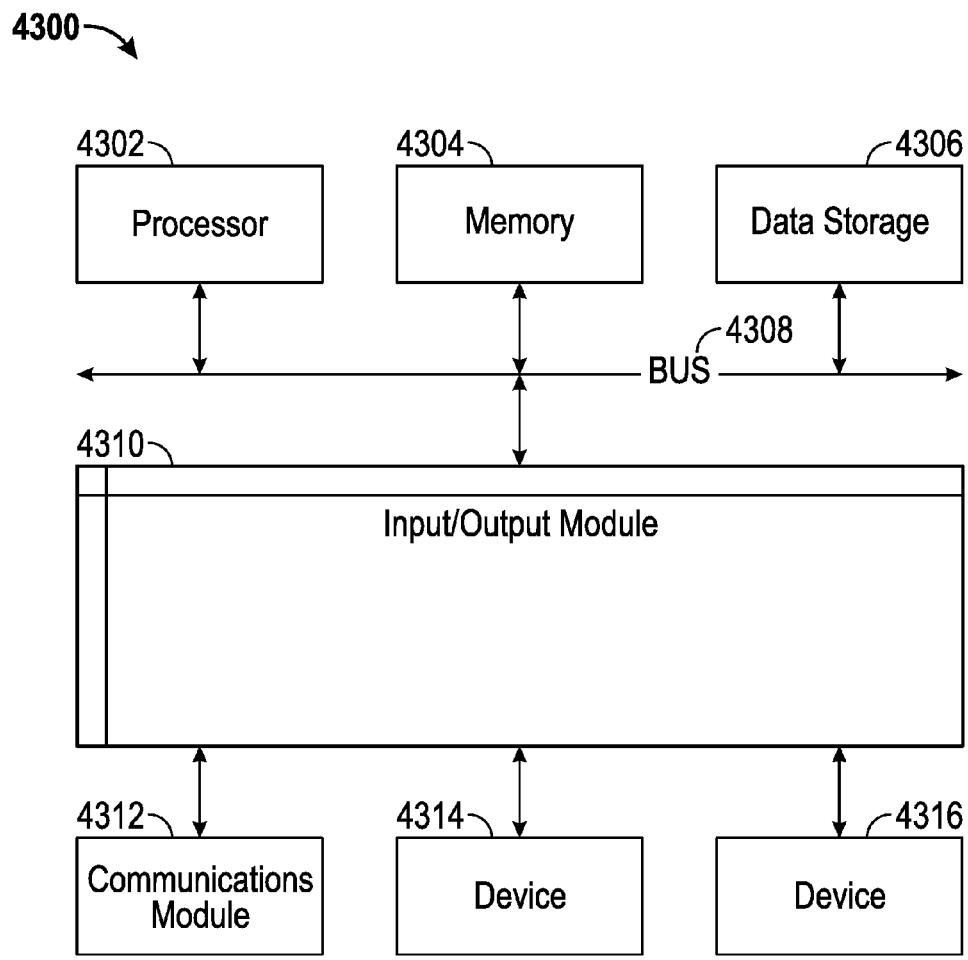
FIG. 43 is a block diagram illustrating an example computer system with which various disclosed systems can be implemented.

FIG. 43 is a block diagram illustrating an example computer system 4300 with which the ventilators 110, clients 130, and medical entities 120 and the other various systems described herein (e.g., system 100, system 400, system 1700, coordination engine 17020, etc.) can be implemented. In certain aspects, the computer system 4300 may be implemented using hardware or a combination of software and hardware, either in a dedicated server, or integrated into another entity, or distributed across multiple entities.

Computer system 4300 includes a bus 4308 or other communication mechanism for communicating information, and a processor 4302 (e.g., processor 17022, 17112, and 1724) coupled with bus 4308 for processing information. By way of example, the computer system 4300 may be implemented with one or more processors 4302. Processor 4302 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 4300 can include, in addition to hardware, code that creates an execution environment for the computer program in question, e.g., code that constitutes processor firmware, a protocol stack, a database management system, an operating system, or a combination of one or more of them stored in an included memory 4304 (e.g., memory 17026, 17104, and 1725), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 4308 for storing information and instructions to be executed by processor 4302. The processor 4302 and the memory 4304 can be supplemented by, or incorporated in, special purpose logic circuitry.

The instructions may be stored in the memory 4304 and implemented in one or more computer program products, i.e., one or more modules of computer program instructions encoded on a computer readable medium for execution by, or to control the operation of, the computer system 4300, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 4304 may also be used for storing temporary variable or other intermediate information during execution of instructions to be executed by processor 4302.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 4300 further includes a data storage device 4306 such as a magnetic disk or optical disk, coupled to bus 4308 for storing information and instructions. Computer system 4300 may be coupled via input/output module 4310 to various devices. The input/output module 4310 can be any input/output module. Example input/output modules 4310 include data ports such as USB ports. The input/output module 4310 is configured to connect to a communications module 4312. Example communications modules 4312 (e.g., communications module 17024, 17110, and 17156) include networking interface cards, such as Ethernet cards and modems. In certain aspects, the input/output module 4310 is configured to connect to a plurality of devices, such as an input device 4314 and/or an output device 4316 (e.g., display device 1752). Example input devices 4314 include a keyboard and a pointing device, e.g., a mouse or a trackball, by which a user can provide input to the computer system 4300. Other kinds of input devices 4314 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 4316 include display devices, such as a LED (light emitting diode), CRT (cathode ray tube), or LCD (liquid crystal display) screen, for displaying information to the user.

According to one aspect of the present disclosure, the ventilators 110, clients 130, and medical entities 120 can be implemented using a computer system 4300 in response to processor 4302 executing one or more sequences of one or more instructions contained in memory 4304. Such instructions may be read into memory 4304 from another machine-readable medium, such as data storage device 4306. Execution of the sequences of instructions contained in main memory 4304 causes processor 4302 to perform the process steps described herein. One or more processors in a multi-processing arrangement may also be employed to execute the sequences of instructions contained in memory 4304. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 200) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 4300 can include clients and servers. A client and server are generally remote from each other and typically interact through a communication network. The relationship of client and server arises by virtue of computer programs running on the respective computers and having a client-server relationship to each other. Computer system 4300 can be, for example, and without limitation, a desktop computer, laptop computer, or tablet computer. Computer system 4300 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 4302 for execution. Such a medium may take many forms, including, but not limited to, non-volatile media, volatile media, and transmission media. Non-volatile media include, for example, optical disks, magnetic disks, or flash memory, such as data storage device 4306. Volatile media include dynamic memory, such as memory 4304. Transmission media include coaxial cables, copper wire, and fiber optics, including the wires that comprise bus 4308. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A monitoring system for multiple medical ventilators comprising:
   a memory comprising instructions; and
   a processor configured to execute the instructions to:
   receive ventilator data generated by a plurality of medical ventilators used by a plurality of patients;
   identify a ventilating configuration for each of the plurality of medical ventilators based on the ventilator data;
   associate each patient from the plurality of patients with a respective one of the plurality of medical ventilators;
   determine an identification and ventilation status for each patient associated with one of the plurality of medical ventilators; and
   provide instructions to concurrently display information indicative of the ventilating configuration of each of the plurality of medical ventilators and indicative of the identification and ventilation status of each patient associated with one of the plurality of medical ventilators, wherein the identification for each patient comprises at least one of a patient care area or patient location.

2. The monitoring system of claim 1, wherein the information indicative of the ventilating configuration of each of the plurality of medical ventilators comprises at least one of an apnea interval, a bias flow, a compression volume, a $CO_2$ value, a demand flow, a diameter, an average end tidal $CO_2$, a fraction of inspired oxygen ($FiO_2$), a flow cycle, or a flow trigger.

3. The monitoring system of claim 1, wherein the information indicative of the identification and ventilation status of each patient comprises at least one measured physiological statistic for dynamic compliance (Cdyn), inverse ratio ventilation (TIE), mandatory ventilation rate, mandatory exhaled tidal volume (VTE), total lung ventilation per minute, positive end respiratory pressure (PEEP), peak expiratory flow rate (PEFR), peak inspiratory flow rate (PIFR), mean airway pressure, peak airway pressure, or total ventilation rate.

4. The monitoring system of claim 1, wherein the ventilator data for the plurality of medical ventilators comprises at least one of a medical ventilator start time, a medical ventilator mode, tidal volume (VT), ventilation frequency, fraction of inspired oxygen ($FiO_2$), or positive end respiratory pressure (PEEP).

5. The monitoring system of claim 1, wherein the information comprises at least one of a notification for at least one patient that indicates at least one of an alert for the medical ventilator associated with the patient, or an alert indicating a non-compliance of the medical ventilator with a compliance policy.

6. The monitoring system of claim 1, wherein the information comprises at least one of a total estimated ventilation cost for patients in a first period, a total estimated ventilation cost for patients in a second period, baseline period, a total estimated weaning cost for patients in the first period, a total estimated weaning cost for patients in the second period, or a difference in cost between the first period and the second period.

7. The monitoring system of claim 1, wherein the identification for each patient further comprises at least one of an account identification or a patient name.

8. The monitoring system of claim 1, wherein the processor is further configured to transmit a request to at least one of the plurality of medical ventilators, the request comprising at least one a request to remotely access the medical ventilator, to remotely control the medical ventilator, to annotate data stored on the medical ventilator, to change information for a patient associated with the medical ventilator, or obtain diagnostic information for the medical ventilator.

9. The monitoring system of claim 1, wherein the ventilator data for the plurality of medical ventilators is received over a network.

10. The monitoring system of claim 1, wherein the information is displayed using an interface configured for a mobile device.

11. The monitoring system of claim 1, wherein the ventilator data comprises a physiological statistic obtained from the medical ventilator for a patient, and wherein the processor is further configured to receive a threshold value for generating a notification when the physiological statistic for the patient exceeds the threshold value.

12. The monitoring system of claim 1, wherein the information comprises a report, for at least one of the patients, of at least one of weaning, medical ventilator settings, medical ventilator history, lung protection, or patient details.

13. The monitoring system of claim 12, wherein the ventilator data is received at the monitoring system, and wherein parameters for generating the report are configurable at the monitoring system.

14. The monitoring system of claim 12, wherein the report comprises at least one of analytics data or summary data.

15. The monitoring system of claim 12, wherein the report for weaning comprises current, minimum, and maximum values for a patient information for at least one of a fraction of inspired oxygen (FiO2), minute ventilation, positive end respiratory pressure (PEEP), tidal volume (VT), total ventilation rate, and work of breathing measured.

16. The monitoring system of claim 1, wherein the information indicative of the identification and ventilation status of each patient comprises providing information for patients in a care area, the information for patients in a care area indicative of at least one of a number of weaning candidates, average number days on a medical ventilator, average number of hours from a first weaning marker to a first spontaneous breathing trial (SBT), average number of hours from the first weaning marker to a final extubation, a reintubation rate, a total estimated ventilation cost for patients with weaning markers, an average estimated ventilation cost for patients with weaning markers, patient weaning information grouped by physician, a number of patients with alarm notifications, an average number of times patients in the care area have had physiological statistics exceeding acceptable thresholds, or a percentage of time patients in the care area have had physiological statistics exceeding acceptable thresholds.

17. The monitoring system of claim 16, wherein the information for patients in the care area is provided in at least one of a text format or chart format.

18. A method for monitoring multiple medical ventilators using a single interface, the method comprising:
receiving ventilator data generated by a plurality of medical ventilators used by a plurality of patients;
identifying a ventilating configuration for each of the plurality of medical ventilators based on the ventilator data;
associating each patient from the plurality of patients with a respective one of the plurality of medical ventilators;
determining an identification and ventilation status for each patient associated with the plurality of medical ventilators; and
providing instructions to concurrently display, information indicative of the ventilating configuration of each of the plurality of medical ventilators and indicative of the identification and ventilation status of each patient associated with one of the plurality of medical ventilators,
wherein the identification for each patient comprises at least one of a patient care area or patient location.

19. The method of claim 18, wherein the information indicative of the ventilating configuration of each of the plurality of medical ventilators comprises at least one of an apnea interval, a bias flow, a compression volume, a CO2 value, a demand flow, a diameter, an average end tidal CO2, a fraction of inspired oxygen (FiO2), a flow cycle, or a flow trigger.

20. The method of claim 18, wherein the information indicative of the identification and ventilation status of each patient comprises at least one measured physiological statistic for dynamic compliance (Cdyn), inverse ratio ventilation (I/E), mandatory ventilation rate, mandatory exhaled tidal volume (VTE), total lung ventilation per minute, positive end respiratory pressure (PEEP), peak expiratory flow rate (PEFR), peak inspiratory flow rate (PIFR), mean airway pressure, peak airway pressure, or total ventilation rate.

21. The method of claim 18, wherein the ventilator data for the plurality of medical ventilators comprises at least one of a medical ventilator start time, a medical ventilator mode, tidal volume (VT), ventilation frequency, fraction of inspired oxygen (FiO2), or positive end respiratory pressure (PEEP).

22. The method of claim 18, wherein the information comprises a notification for at least one patient that indicates at least one of an alert for the medical ventilator associated with the patient, or an alert indicating a non-compliance of the medical ventilator with a compliance policy.

23. The method of claim 18, wherein the information comprises a report, for at least one of the patients, of at least one of weaning, medical ventilator settings, medical ventilator history, lung protection, and patient details.

24. The method of claim 18, wherein the identification for each patient further comprises at least one of an account identification or a patient name.

25. The method of claim 18, further comprising transmitting a request to at least one of the plurality of medical ventilators, to remotely access the medical ventilator, to remotely control the medical ventilator, to annotate data stored on the medical ventilator, to change information for a patient associated with the medical ventilator, or to obtain diagnostic information for the medical ventilator.

26. The method of claim 18, wherein the ventilator data for the plurality of medical ventilators is received over a network.

27. The method of claim 18, wherein the information is displayed using an interface configured for a mobile device.

28. The method of claim 18, wherein the ventilator data comprises a physiological statistic obtained from the medical ventilator for a patient, and wherein the method further comprises receiving a threshold value for generating a notification when the physiological statistic for the patient exceeds the threshold value.

29. The method of claim 18, wherein the information comprises at least one of a total estimated ventilation cost for patients in a first period, a total estimated ventilation cost for patients in a second, period, a total estimated weaning cost for patients in the first period, a total estimated weaning cost for patients in the second period, or a difference in cost between the first period and the second period.

30. The method of claim 29, wherein the ventilator data is received at a device, and wherein parameters for generating a report are configurable at the device.

31. The method of claim 29, further comprising preparing a report comprises with at least one of analytics data or summary data.

32. The method of claim 29, further comprising a report for weaning comprises current, minimum, and maximum values for a patient information for at least one of a fraction of inspired oxygen (FiO2), minute ventilation, positive end respiratory pressure (PEEP), tidal volume (VT), total ventilation rate, and work of breathing measured.

33. The method of claim 18, wherein the information indicative of the identification and ventilation status of each patient comprises providing information for patients in a care area, the information for patients in a care area indicative of at least one of a number of weaning candidates, average number days on a medical ventilator, average number of hours from a first weaning marker to a first spontaneous breathing trial (SBT), average number of hours from the first weaning marker to a final extubation, a reintubation rate, a total estimated ventilation cost for patients with weaning markers, an average estimated ventilation cost for patients with weaning markers, patient weaning information grouped by physician, a number of patients with alarm notifications, an average number of times patients in the care area have had physiological statistics exceeding acceptable thresholds, or a percentage of time patients in the care area have had physiological statistics exceeding acceptable thresholds.

34. The method of claim 33, wherein the information for patients in the care area is provided in at least one of a text format or chart format.

35. A machine-readable storage medium comprising machine-readable instructions for causing a processor to execute a method for monitoring multiple medical ventilators using a single device, the method comprising:
receiving ventilator data generated by a plurality of medical ventilators used by a plurality of patients;
identifying a ventilating configuration for each of the plurality of medical ventilators based on the ventilator data;
associating each patient from the plurality of patients with a respective one of the plurality of medical ventilators;
determining an identification and ventilation status for each patient associated with one of the plurality of medical ventilators; and
providing instructions to concurrently display information indicative of the ventilating configuration of each of the plurality of medical ventilators and indicative of the identification and ventilation status of each patient associated with one of the plurality of medical ventilators,
wherein the identification for each patient comprises at least one of a patient care area or patient location.

* * * * *